US008404686B2

(12) United States Patent
Smith et al.

(10) Patent No.: US 8,404,686 B2
(45) Date of Patent: *Mar. 26, 2013

(54) METHOD OF TREATMENT OR PROPHYLAXIS

(75) Inventors: Maree Therese Smith, Bardon (AU); Bruce Douglas Wyse, Corinda (AU)

(73) Assignee: Spinifex Pharmaceuticals Pty Ltd, South Yarra, Victoria (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/167,980

(22) Filed: Jun. 24, 2011

(65) Prior Publication Data

US 2012/0004259 A1    Jan. 5, 2012

Related U.S. Application Data

(60) Continuation of application No. 12/849,727, filed on Aug. 3, 2010, which is a division of application No. 11/315,354, filed on Dec. 23, 2005, now Pat. No. 7,795,275.

(30) Foreign Application Priority Data

Dec. 24, 2004 (AU) ............................... 2004907332

(51) Int. Cl.
    A61K 31/50    (2006.01)
    A61K 31/495   (2006.01)
    A61K 31/44    (2006.01)
    A61K 31/47    (2006.01)
    A61K 31/41    (2006.01)

(52) U.S. Cl. ........ 514/247; 514/248; 514/301; 514/307; 514/359

(58) Field of Classification Search .................. 514/247, 514/248, 301, 307, 359
    See application file for complete search history.

(56) References Cited

U.S. PATENT DOCUMENTS

| | | | |
|---|---|---|---|
| 3,531,485 A | 9/1970 | Freed | |
| 3,975,795 A | 5/1976 | Rubela et al. | |
| 4,812,462 A | 3/1989 | Blankley et al. | |
| 5,091,390 A | 2/1992 | Ardecky et al. | |
| 5,204,354 A | 4/1993 | Chakravarty et al. | |
| 5,236,934 A | 8/1993 | Van Atten et al. | |
| 5,246,943 A | 9/1993 | Blankley et al. | |
| 5,292,726 A | 3/1994 | Ashton et al. | |
| 5,338,740 A | 8/1994 | Carpino et al. | |
| 5,348,955 A | 9/1994 | Greenlee | |
| 5,385,894 A | 1/1995 | Delaszlo et al. | |
| 5,441,959 A | 8/1995 | Chakravarty et al. | |
| 5,545,651 A | 8/1996 | Duncia et al. | |
| 5,683,997 A | 11/1997 | Buhlmayer et al. | |
| 5,789,415 A | 8/1998 | Carpino et al. | |
| 6,448,280 B1 | 9/2002 | Carey et al. | |
| 7,795,275 B2 * | 9/2010 | Smith et al. ................ | 514/301 |
| 2003/0158211 A1 | 8/2003 | Bencherif et al. | |
| 2003/0199424 A1 | 10/2003 | Smith et al. | |
| 2003/0220375 A1 | 11/2003 | Wood et al. | |
| 2004/0097565 A1 | 5/2004 | Terashita et al. | |
| 2004/0133011 A1 | 7/2004 | Waddell | |
| 2004/0180941 A1 | 9/2004 | Hepworth | |
| 2004/0192729 A1 | 9/2004 | Rudolf et al. | |
| 2005/0187269 A1 | 8/2005 | Kuroita et al. | |

FOREIGN PATENT DOCUMENTS

| | | |
|---|---|---|
| EP | 0245637 | 11/1987 |
| EP | 1356815 | 10/2003 |
| EP | 1239867 | 1/2005 |
| GB | 2323783 | 7/1998 |
| WO | 9205784 | 4/1992 |
| WO | 9220661 | 11/1992 |
| WO | 9320816 | 10/1993 |
| WO | 9323378 | 11/1993 |
| WO | 9413646 | 6/1994 |
| WO | 9428896 | 12/1994 |
| WO | 9500498 | 1/1995 |
| WO | 9522525 | 8/1995 |
| WO | 9907413 | 2/1999 |
| WO | 0020398 | 4/2000 |
| WO | 0144239 | 6/2001 |
| WO | 0182916 | 11/2001 |
| WO | 0205799 | 1/2002 |
| WO | 0240008 | 5/2002 |
| WO | 02057264 | 7/2002 |
| WO | 02060923 | 8/2002 |
| WO | 03064414 | 8/2003 |
| WO | 03066577 | 8/2003 |
| WO | 03077912 | 9/2003 |
| WO | 03097024 | 11/2003 |
| WO | 03099279 | 12/2003 |
| WO | 2004006959 | 1/2004 |
| WO | 2004024061 | 3/2004 |
| WO | 2004099248 | 11/2004 |
| WO | 2005/080384 | 9/2005 |
| WO | 2006066361 | 6/2006 |
| WO | 2007134136 | 11/2007 |
| WO | 03101381 | 11/2011 |

OTHER PUBLICATIONS

Carey FA and Sunbergrj, "Advaned Organic Chemistry, 3rd Ed., Part A: Structure and Mechanisms," Plenum Press, New York, 1990, p. 146.

(Continued)

*Primary Examiner* — Paul Zarek
(74) *Attorney, Agent, or Firm* — Wolff IP, a Prof. Corp.; Jessica R. Wolff, Esq.

(57) ABSTRACT

The present invention is directed to methods and agents that are useful in the prevention and amelioration of signs and symptoms associated with neuropathic conditions. More particularly, the present invention discloses the use of angiotensin II receptor 2 ($AT_2$ receptor) antagonists for the treatment, prophylaxis, reversal and/or symptomatic relief of neuropathic pain, including mechanical hyperalgesia, thermal or mechanical allodynia, diabetic pain and entrapment pain, in vertebrate animals and particularly in human subjects. The $AT_2$ receptor antagonists may be provided alone or in combination with other compounds such as those that are useful in the control of neuropathic conditions.

13 Claims, 13 Drawing Sheets

OTHER PUBLICATIONS

Carey, R.M.; (2005); "Update on the role of the AT2 receptor"; Curr. Nephrol. Hypertens; 14: 67-71.
Carrasquillo, et al.: "Rodent models clarify the role of cells expressing the substance P receptor in pain", (2004); Drug Discovery Today: disease models; 1(2): 107-113.
Chui, et al.: Non-peptide angiotensin II receptor antagonists. !!a. Pharmacology of S-8308; European Journal of Pharm., 157 (1998) 13-21.
Glinka, et al. 1994, Bioorg. Med Chem. Lett. 4: 2337.
Glinka, et al. 1994, Bioorg. Med. Chem. Lett. 4:1479.
Klutchko, et al. (1994): Tetrahydroisoquinoline derivatives wit AT2-specific angiotensis II receptor binding inhibitory activity; Bioorganic & Medical Chemistry Letters; vol. 4, No. 1, pp. 57-62.
Malik, et al: Effect of angiotensin-converting-enzyme (ACE) inhibitor tandolapril on human diabetic neuropathy: randomised double-bind controlled trial; Early Report, Lancet 1998; 352: 1978-81.
PCT/AU2007/000339 International Preliminary Report on Patentability mailed May 1, 2007.
PCT/AU2007/000339 International Search Report mailed May 1, 2007.
PCT/AU2007/000339 Written Opinion mailed May 1, 2007.
PCT/GB2011/001096 International Search Report and Written Opinion mailed Aug. 29, 2011.
Pechlivanova, et al.: (2002): "Interaction of angiotensin II and adenosine A1 and A2A receptor ligands on the writhing test in mice"; Pharmacol. Biochem. and Behaviour: 72: 23-28.
Podar, et al.: "The Role of Angiotensin Converting Enzyme Inhibitors and Angiotensin II Receptor Antagonists in the Management of Diabetic Complications," Drugs 2002:62 (14) p. 2007-2012.
Priest, et al., (1999): Biochemistry: 43: 9866-9876.
Rahbar, et al.; (1999)"Novel inhibitors of advanced glycation endproducts"; biochem. Biophys. Res. Commun.: 262: 651-656.
Stedman's Medical Dictionary 27th ed., Lippincott Williams & Wilkins, Philadelphia, 2000 "Neuropathy".
Stoll, et al., Arterioscler Thromb Vasc. Biol. (2002), 22:2, p. 231-237.
Takai, et al., "Antinociceptive Effects of Angiotensin-Converting Enzymes Inhibitors" Life Science (1996) v. 59, p. PL331-336.
Timmermans, et al., 1993 Pharmacol Reviews 45(2): 205-251.
U.S. Appl. No. 11/315,354 Final Rejection mailed Jan. 21, 2010.
U.S. Appl. No. 11/315,354 Non-Final Rejection mailed Jan. 2, 2009.
U.S. Appl. No. 11/315,354 Non-Final Rejection mailed May 22, 2009.
U.S. Appl. No. 11/315,354 Non-Final Rejection mailed Jul. 30, 2008.
Wexler, et al., (1996), J. Med. Chem., 39(3), p. 625-656.
Wolf, Gunter (2002), "The road not taken: role of angiotensin II type 2 receptor in pathophysiology" Nephrol Dial Transplant 17, p. 195-198.
Zhao, et al., J. Neurochem., (2003) 85(3), pp. 759-767.
Van Atten, et al., "A Novel Series of Selective, Non-Peptide Inhibitors of Angiotensin II Binding to the AT20 Site," J. Med. Chem. (1993), 36(25) pp. 3985-3992.

* cited by examiner

A

B

A

B

A

B

METHOD OF TREATMENT OR PROPHYLAXIS

This application is a continuation of U.S. application Ser. No. 12/849,727, filed Aug. 3, 2010, which is a divisional application of U.S. application Ser. No. 11/315,354, filed Dec. 23, 2005, now U.S. Pat. No. 7,795,275, which claims priority to Australian Application No. 2004907332, filed Dec. 24, 2004, the contents of each of which are hereby incorporated by reference in their entireties.

DESCRIPTION OF THE SEQUENCE LISTING TEXT FILE SUBMITTED ELECTRONICALLY

The contents of the text file submitted electronically are incorporated herein by reference in their entirety: A computer readable format copy of the Sequence Listing (filename: SPPL_002_01US_SubSeqList.txt, date recorded: Aug. 1, 2011, file size 16 kilobytes) was submitted on Sep. 12, 2011 in Ser. No. 12/849,727.

FIELD OF THE INVENTION

This invention relates generally to compounds that are useful in the prevention and amelioration of signs and symptoms associated with a neuropathic condition. More particularly, the present invention relates to the use of angiotensin II receptor 2 ($AT_2$ receptor) antagonists for the treatment, prophylaxis, reversal and/or symptomatic relief of neuropathic pain, including mechanical hyperalgesia, thermal or mechanical allodynia, diabetic pain and entrapment pain, in vertebrate animals and particularly in human subjects. The $AT_2$ receptor antagonists may be provided alone or in combination with other compounds such as those that are useful in the control of neuropathic conditions.

BACKGROUND OF THE INVENTION

Neuropathic pain may occur when the peripheral and/or central nervous systems are sensitized following an injury to the peripheral nervous system or to the central nervous system. In contrast to the immediate pain (nociceptive pain) caused by tissue injury, neuropathic pain can develop days or months after a traumatic injury and is frequently long-lasting or chronic. Moreover, neuropathic pain can occur spontaneously or as a result of stimulation that normally is not painful. Neuropathic pain conditions are characterized by hyperesthesia (enhanced sensitivity to natural stimuli), hyperalgesia (abnormal sensitivity to pain), allodynia (widespread tenderness, characterized by hypersensitivity to tactile stimuli) and/or spontaneous burning pain.

The etiology of neuropathic pain is diverse and includes both trauma and disease. For example, traumatic nerve compression or crush and traumatic injury to the brain or spinal cord are common causes of neuropathic pain. Furthermore, traumatic nerve injuries may also cause the formation of neuromas, in which pain occurs as a result of aberrant nerve regeneration. In addition, cancer-related neuropathic pain is caused when tumor growth painfully compresses adjacent nerves, brain or spinal cord. Neuropathic pain also is associated with systemic diseases such as diabetes, alcoholism, herpes zoster, AIDS/HIV, syphilis and various other autoimmune diseases.

Although there are effective remedies for treating nociceptive pain, neuropathic pain is often resistant to available drug therapies. In addition, current therapies have serious side-effects including, for example, cognitive changes, sedation, nausea and, in the case of narcotic drugs, tolerance and dependence. Many patients suffering from neuropathic pain are elderly or have other medical conditions that particularly limit their ability to tolerate the side-effects associated with available drug therapy.

Accordingly, there is a need for the provision of agents that are effective for treating and/or preventing the painful symptoms associated with neuropathic pain and with less undesirable side-effects.

SUMMARY OF THE INVENTION

Despite intensive investigations on the biological role of the angiotensin II type 2 receptor ($AT_2$ receptor) spanning over 15 years and more than 2000 publications, there is no clear evidence of a therapeutic utility for this receptor (see, for example, the recent review by Steckelings et al. 2005, Peptides 26:1401-1409). Surprisingly, however, the present inventors have discovered that $AT_2$ receptor antagonists are effective in the prevention or attenuation of the painful symptoms of neuropathic conditions including primary and secondary neuropathies. In one aspect, therefore, the invention provides methods for the treatment or prophylaxis of a neuropathic condition in a subject. In some embodiments, the neuropathic condition is treated or prevented by administering to the subject an effective amount of an $AT_2$ receptor antagonist. Non limiting examples of suitable $AT_2$ receptor antagonists include small molecules, nucleic acids, peptides, polypeptides, peptidomimetics, carbohydrates, lipids or other organic (carbon containing) or inorganic molecules, as further described herein.

The $AT_2$ receptor antagonist is suitably administered in the form of a composition comprising a pharmaceutically acceptable carrier or diluent. The composition may be administered by injection, by topical application or by the oral route including sustained-release modes of administration, over a period of time and in amounts, which are effective to treat or prevent the neuropathic condition. In some embodiments, the neuropathic condition results from a disease of the nerves (i.e., a primary neuropathy). In other embodiments, the neuropathic condition results from a systemic disease (i.e., secondary neuropathy). In specific embodiments, the neuropathic condition is a peripheral neuropathic condition, especially that following mechanical nerve injury or biochemical nerve injury such as painful diabetic neuropathy (PDN) or a related condition.

In accordance with the present invention, $AT_2$ receptor antagonists have been shown to prevent or attenuate the painful symptoms associated with a neuropathic condition. Thus, in another aspect, the invention provides methods for preventing or attenuating neuropathic pain, especially peripheral neuropathic pain, in a subject. In some embodiments, neuropathic pain is prevented or attenuated by administering to the subject an effective amount of an $AT_2$ receptor antagonist, which is suitably in the form of a composition comprising a pharmaceutically acceptable carrier and/or diluent.

In a related aspect, the invention provides methods for producing analgesia in a subject, especially in a subject who has, or is at risk of developing, a neuropathic condition. These methods generally comprise administering to the subject an effective amount of an $AT_2$ receptor antagonist, which is suitably in the form of a composition comprising a pharmaceutically acceptable carrier and/or diluent.

In a further aspect, the present invention contemplates the use of an $AT_2$ receptor antagonist in the manufacture of a medicament for producing analgesia in a subject, especially in a subject who has, or is at risk of developing, a neuropathic condition.

Any $AT_2$ receptor antagonist can be used in the compositions and methods of the invention. In some embodiments, the $AT_2$ receptor antagonist is selected from compounds, and their pharmaceutically compatible salts, represented by the formula (I):

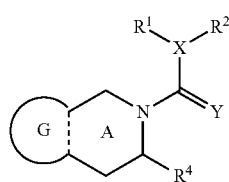

(I)

wherein:
$R^1$ and $R^2$ are independently selected from H, benzyl, substituted benzyl, phenyl, substituted phenyl, $C_{1-6}$alkyl, substituted $C_{1-6}$alkyl, $C_{3-6}$cycloalkyl, substituted $C_{3-6}$cycloalkyl, and heteroaryl, providing that both $R^1$ and $R^2$ are not hydrogen,
$R^4$ is selected from a carboxylate, carboxylic acid, sulfate, phosphate, sulfonamide, phosphonamide or amide,
X is selected from CH, nitrogen, sulfur or oxygen with the proviso that when X is sulfur or oxygen one of $R^1$ or $R^2$ is absent,
Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$,
G is a five or six membered, homoaromatic or unsaturated, substituted or unsubstituted, heterocyclic ring including but not limited to the following rings systems:

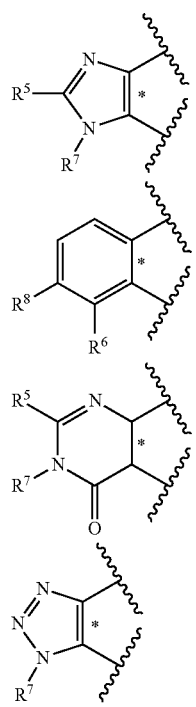

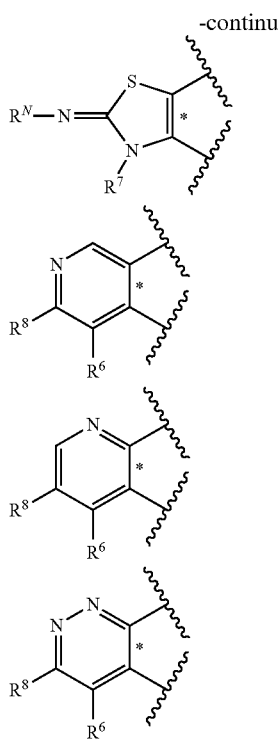

where the symbol '*' indicates the bond shared between the fused rings 'A' and 'G',
$R^5$ is selected from H, $C_{1-6}$alkyl, phenyl, substituted phenyl, substituted $C_{1-6}$alkyl, $C_{1-6}$alkoxy, or substituted $C_{1-6}$alkoxy,
$R^6$ and $R^8$ are independently selected from H, $C_{1-6}$alkyl, substituted $C_{1-6}$alkyl, $C_{1-6}$alkoxy, substituted $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen, and
$R^7$ is selected from phenyl, substituted phenyl, benzyl, substituted benzyl, biphenyl, substituted biphenyl, biphenylmethylene, substituted biphenyl methylene, napthyl, substituted napthyl, napthylmethylene, and substituted napthylmethylene.

In other embodiments, the $AT_2$ receptor antagonist is selected from compounds, and their pharmaceutically compatible salts, represented by the formula (II):

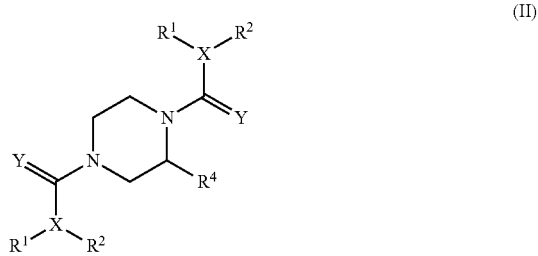

(II)

wherein:
$R^1$ and $R^2$ are independently selected from H, phenyl, substituted phenyl, benzyl, substituted benzyl, $C_{1-6}$alkyl, substituted $C_{1-6}$alkyl, $C_{3-6}$cycloalkyl, substituted $C_{3-6}$cycloalkyl, heteroaryl, and substituted heteroaryl, substituted biphenylmethylene and saturated and unsaturated substituted biphenylmethylene, provided that one of $R^1$ or $R^2$ is not hydrogen, $R^4$ is selected from a carboxylate, carboxylic acid, sulfate, phosphate, sulfonamide, phosphonamide or amide, X is selected from CH, nitrogen, sulfur or oxygen with the proviso that when X is sulfur or oxygen one of $R^1$ or $R^2$ is absent, and Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, In still other embodiments, the $AT_2$ receptor antagonist is selected from compounds, and their pharmaceutically compatible salts, represented by the formula (III):

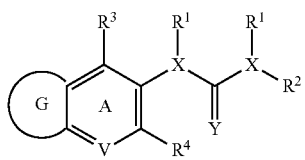

(III)

wherein:

$R^1$, $R^2$ and $R^3$ are independently selected from H, phenyl, substituted phenyl, benzyl substituted benzyl, $C_{1-6}$alkyl, substituted $C_{1-6}$alkyl, with the proviso that at least one of $R^1$ or $R^2$ are not hydrogen, X is selected from CH, nitrogen, sulfur or oxygen with the proviso that when X is sulfur or oxygen, one of $R^1$ or $R^2$ is absent, or is aryl or heteroaryl with the proviso that both $R^1$ and $R^2$ are absent, V is selected from CH or nitrogen atom, Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, $R^4$ is selected from a carboxylate, carboxylic acid, sulfate, phosphate, sulfonamide, phosphonamide, or amide, G is a five or six membered, homoaromatic or unsaturated, substituted or unsubstituted, heterocyclic ring including but not limited to the following rings systems:

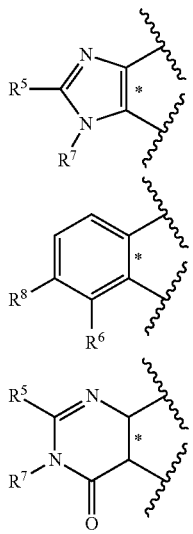

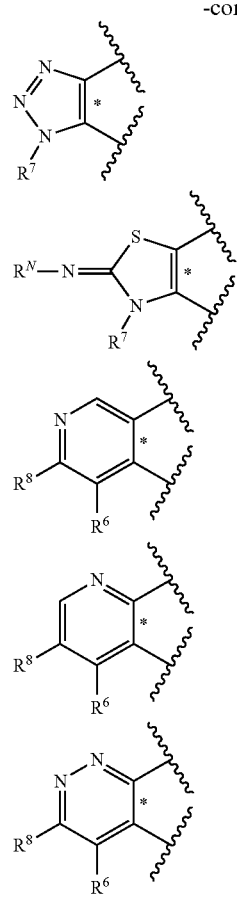

where the symbol indicates the bond shared between the fused rings 'A' and 'G', $R^5$ is selected from H, $C_{1-6}$alkyl, phenyl, substituted phenyl, substituted $C_{1-6}$alkyl, or $C_{1-6}$alkoxy, $R^6$ and $R^8$ are independently selected from H, $C_{1-6}$alkyl, substituted $C_{1-6}$alkyl $C_{1-6}$alkoxy, substituted, $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen, and $R^7$ is selected from phenyl, substituted phenyl, benzyl, substituted benzyl, biphenyl, substituted biphenyl, biphenylmethylene, substituted biphenylmethylene, napthyl, substituted napthyl, napthylmethylene, and substituted napthylmethylene.

In still other embodiments, the $AT_2$ receptor antagonist is selected from compounds, and their pharmaceutically compatible salts, represented by the formula (IV):

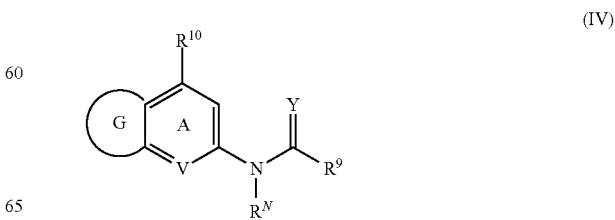

(IV)

wherein:

$R^{10}$ is selected from H, halogen, $C_{1-6}$alkyl, phenyl, substituted phenyl, substituted $C_{1-6}$alkyl, or $C_{1-6}$alkoxy, $R^9$ is selected from —$NR^{13}R^{14}$, wherein $R^{13}$ and $R^{14}$ are independently selected from $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$; a five or six membered, saturated or unsaturated, substituted or unsubstituted, carbocyclic or heterocyclic ring including but not limited to:

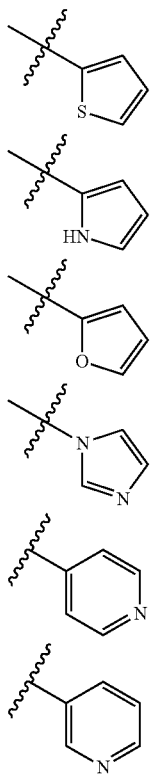

V is selected from CH or a nitrogen atom,

Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, G is a five or six membered homoaromatic or heterocyclic, unsaturated, substituted ring including but not limited to the following rings systems:

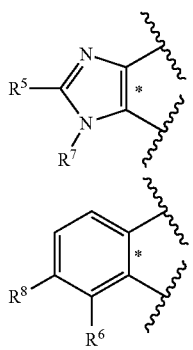

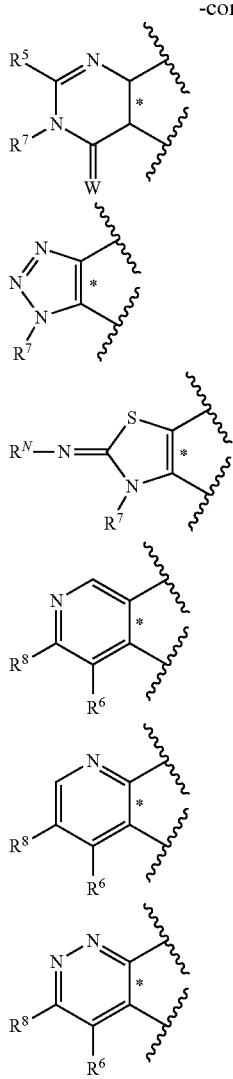

where the symbol '*' indicates the bond shared between the fused rings 'A' and 'G', $R^5$ is selected from $C_{1-6}$alkyl, phenyl, substituted phenyl, substituted $C_{1-6}$alkyl, or $C_{1-6}$alkoxy, W is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, $R^6$ and $R^8$ are independently selected from H, $C_{1-6}$alkyl, substituted $C_{1-6}$alkyl $C_{1-6}$alkoxy, substituted, $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen, and $R^7$ is selected from phenyl, substituted phenyl, benzyl, substituted benzyl, biphenyl, substituted biphenyl, biphenylmethylene, substituted biphenylmethylene, napthyl, substituted napthyl, napthylmethylene, and substituted napthylmethylene.

In still other embodiments, the $AT_2$ receptor antagonist is selected from compounds, and their pharmaceutically compatible salts, represented by the formula (V):

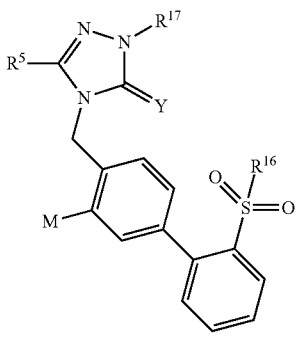

(V)

wherein:

M is H or a halogen (fluoro, bromo, iodo, chloro), $R^5$ is selected from $C_{1-6}$alkyl, phenyl, substituted phenyl, substituted $C_{1-6}$alkyl, or $C_{1-6}$alkoxy, $R^{16}$ is selected from $C_{1-6}$alkylamino, $C_{1-6}$dialkylamino, substituted $C_{1-6}$alkylamino, substituted dialkylamino, arylamino, diarylamino, substituted arylamino, substituted diarylamino, alkylarylamino, dialkylarylamino, substituted alkylarylamino, substituted dialkylarylamino, heteroarylamino, substituted heteroarylamino, cycloalkylamino, dicycloalkylamino, diheteroarylamino, alkylcarbonylamino, arylcarbonylamino, alkylarylcarbonylamino, cycloalkylcarbonylamino, and $R^{17}$ is selected from $C_{1-6}$alkyl, substituted $C_{1-6}$alkyl, phenyl, substituted phenyl, benzyl, substituted benzyl, biphenyl, substituted biphenyl, biphenylmethylene, substituted biphenylmethylene, naphthyl, substituted naphthyl, heteroaryl, or substituted heteroaryl.

In further embodiments, the $AT_2$ receptor antagonist is selected from $AT_2$ receptor antagonist peptides, illustrative examples of which include hexa-, hepta- and octapeptides, and their pharmaceutically compatible salts, represented by the formula:

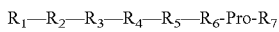

(VIII)

wherein:

$R_1$ is absent or is selected from hydrogen, succinyl, L-aspartyl, sarcosyl, L-seryl, succinamyl, L-propyl, glycyl, L-tyrosyl, $N_\alpha$-nicotinoyl-tyrosyl, or D- or L-asparagyl;

$R_2$ is selected from arginyl or N-benzoylcarbonyl arginyl;

$R_3$ is absent or valyl;

$R_4$ is absent or is selected from L-phenylalanyl or L-tyrosyl;

$R_5$ is selected from valyl, L-isoleucyl, L-alanyl or L-lysyl;

$R_6$ is selected from L-histidyl, L-isoleucyl, L-tyrosyl or p-aminophenylalanyl; and $R_7$ is selected from L-alanine, L-tyrosine, L- or D-leucine, glycine, L-isoleucine or β-alanine residue.

In other embodiments, the $AT_2$ receptor antagonist is selected from antigen-binding molecules that are immuno-interactive with an $AT_2$ receptor polypeptide.

In still other embodiments, the $AT_2$ receptor antagonist is selected from nucleic acid molecules that inhibit or otherwise reduce the level or functional activity of an expression product of an $AT_2$ receptor gene, illustrative examples of which include antisense molecules, ribozymes and RNAi molecules.

In yet another aspect, the invention provides methods for identifying agents that antagonize an $AT_2$ receptor. These methods typically comprise contacting a preparation with a test agent, wherein the preparation comprises (i) a polypeptide comprising an amino acid sequence corresponding to at least a biologically active fragment of an $AT_2$ receptor polypeptide, or to a variant or derivative thereof; or (ii) a polynucleotide that comprises at least a portion of a genetic sequence that regulates the expression of a gene that encodes an $AT_2$ receptor polypeptide, wherein the polynucleotide is operably linked to a reporter gene. A detected decrease in the level or functional activity of the $AT_2$ receptor polypeptide, or an expression product of the reporter gene, relative to a normal or reference level or functional activity in the absence of the test agent, indicates that the agent is an $AT_2$ receptor antagonist.

In some embodiments, the methods comprise contacting a first sample of cells expressing an $AT_2$ receptor with an $AT_2$ receptor ligand and measuring a marker; contacting a second sample of cells expressing the $AT_2$ receptor with an agent and the ligand, and measuring the marker; and comparing the marker of the first sample of cells with the marker of the second sample of cells. In illustrative examples, these methods measure the levels of various markers (e.g., Zfhep expression; nitric oxide levels or nitric oxide synthase levels) or combinations of markers associated with the activation of the AT2 receptor or with the proliferation or differentiation of the cells. In these examples, an agent tests positive if it inhibits Zfhep expression or reduces the level of nitric oxide or the level or functional activity of nitric oxide synthase or the differentiation of the cells.

Still another aspect of the present invention provides methods of producing an agent for producing analgesia in a subject, especially in a subject who has, or is at risk of developing, a neuropathic condition. These methods generally comprise: testing an agent suspected of antagonizing an $AT_2$ receptor, as broadly described above; and synthesizing the agent on the basis that it tests positive for the antagonism. Suitably, the method further comprises derivatising the agent, and optionally formulating the derivatized agent with a pharmaceutically acceptable carrier or diluent, to improve the efficacy of the agent for treating or preventing the neuropathic condition.

DETAILED DESCRIPTION OF THE INVENTION

1. Definitions

Figure 1:
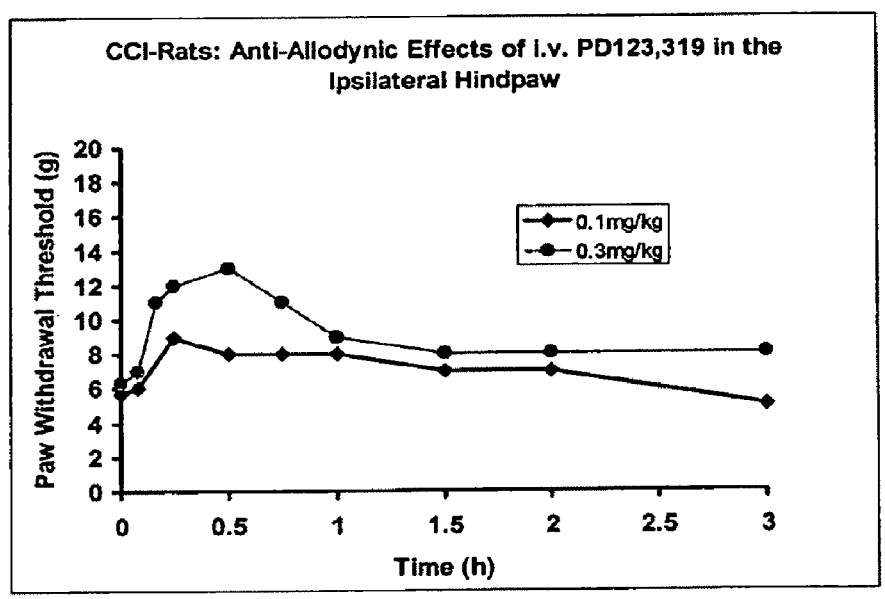
FIG. 1 is a graphical representation showing that single bolus doses of intravenous (i.v.) PD-123,319 (0.1 & 0.3 mg/kg) produce dose-dependent (A) relief of tactile allodynia in the ipsilateral hindpaw of CCI-rats (n=2) and (B) antinociception in the contralateral hindpaw of the same animals.
Figure 1:
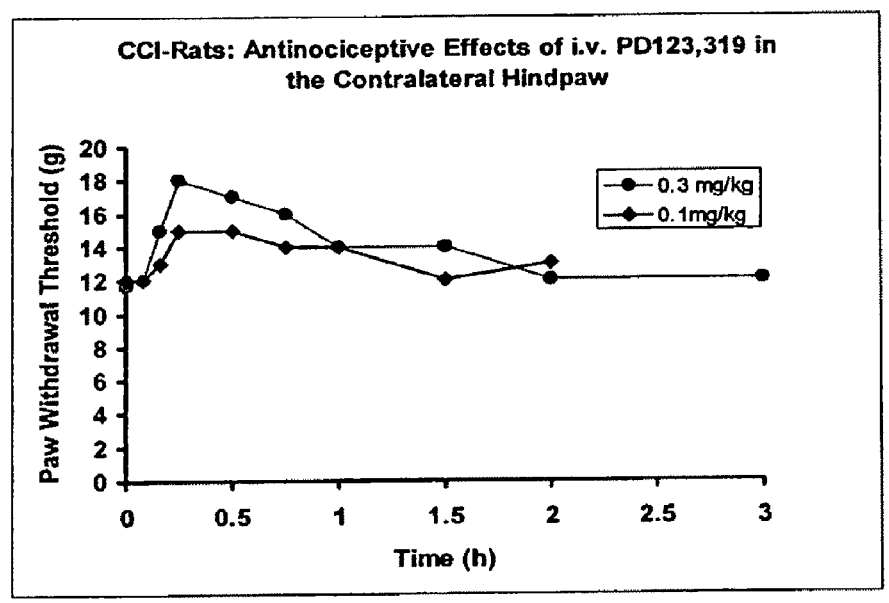

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

Unless otherwise indicated, the term "acyl" denotes a group containing the moiety C=O (and not being a carboxylic acid, ester or amide) Preferred acyl includes C(O)—R, wherein R is hydrogen or an alkyl, alkenyl, alkynyl, aryl, heteroaryl or heterocyclyl residue, preferably a $C_{1-20}$ residue. Examples of acyl include formyl; straight chain or branched alkanoyl such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutanoyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl.

If a number of carbon atoms is not specified, the term "alkenyl," unless otherwise indicated, refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$alkenyl" means an alkenyl radical having from 2 to 6 carbon atoms. Alkenyl groups include, but are not limited to, ethenyl, propenyl, butenyl, 2-methylbutenyl and cyclohexenyl. The straight, branched or cyclic portion of the alkenyl group may contain double bonds and may be substituted if a substituted alkenyl group is indicated.

As used herein, "alkenylene" refers to a straight, branched or cyclic, preferably straight or branched, bivalent aliphatic hydrocarbon group, preferably having from 2 to about 20 carbon atoms and at least one double bond, more preferably 2 to 12 carbons, even more preferably lower alkenylene. The alkenylene group is optionally substituted with one or more "alkyl group substituents." There may be optionally inserted along the alkenylene group one or more oxygen, sulfur or substituted or unsubstituted nitrogen atoms, where the nitrogen substituent is alkyl as previously described. Exemplary alkenylene groups include —CH=CH— CH=CH— and —CH=CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

The terms "alkoxy," "alkenoxy," "alkynoxy," "aryloxy," "heteroaryloxy," "heterocyclyloxy" and "acyloxy" respectively denote alkyl, alkenyl, alkynyl aryl, heteroaryl, heterocyclyl and acyl groups as herein defined when linked by oxygen.

"Alkoxy," unless otherwise indicated, represents either a cyclic or non-cyclic alkyl group attached through an oxygen bridge. "Alkoxy" therefore encompasses the definitions of alkyl and cycloalkyl below. For example, alkoxy groups include but are not limited to methoxy, oxy ethoxy, n-propyloxy, i-propyloxy, cyclopentyloxy and cyclohexyloxy.

As used herein, "alkyl" is intended to include both branched and straight-chain saturated aliphatic hydrocarbon group and may have a specified number of carbon atoms. For example, $C_1$-$C_{10}$, as in "$C_1$-$C_{10}$alkyl" is defined to include groups having 1, 2, 3, 4, 5, 6, 7, 8, 9 or 10 carbons in linear or branched arrangement. For example, "$C_1$-$C_{10}$alkyl" specifically includes, but is not limited to, methyl, ethyl, n-propyl, i-propyl, n-butyl, t-butyl, i-butyl, pentyl, hexyl, heptyl, octyl, nonyl, decyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulfur or substituted or unsubstituted nitrogen atoms, where the nitrogen substituent is alkyl as previously described. Exemplary alkylene groups include methylene (—C$_2$—), ethylene (—CH$_2$CH$_2$—), propylene (—(C$_2$)$_3$—), cyclohexylene (—C$_6$H$_{10}$—), methylenedioxy (—O—CH$_2$—O—) and ethylenedioxy (-O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkylidene" refers to a bivalent group, such as =CR9R0, which is attached to one atom of another group, forming a double bond. Exemplary alkylidene groups are methylidene (=CH2) and ethylidene (=CHCH$_3$). As used herein, "arylalkylidene" refers to an alkylidene group in which either R9 or R0 is and aryl group. As used herein, "diarylalkylidene" refers to an alkylidene group in which R9 and R0 are both aryl groups. "Diheteroarylalkylidene" refers to an alkylidene group in which R9 and R0 are both heteroaryl groups.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$alkynyl" means an alkynyl radical having from 2 to 6 carbon atoms. Alkynyl groups include, but are not limited to, ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as, for example, —CH$_2$Ph, —CH$_2$CH$_2$Ph, CH(CH$_3$)CH$_2$CH(CH$_3$)Ph.

As used herein, "alkynylene" refers to a straight, branched or cyclic, preferably straight or branched, bivalent aliphatic hydrocarbon group, preferably having from 2 to about 20 carbon atoms and at least one triple bond, more preferably 2 to 12 carbons, even more preferably lower alkynylene. The alkynylene group is optionally substituted with one or more "alkyl group substituents." There may be optionally inserted along the alkynylene group one or more oxygen, sulfur or substituted or unsubstituted nitrogen atoms, where the nitrogen substituent is alkyl as previously described. Exemplary alkynylene groups include —C≡C—C≡C—, —C≡C— and —C≡C—C$_2$—. The term "lower alkynylene" refers to alkynylene groups having 2 to 6 carbons. Preferred alkynylene groups are lower alkynylene, with alkynylene of 3 to 4 carbon atoms being particularly preferred.

The term "allodynia" as used herein refers to the pain that results from a non-noxious stimulus i.e. pain due to a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

As used herein, the term "antagonist" means an agent that decreases or inhibits the biological activity of an $AT_2$ gene (Agtr2 gene) or an expression product thereof including an $AT_2$ receptor polypeptide.

As used herein, the term "$AT_2$ receptor" means an angiotensin II type 2 receptor ($AT_2$) receptor polypeptide that can bind angiotensin II and/or one or more other ligands. The term "$AT_2$ receptor" encompasses vertebrate homologs of $AT_2$ receptor family members, including, but not limited to, mammalian, reptilian and avian homologs. Representative mammalian homologs of $AT_2$ receptor family members include, but are not limited to, murine and human homologs.

The term "anti-allodynia" is used herein to describe states of reduced pain perception, including absence from pain sensations as well as states of reduced or absent sensitivity to non-noxious stimuli. Such states of reduced or absent pain perception are induced by the administration of a pain-controlling agent or agents and occur without loss of consciousness, as is commonly understood in the art.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative according to the invention to produce an antigenic or immunogenic response in an animal, suitably a mammal, to which it is administered, wherein the response includes the production of elements which specifically bind the polypeptide or fragment thereof.

As used herein, "aromatic" or "aryl" is intended to mean, unless otherwise indicated, any stable monocyclic or bicyclic carbon ring of up to 7 atoms in each ring, wherein at least one ring is aromatic. Examples of such aryl elements include, but are not limited to, phenyl, naphthyl, tetrahydronaphthyl, indanyl, biphenyl, phenanthryl, anthryl or acenaphthyl.

"Aralkyl" means alkyl as defined above which is substituted with an aryl group as defined above, e.g., —CH$_2$phenyl, —(CH$_2$)$_2$phenyl, —(CH$_2$)$_3$phenyl, —H$_2$CH(CH$_3$)CH$_2$phenyl, and the like and derivatives thereof.

As used herein, "arylene" refers to a monocyclic or polycyclic, preferably monocyclic, bivalent aromatic group, preferably having from 3 to about 20 carbon atoms and at least one aromatic ring, more preferably 3 to 12 carbons, even more preferably lower arylene. The arylene group is optionally substituted with one or more "alkyl group substituents." There may be optionally inserted around the arylene group one or more oxygen, sulfur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "arylidene" refers to an unsaturated cyclic bivalent group where both points of attachment are on the same atom of the ring. Exemplary arylidene groups include, but are not limited to, quinone methide moieties that have the formula:

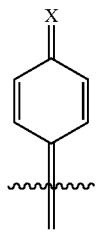

where X is O, S or NR9. "Heteroarylidene" groups are arylidene groups where one or two, preferably two, of the atoms in the ring are heteroatoms, such as, but not limited to, O, S and N.

As used herein, the term "biological activity" means any observable effect flowing from the interaction between an AT$_2$ receptor polypeptide and a ligand. Representative, but non-limiting, examples of biological activity in the context of the present invention include association of an AT$_2$ receptor with a ligand, including an endogenous ligand such as angiotensin II or an AT$_2$ receptor antagonist. The term "biological activity" also encompasses both the inhibition and the induction of the expression of an AT$_2$ receptor polypeptide. Further, the term "biological activity" encompasses any and all effects flowing from the binding of a ligand by an AT$_2$ receptor polypeptide.

The term "causalgia" as used herein refers to the burning pain, allodynia, and hyperpathia after a traumatic nerve lesion, often combined with vasomotor and sudomotor dysfunction and later trophic changes.

By "complex regional pain syndromes" is meant the pain that includes, but is not limited to, reflex sympathetic dystrophy, causalgia, sympathetically maintained pain, and the like.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "cycloalkenyl" means a monocyclic unsaturated hydrocarbon group and may have a specified number of carbon atoms. For example, "cycloalkenyl" includes but is not limited to, cyclobutenyl, cyclopentenyl, 1-methylcyclopentenyl, cyclohexenyl and cyclohexadienyl.

Unless otherwise indicated, the term "cycloalkyl" or "aliphatic ring" means a monocyclic saturated aliphatic hydrocarbon group and may have a specified number of carbon atoms. For example, "cycloalkyl" includes, but is not limited to, cyclopropyl, methyl-cyclopropyl, 2,2-dimethyl-cyclobutyl, 2-ethyl-cyclopentyl, cyclohexyl.

By "derivative," as applied to peptides and polypeptides, refers to a peptide or polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions or deletions that provide for functional equivalent molecules.

By "effective amount", in the context of treating or preventing a condition is meant the administration of that amount of active to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

As appreciated by those of skill in the art, "halo" or "halogen" as used herein is intended to include chloro, fluoro, bromo and iodo.

"Heteroaralkyl" group means alkyl as defined above which is substituted with a heteroaryl group, e.g., —CH$_2$pyridinyl, —(CH$_2$)$_2$pyrimidinyl, —(CH$_2$)$_3$imidazolyl, and the like, and derivatives thereof.

The term "heteroaryl" or "heteroaromatic," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, bezofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl.

Further examples of "heteroaryl" and "heterocyclyl" include, but are not limited to, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazoyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As used herein, "heteroarylene," unless otherwise indicated, refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-imidazolylene.

The term "heterocycle", "heteroaliphatic" or "heterocyclyl" as used herein is intended to mean a 5- to 10-membered nonaromatic heterocycle containing from 1 to 4 heteroatoms selected from the group consisting of O, N and S, and includes bicyclic groups.

"Heterocyclylalkyl" group means alkyl as defined above which is substituted with a heterocycle group, e.g., —CH$_2$pyrrolidin-1-yl, —(CH$_2$)$_2$piperidin-1-yl, and the like, and derivatives thereof.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

The term "hydrocarbyl" as used herein includes any radical containing carbon and hydrogen including saturated, unsaturated, aromatic, straight or branched chain or cyclic including polycyclic groups. Hydrocarbyl includes but is not limited to C$_1$-C$_8$alkyl, C$_2$-C$_8$alkenyl, C$_2$-C$_8$alkynyl, C$_2$-C$_{10}$cycloalkyl, aryl such as phenyl and naphthyl, Ar (C$_1$-C$_8$)alkyl such as benzyl, any of which may be optionally substituted.

By "hyperalgesia" is meant an increased response to a stimulus that is normally painful.

Reference herein to "immuno-interactive" includes reference to any interaction, reaction, or other form of association between molecules and in particular where one of the molecules is, or mimics, a component of the immune system.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, diabetic pain, entrapment pain, and the like.

"Nociceptive pain" refers to the normal, acute pain sensation evoked by activation of nociceptors located in non-damaged skin, viscera and other organs in the absence of sensitization.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

By "operably linked" is meant that transcriptional and translational regulatory polynucleotides are positioned relative to a polypeptide-encoding polynucleotide in such a manner that the polynucleotide is transcribed and the polypeptide is translated.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28$^{th}$ Edition, W. B. Saunders Company, Philadelphia, Pa.). The present invention is particularly concerned with the alleviation of pain associated with neuropathic conditions. The goal of treatment of pain is to reduce the degree of severity of pain perceived by a treatment subject.

By "pharmaceutically acceptable carrier" is meant a solid or liquid filler, diluent or encapsulating substance that may be safely used in topical, local or systemic administration.

The terms "pharmaceutically compatible salt" and "pharmaceutically acceptable salt" are used interchangeably herein to refer to a salt which is toxicologically safe for human and animal administration. This salt may be selected from a group including hydrochlorides, hydrobromides, hydroiodides, sulfates, bisulfates, nitrates, citrates, tartrates, bitartrates, phosphates, malates, maleates, napsylates, fumarates, succinates, acetates, terephthalates, pamoates and pectinates. Pharmaceutically acceptable salts include both the metallic (inorganic) salts and organic salts; a non-exhaustive list of which is given in Remington's Pharmaceutical Sciences 17th Edition, pg. 1418 (1985). It is well known to one skilled in the art that an appropriate salt form is chosen based on physical and chemical stability, flowability, hydroscopicity and solubility.

"Phenylalkyl" means alkyl as defined above which is substituted with phenyl, e.g., —$CH_2$phenyl, —$(CH_2)_2$phenyl, —$(CH_2)_3$phenyl, $CH_3CH(CH_3)CH_2$phenyl, and the like and derivatives thereof. Phenylalkyl is a subset of the aralkyl group.

The terms "polynucleotide variant" and "variant" refer to polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally occurring amino acid polymers.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

The term "prodrug" is used in its broadest sense and encompasses those compounds that are converted in vivo to an $AT_2$ receptor antagonist according to the invention. Such compounds would readily occur to those of skill in the art, and include, for example, compounds where a free hydroxy group is converted into an ester derivative.

As used herein, "pseudohalides" are groups that behave substantially similar to halides. Such groups can be used in the same manner and treated in the same manner as halides (X, in which X is a halogen, such as Cl or Br). Pseudohalides include, but are not limited to cyanide, cyanate, thiocyanate, selenocyanate, trifluoromethyl and azide.

The terms "subject" or "individual" or "patient", used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment or prophylaxis for a neuropathic condition. However, it will be understood that the aforementioned terms do not imply that symptoms are present.

"Stereoisomers" refer to any two or more isomers that have the same molecular constitution and differ only in the three dimensional arrangement of their atomic groupings in space. Stereoisomers may be diastereoisomers or enantiomers. It will be recognized that the compounds described herein may possess asymmetric centers and are therefore capable of existing in more than one stereoisomeric form. The invention thus also relates to compounds in substantially pure isomeric form at one or more asymmetric centers e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

The term "substituted" and variants such as "optionally substituted" as used herein, unless otherwise indicated, mean that a substituent may be further substituted by one or more additional substituents, which may be optional or otherwise. Examples of additional substituents include $C_1$-$C_{10}$alkyl, $C_3$-$C_{10}$alkenyl, $C_3$-$C_{10}$alkynyl, aryl, —($C_1$-$C_4$alkyl)aryl, heterocyclyl, heteroaryl, $C_3$-$C_7$-cycloalkyl, $C_1$-$C_4$-perfluoroalkyl, —OH, —SH, —$HN_2$, nitrile, $C_1$-$C_{10}$-alkoxy, halo$C_{1-4}$ alkyl, hydroxy$C_{1-4}$alkyl, $C_1$-$C_{10}$-alkylthio, —$CF_3$, halo (F, Cl, Br, I), —$NO_2$, —$CO_2R^{23}$, —$NH_2$, $C_1$-$C_4$alkylamino, $C_1$-$C_4$dialkylamino, arylamino, diarylamino, aryl$C_{1-4}$alkylamino, aryl$C_{1-4}$dialkylamino, aryloxy, aryl$C_{1-4}$alkyloxy, formyl, $C_{1-10}$alkylcarbonyl and $C_{1-10}$alkoxycarbonyl, —$PO_3H_2$, —$CO_2H$, —$CONHSO_2R^{21}$, —$CONHSO_2NHR^{20}$, —$NHCONHSO_2R^{21}$, —$NHSO_2R^{21}$, —$NHSO_2NHCOR^{21}$, —$SO_2NHR^{20}$, —$SO_2NHCOR^{21}$, —$SO_2NHCONHR^{20}$, —$SO_2NHCO_2R^{21}$, tetrazolyl, —CHO, —$CONH_2$, —NHCHO, —CO—($C_1$-$C_6$ perfluoroalkyl), —S(O), —($C_1$-$C_6$ perfluoroalkyl), wherein $R^{20}$ is H, $C_1$-$C_5$-alkyl, aryl, —($C_1$-$C_4$-alkyl)-aryl, heteroaryl; $R^{21}$ is aryl, $C_3$-$C_7$-cycloalkyl, $C_1$-$C_4$-perfluoroalkyl, $C_1$-$C_4$alkyl, optionally substituted with a substituent selected from the group consisting of aryl, heteroaryl, —OH, —SH, $C_1$-$C_4$-alkyl, $C_1$-$C_4$alkoxy, $C_1$-$C_4$alkylthio, —$CF_3$, halo, —$NO_2$, —$CO_2R^{23}$, $C_1$-$C_4$-alkylamino, $C_1$-$C_4$-dialkylamino, —$PO_3H_2$, or heteroaryl; and $R^{22}$ is selected from $C_1$-$C_6$-alkyl, $C_3$-$C_6$-cycloalkyl, aryl, —($C_1$-$C_5$-alkyl)-aryl, or heteroaryl.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

2. Abbreviations

The following abbreviations are used throughout the application:
d=day
h=hour
s=seconds
i.v.=intravenous
i.p.=intraperitoneal
s.c.=subcutaneous
STZ=streptozotocin
CCI=chronic constriction injury 3. Compositions and Methods for the Treatment or Prophylaxis of Neuropathic Conditions The present invention arises from the unexpected discovery that $AT_2$ receptor antagonists are effective in the prevention or attenuation of the painful symptoms of neuropathic conditions including primary and secondary neuropathic conditions. These discoveries are based on pre-clinical data which show that administration of various $AT_2$ receptor antagonists to rats with a mechanical nerve injury involving a chronic constriction injury to the sciatic nerve (CCI-rats) or to STZ-diabetic rats causes a dose-dependent attenuation in the development of tactile (mechanical) allodynia, the defining symptom of neuropathic pain. Accordingly, the present invention provides methods for treating or preventing neuropathic conditions, wherein the methods generally comprise administering to an individual having, or at risk of developing, a neuropathic condition, an effective amount of an $AT_2$ receptor antagonist, which is suitably in the form of a pharmaceutical composition. In accordance with the present invention, the $AT_2$ receptor antagonist can act to prevent or attenuate one or more symptoms associated with neuropathic conditions including, but not limited to, hyperesthesia, hyperalgesia, allodynia and/or spontaneous burning pain. In some embodiments, the $AT_2$ receptor antagonist is used to prevent or attenuate one or more symptoms associated with peripheral neuropathic conditions, illustrative examples of which include numbness, weakness, burning pain, shooting pain, and loss of reflexes. The pain may be severe and disabling. In some embodiments, the symptom, which is the subject of the prevention and/or attenuation, is pain. Accordingly, in a related aspect, the invention provides methods for preventing and/or attenuating neuropathic pain in an individual, comprising administering to the individual a pain-preventing or -attenuating effective amount of an $AT_2$ receptor antagonist, which is suitably in the form of a pharmaceutical composition.

There are many possible causes of neuropathy and it will be understood that the present invention contemplates the treatment or prevention of any neuropathic condition regardless of the cause. In some embodiments, the neuropathic conditions are a result of diseases of the nerves (primary neuropathy) and neuropathy that is caused by systemic disease (secondary neuropathy) such as but not limited to: diabetic neuropathy; Herpes Zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tumaculous neuropathy; neuropathy caused by nutritional deficiency and neuropathy caused by kidney failure. Other causes include repetitive activities such as typing or working on an assembly line, medications known to cause peripheral neuropathy such as several antiretroviral drugs (ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barre syndrome). In certain embodiments, the neuropathic condition is a peripheral neuropathic condition, which is suitably pain secondary to mechanical nerve injury or painful diabetic neuropathy (PDN) or related condition.

The neuropathic condition may be acute or chronic and, in this connection, it will be understood by persons of skill in the art that the time course of a neuropathy will vary, based on its underlying cause. With trauma, the onset of symptoms may be acute, or sudden; however, the most severe symptoms may develop over time and persist for years. Inflammatory and some metabolic neuropathies have a subacute course extending over days to weeks. A chronic course over weeks to months usually indicates a toxic or metabolic neuropathy. A chronic, slowly progressive neuropathy over many years such as occurs with painful diabetic neuropathy or with most hereditary neuropathies or with a condition termed chronic inflammatory demyelinating polyradiculoneuropathy (CIDP). Neuropathic conditions with symptoms that relapse and remit include the Guillian-Barre syndrome.

The $AT_2$ receptor antagonist includes and encompasses any active compound that binds to the $AT_2$ receptor subtype and that suitably inhibits the effect of angiotensin II signaling through this receptor, including pharmaceutical compatible salts of the active compound. This category includes compounds having differing structural features. For example, in some embodiments, the $AT_2$ receptor antagonist is selected from the compounds listed in U.S. Pat. No. 5,798,415 and especially in the compound claims of this patent. In illustrative examples of this type, the $AT_2$ receptor antagonist is selected from compounds having the formula (Ia):

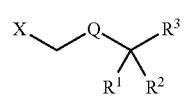

(Ia)

or their pharmaceutically compatible salts,
wherein:
Q is naphthyl, a 5 to 7 member heterocycle having from 1 to 3 atoms independently selected from nitrogen, oxygen and sulfur, or an 8 to 11 member heterobicycle having from 1 to 4 atoms selected from nitrogen, oxygen and sulfur, said heterocycle or heterobicycle being saturated, partially saturated or unsaturated and said naphthyl, heterocycle or heterobicycle optionally substituted with 1 to 4 $W^1$ substituents;

each $W^1$ substituent is independently selected from halo, hydroxy, nitro, cyano, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl, $C_1$ to $C_7$ alkylsulfonyl, —CONRR, —COOR and phenyl, said alkyl, cycloalkyl, alkoxy, alkylamino, dialkylamino, alkylthio, alkylsulfinyl and alkylsulfonyl optionally substituted with 1 or more $W^2$ substituents, and said phenyl optionally substituted with 1 or more $W^3$ substituents;

each R is independently hydrogen or $C_1$ to $C_8$ alkyl, said alkyl optionally substituted with 1 or more $W^2$ substituents;

each $W^2$ substituent is independently selected from halo, hydroxy, oxo, $C_3$ to $C_7$ cycloalkyl, $C_1$ to $C_7$ alkoxy, acyloxy, phenyl and 5 to 7 member heterocycle having 1 to 3 atoms selected from nitrogen, oxygen and sulfur, said phenyl and heterocycle optionally substituted with 1 or more $W^3$ substituents;

each $W^3$ substituent is independently selected from halo, hydroxy, nitro, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl and $C_1$ to $C_7$ alkylsulfonyl;

$R^1$ and $R^2$, when taken separately, are each independently selected from hydrogen, hydroxy, $C_1$ to $C_{10}$ alkyl, $C_1$ to $C_7$ alkylthio, $C_1$ to $C_7$ alkylsulfinyl, $C_1$ to $C_7$ alkylsulfonyl, phenyl and 5 to 7 member heterocycle or 8 to 11 member heterobicycle, having 1 to 3 atoms selected from nitrogen, oxygen and sulfur, said alkyl, alkylthio, alkylsulfinyl and alkylsulfonyl optionally substituted with 1 or more $W^4$ substituents, said phenyl and said heterocycle and heterobicycle optionally substituted with 1 to 5 $W^3$ substituents, wherein the $W^3$ substituents are as defined above, and said heterocycle being saturated, partially saturated or unsaturated, provided that $R^1$ and $R^2$ are not both hydroxy;

$R^1$ and $R^2$, when taken together with the carbon atom to which they are attached, form a $C_3$ to $C_7$ carbocyclic, $C_7$ to $C_{11}$ carbobicyclic, 3 to 7 member heterocyclic group having from 1 to 3 atoms independently selected from nitrogen, oxygen and sulfur, or a 7 to 11 member heterobicyclic group having from 1 to 4 atoms independently selected from nitrogen, oxygen and sulfur, said carbocyclic, carbobicyclic, heterocyclic or heterobicyclic group being saturated, partially saturated or unsaturated and optionally substituted with 1 or more $W^5$ substituents;

each $W^4$ substituent is independently selected from halo, $C_3$ to $C_8$ cycloalkyl, phenyl and 5 to 7 member heterocycle having 1 to 3 atoms selected from nitrogen, oxygen and sulfur, said phenyl and heterocycle optionally substituted with 1 or more substituents independently selected from halo, hydroxy, nitro, $C_1$ to $C_{10}$ alkyl, $C_3$ to $C_7$ cycloalkyl, $C_1$ to $C_7$ alkoxy, amino, $C_1$ to $C_7$ alkylamino and di($C_1$ to $C_7$ alkyl)amino;

each $W^5$ substituent is independently selected from halo, hydroxy, nitro, cyano, oxo, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl, $C_1$ to $C_7$ alkylsulfonyl, —CONRR, —COOR and phenyl, said alkyl, cycloalkyl, alkoxy, alkylamino, dialkylamino, alkylthio, alkylsulfinyl and alkylsulfonyl groups optionally substituted with 1 or more $W^2$ substituents, and said phenyl optionally substituted with 1 or more $W^3$ substituents, wherein the $W^3$ substituents are as defined above;

$R^3$ is —$(CH_2)_n COR^4$, tetrazolyl, $C_1$ to $C_5$ alkyltetrazolyl, triazolyl, $C_1$ to $C_5$ alkyltriazolyl, —$(CH_2)_n CH_2OH$, —$SO_2R^4$, —$SO_2NR^5R^6$ or —$NHSO_2R^7$;

$R^4$ is hydrogen, hydroxy, —$NHSO_2R^7$, $C_1$ to $C_{10}$ alkoxy, $C_1$ to $C_7$ alkylthio, —$NR^5R^6$, —$NHSO_2R^7$ or —OY, said alkoxy and alkylthio groups optionally substituted with 1 or more $W^6$ substituents;

n is an integer from 0 to 5;

Y is a pharmaceutically acceptable cation or a group hydrolyzable under physiological conditions;

$R^5$ and $R^6$, when taken separately, are each independently hydrogen, hydroxy, cyano, $C_1$ to $C_{10}$ alkyl, $C_1$ to $C_8$ alkoxy, —COR, —CONRR, —COOR, phenoxy, —CO($C_6H_5$) or 5 to 6 member heterocycle having 1 to 4 atoms selected from nitrogen, oxygen and sulfur, wherein R is as defined above, said alkyl optionally substituted with 1 or more $W^3$ substituents, wherein the $W^3$ substituents are as defined above, said —CO($C_6H_5$) optionally substituted with 1 to 3 $W^6$ substituents and said heterocycle optionally substituted with 1 or more $W^5$ substituents, wherein the $W^5$ substituents are as defined above;

$R^5$ and $R^6$, when taken together with the nitrogen atom to which they are attached, form a 3 to 7 member ring having 1 to 3 nitrogen atoms and from 0 to 3 atoms selected from oxygen and sulfur, said ring being saturated, partially saturated or unsaturated and optionally substituted with 1 or more $W^1$ substituents, wherein the $W^1$ substituents are as defined above;

$R^7$ is $C_1$ to $C_{10}$ alkyl or phenyl, said alkyl optionally substituted with 1 or more $W^6$ substituents, and said phenyl optionally substituted with 1 or more $W^3$ substituents, wherein the $W^3$ substituents are as defined above;

X is an azacyclic group of the formula:

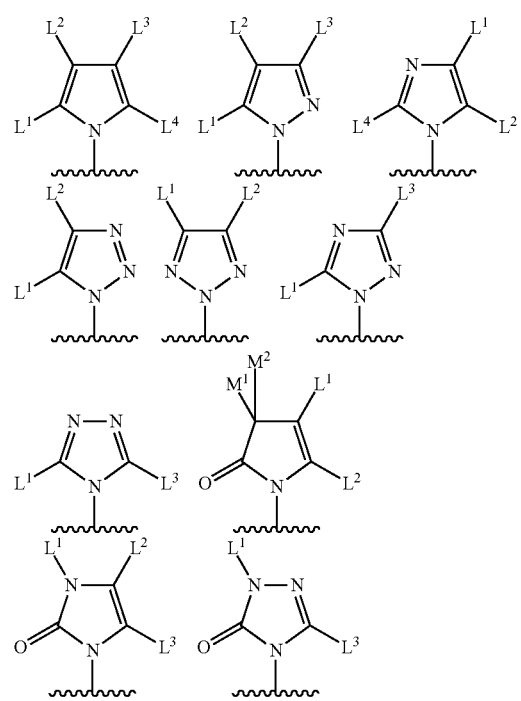

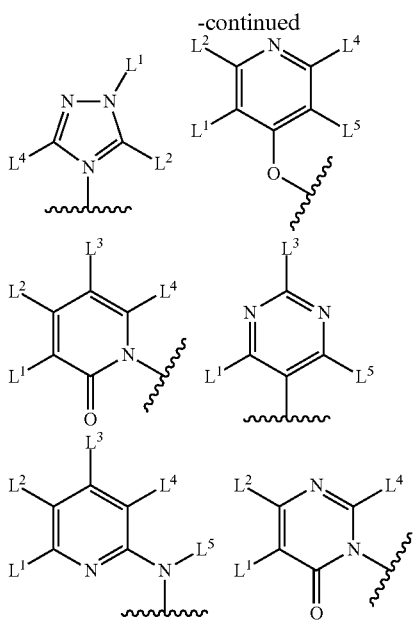

$L^1$, $L^2$, $L^3$, $L^4$ and $L^5$, when taken separately, are independently hydrogen, halo, nitro, $C_1$ to $C_9$ alkyl, $C_3$ to $C_7$ cycloalkyl, polyfluoro-$C_1$ to $C_4$ alkyl, aryl, heteroaryl, tetrazol-5-yl, —$COR^8$, —$CO_2R^8$, —$CONHSO_2R^9$, —$CONR^{10}R^{10}$, —$CONH$(tetrazol-5-yl), —$OR^9$, —$COCNR^9R^{11}$, —$NR^8R^9$, —$NHCOR^9$, —$NHCO_2R^9$, —$NHCONR^8R^9$, —$NHSO_2R^9$, —$NHSO_2NR^9R^{11}$, —$NHSO_2$-polyfluorophenyl, —$SR^9$, —$SOR^9$, —$SO_2R^9$, —$SO^2NHCN$, —$SO^2NR^{11}R^{12}$, —$SO_2NHCOR^9$, —$SO_2NH$-heteroaryl, —$PO(OR^8)_2$ or —$PO(OR^8)R^{11}$, said alkyl, cycloalkyl, aryl and heteroaryl groups optionally substituted with 1 or more substituents selected from hydroxy, halo, $C_1$ to $C_4$ perfluoroalkyl, $C_1$ to $C_4$ alkoxy, aryl, heteroaryl, guanidino, morpholino, tetrazol-5-yl, —$COR^8$, —$CO_2R^8$, —$CONHSO_2R^9$, —$CONR^8R^8$, —O—$COR^8$, —$NR^8R^8$, —$NR^{12}COOR^9$, —N($C_1$ to $C_6$ alkyl)piperazine, —$SR^9$, —$SOR^9$, —$SO_2R^9$, —$SO_2NR^8CN$, —$SO_2NR^8COR^9$, —$SO_2NR^8$-heteroaryl, —$PO(OR^8)_2$ and —$PO(OR^8)R^{13}$;

$L^1$ and $L^2$, $L^2$ and $L^3$, $L^3$ and $L^4$ or $L^4$ and $L^5$, when taken together with the azacyclic group to which they are attached, form a fused 8 to 11 member azabicyclic system having 1 to 5 nitrogen atoms and 0 to 3 atoms selected from oxygen and sulfur, said azabicyclic system optionally substituted with 1 to 3 $W^6$ substituents;

each $W^6$ substituent is independently halo, nitro, cyano, $C_1$ to $C_6$ alkyl, $C_3$ to $C_7$ cycloalkyl, polyfluoro-$C_1$ to $C_4$ alkyl, aryl, heteroaryl, tetrazol-5-yl, —$COR^8$, —$CO_2R^8$, —$CONR^8SO_2R^9$, —$CONR^9R^{10}$, —$CONR^8$(tetrazol-5-yl), —$OR^9$, —$OCONR^9R^{11}$, —$NR^8R^9$, —$NR^8COR^9$, —$NR^8COR^9$—$NR^8CONR^8R^9$, —$NR^8SO_2R^9$, —$NR^8SO_2NR_9R^{11}$, —$NR^8SO_2$-polyfluorophenyl, —$SR^9$, —$SOR^9$, —$SO_2R^9$, —$SO_2NR_8CN$, —$SO_2NR^9R^{12}$, —SO $NR^8COR^9$, —$SO_2NR^8$-heteroaryl, —$PO(OR^8)_2$ or —$PO(OR^8)R^{11}$, said alkyl, cycloalkyl, aryl and heteroaryl groups optionally substituted with 1 or more substituents selected from hydroxy, halo, $C_1$ to $C_4$ perfluoroalkyl, $C_1$ to $C_4$ alkoxy, aryl, heteroaryl, guanidino, morpholino, tetrazol-5-yl, —$COR^8$, —$CO_2R^8$, —$CONR^8SO_2R^9$, —$CONR^8$, $R^9$, —O—$COR^8$, —$NR^8$, $R^9$, —$NR^{12}COOR^9$, —N($C_1$ to $C_6$ alkyl)piperazine, —$SR^9$, —$SOR^9$, —$SO_2R^9$, —$SO_2NR^8CN$, —$SO_2NR^8COR^9$, —$SO_2NR^8$-heteroaryl, —$PO(OR^8)_2$ and —$PO(OR^8)R^{13}$;

each $R^8$ is independently hydrogen, $C_1$ to $C_6$ alkyl, $C_3$ to $C_7$ cycloalkyl, aryl, heteroaryl or aryl($C_1$ to $C_6$)alkyl;

each $R^9$ is independently hydrogen, $C_1$ to $C_{10}$ alkyl, $C_3$ to $C_7$ cycloalkyl, aryl, heteroaryl or polyfluoro($C_1$ to $C_4$)alkyl, said alkyl and cycloalkyl optionally substituted with 1 or more substituents selected from halo, hydroxy, nitro, $C_1$ to $C_4$ alkoxy, $C_1$ to $C_4$ alkylthio, —$CO_2R^{12}$, amino, $C_1$ to $C_4$ alkylamino, di($C_1$ to $C_4$)alkylamino, aryl, heteroaryl, —SH, —$PO_3H_2$, —P(O)(OH)(O—$C_1$ to $C_4$ alkyl), P(O)($OR^8$)($R^{11}$) or P(O)($OR^{14}$)($R^{15}$);

each $R^{11}$ is independently hydrogen, $C_1$ to $C_5$ alkyl, aryl or —$CH_2$-aryl;

each $R_{11}$ is independently hydrogen, $C_1$ to $C_5$ alkyl, $C_3$ to $C_7$ cycloalkyl, aryl or —$C_{1-12}$-aryl;

each $R^{12}$ is hydrogen or $C_1$ to $C_4$ alkyl;

each $R^{13}$ is independently hydrogen, $C_1$ to $C_5$ alkyl, $C_1$ to $C_4$ alkenyl, $C_1$ to $C_4$ alkoxy($C_1$ to $C_4$)alkyl or benzyl, said benzyl optionally substituted with 1 or more substituents independently selected from hydroxy, amino, nitro and methoxy;

$R^{14}$ and $R^{15}$ are taken together and form a 5 to 7 member ring having 1 to 3 atoms independently selected from nitrogen, oxygen and sulfur;

$M^1$ and $M^2$ are taken together and are —$(CH_2)_m$; and m is an integer from 3 to 7.

Preferred compounds are those of formula (I) wherein:

X is

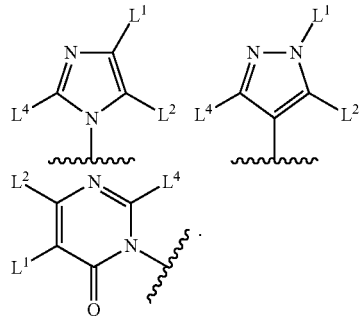

$L^1$, $L^2$ and $L^4$ are as defined above;

Q is thiophene, pyridine, pyrimidine, naphthyl, benzofuran or any of the foregoing substituted with 1 or 2 $W^1$ substituents; $R^1$ and $R^2$ are taken together as defined above;

$R^3$ is —$(CH_2)_n$ $COR^4$; n is 0 or 1; $R^4$ is hydrogen, hydroxy or —OY;

Y is a pharmaceutically acceptable cation or a group hydrolyzable under physiological conditions; and each $W^1$ is independently halo, hydroxy, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, —CONRR or —COOR, wherein R is as defined above.

Particularly preferred are those compounds wherein X, Q, $R^3$, $R^4$, n and Y are as defined immediately above and wherein:

$R^1$ and $R^2$ are taken together and form a $C_5$ to $C_6$ carbocyclic, $C_8$ to $C_{10}$ carbobicyclic or 5 to 7 member heterocyclic group having 1 or 2 atoms independently selected from nitrogen, oxygen and sulfur, said carbocyclic, carbobicyclic or heterocyclic group being saturated, partially saturated or unsaturated;

$L^1$ and $L^2$, when taken separately, are each independently hydrogen, halo, $C_1$ to $C_6$ alkyl, $C_3$ to $C_7$ cycloalkyl, polyfluoro-$C_1$ to $C_4$ alkyl or —$CO_2R^8$;

$L^1$ and $L^2$, when taken together with the azacyclic group to which they are attached, form a fused 8 to 10 member azabicyclic system having 2 to 4 nitrogen atoms, said azabicyclic system optionally substituted with 1 to 3 $W^6$ substituents;

$L^4$ is $C_1$ to $C_4$ alkyl, $C_3$ to $C_5$ cycloalkyl or $C_1$ to $C_3$ alkoxy;

$R^8$ is hydrogen, $C_1$ to $C_6$ alkyl or $C_3$ to $C_7$ cycloalkyl; and each $W^6$ is independently halo, $C_1$ to $C_6$ alkyl, $C_3$ to $C_7$ cycloalkyl, polyfluoro-$C_1$ to $C_4$ alkyl, —$CO_2R^8$, amino, $C_1$ to $C_6$ alkylamino, di($C_1$ to $C_6$)alkylamino, acylamino or diacylamino.

Among the particularly preferred compounds defined above are those having the structure:

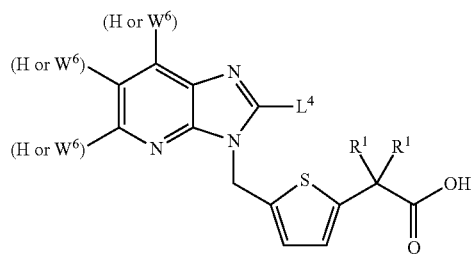

wherein:

L4 is $C_1$ to $C_4$ alkyl or $C_3$ to $C_5$ cycloalkyl;

each $W^6$ is independently $C_1$ to $C_6$ alkyl, amino, $C_1$ to $C_6$ alkylamino, di($C_1$ to $C_6$)alkylamino, acylamino or diacylamino; and $R^1$ and $R^2$ are taken together and form cyclopentane, cyclohexane, cyclopentane, tetrahydropyran or indan, for example:

1-[5-(2-ethyl-5,7-dimethylimidazo[4.5-b]pyridin-3-ylmethyl)thiophen-2-yl]-cyclopent-3-ene carboxylic acid;

1-[5-(5,7-dimethyl-2-propylimidazo[4.5-b]pyridin-3-ylmethyl)thiophen-2-yl]cyclopent-3-ene carboxylic acid;

1-[5-(2-cyclopropyl-5,7-dimethylimidazo[4.5-b]pyridin-3-ylmethyl)thiophen-2-yl]cyclopent-3-ene carboxylic acid;

1->5-(2-cyclopropyl-5,7-dimethylimidazo[4.5-b]pyridin-3-ylmethyl)thiophen-2-yl]cyclopentane carboxylic acid;

4-[5-(2-ethyl-5,7-dimethylimidazo[4.5-b]pyridin-3-ylmethyl)thiophen-2-yl]tetrahydropyran-4-carboxylic acid;

2-[5-(2-ethyl-5,7-dimethylimidazo[4.5-b]pyridin-3-ylmethyl)thiophen-2-yl]indan-2-carboxylic acid;

2-[5-(2-cyclopropyl-5,7-dimethylimidazo[4,5-b]pyridin-3-ylmethyl)thiophen-2-yl]indan-2-carboxylic acid;

1-[5-(2-ethyl-5,7-dimethylimidazo[4,5-b]pyridin-3-ylmethyl)thiophen-2-yl]cyclohexane carboxylic acid; and 1-[5-(2-cyclopropyl-5,7-dimethylimidazo[4.5-b]pyridin-3-ylmethyl)thiophen-2-yl]cyclohexane carboxylic acid.

Also among the particularly preferred compounds defined above are those having the structure

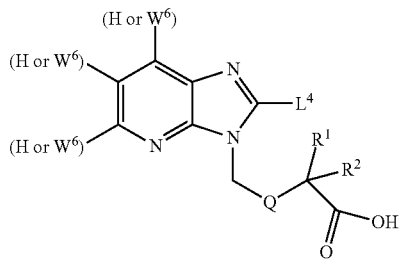

wherein:

Q is

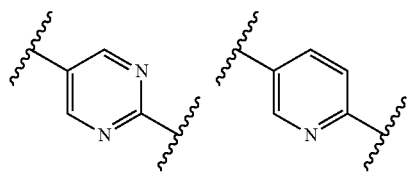

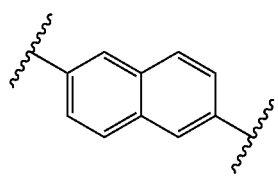

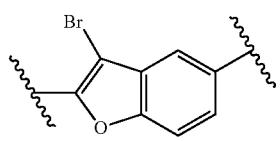

$L^4$ is $C_1$ to $C_4$ alkyl or $C_3$ to $C_5$ cycloalkyl; and $R^1$ and $R^2$ are taken together and are —$CH_2CH_2CH_2CH_2$— or —$CH_2CH$=$CHCH_2$—, for example:

1-[5-(2-ethyl-5,7-dimethylimidaz[4.5-b]pyridin-3-ylmethyl)pyridin-2-yl]cyclopentane carboxylic acid;

1-[5-(2-cyclopropyl-5,7-dimethylimidazo[4.5-b]pyridin-3-ylmethyl)pyridin-2-yl]cyclopentane carboxylic acid;

1-[2-(2-ethyl-5,7-dimethylimidazo[4.5-b]pyridin-3-ylmethyl)pyrimidin-5-yl]cyclopent-3-ene carboxylic acid;

1-[2-(2-cyclopropyl-5,7-dimethylimidazo[4.5-b]pyridin-3-ylmethyl)pyrimidin-5-yl]cyclopent-3-ene carboxylic acid;

1-[6-(2-ethyl-5,7-dimethylimidazo[4.5-b]pyridin-3-ylmethyl)naphthalen-2-yl]cyclopent-3-ene carboxylic acid; and 1-[3-bromo-5-(2-ethyl-5,7-dimethylimidazo[4.5-b]pyridin-3-ylmethyl)benzofuran-2-yl]cyclopentane carboxylic acid.

Also among the particularly preferred compounds defined above are those having the structure

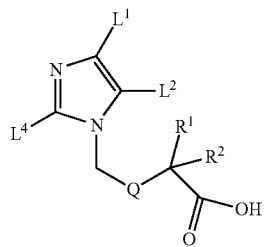

wherein:

Q is

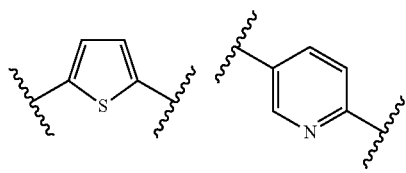 [SMILES: *c1ccc(*)s1 ; *c1ccc(*)nc1]

$L^1$ and $L^2$ are taken separately and are each independently halo, $C_1$ to $C_6$ alkyl or —$CO_2H$;

$L^4$ is $C_1$ to $C_4$ alkyl; and $R^1$ and $R^2$ are taken together and are —$CH_2CH_2CH_2CH_2$— or —$CH_2CH$=$CHCH_2$—, for example:

2-butyl-3-[5-(1-carboxycyclopent-3-enyl)thiophen-2-ylmethyl]-5-chloro-3H-imidazole-4-carboxylic acid;

3-[5-(1-carboxycyclopent-3-enyl)thiophen-2-ylmethyl]-5-ethyl-2-propyl-3H-imidazole-4-carboxylic acid; and 3-[5-(1-carboxycyclopent-3-enyl)thiophen-2-ylmethyl]-5-chloro-2-propyl-3H-imidazole-4-carboxylic acid.

Also among the particularly preferred compounds defined above are those having the structure

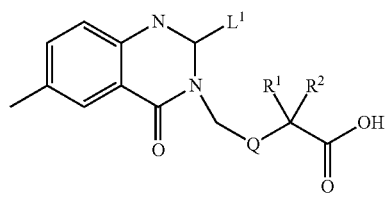

wherein:

Q is

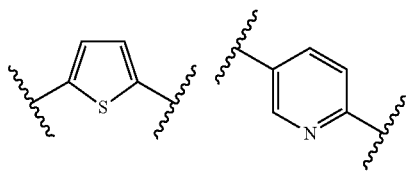 [SMILES: *c1ccc(*)s1 ; *c1ccc(*)nc1]

$L^4$ is $C_1$ to $C_4$ alkyl; and $R^1$ and $R^2$ are taken together and are —$CH_2CH_2CH_2CH_2$— or —$CH_2CH$=$CHCH_2$—, for example:

1-[5-(2-butyl-5-methyl-4-oxo-4H-quinazolin-3-ylmethyl)pyridin-2-yl]cyclopentane carboxylic acid; and 1-[5-(2-butyl-5-methyl-4-oxo-4H-quinazolin-3-ylmethyl)thiophen-2-yl]cyclopent-3-ene carboxylic acid.

Also among the particularly preferred compounds defined above are those having the structure

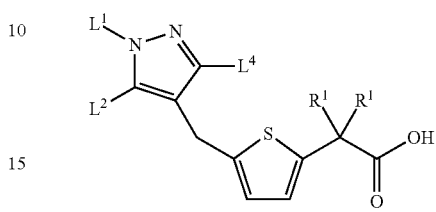

wherein:

$L^1$ and $L^2$ are taken separately and are each independently halo, $C_1$ to $C_6$ alkyl, polyfluoro-$C_1$ to $C_6$ alkyl or —$CO_2H$;

$L^4$ is $C_1$ to $C_4$ alkyl; and $R^1$ and $R_2$ are taken together and are —$CH_2CH_2CH_2CH_2$— or —$CH_2CH$=$CHCH_2$—, for example:

2,5-dibutyl-4-[5-(1-carboxycyclopent-3-enyl)thiophen-2-ylmethyl]-2H-pyrazole-3-carboxylic acid;

5-butyl-4-[5-(1-carboxycyclopent-3-enyl)thiophen-2-ylmethyl]-2-trifluoromethyl-2H-pyrazole-3-carboxylic acid; and 5-butyl-4-[5-(1-carboxycyclopent-3-enyl)thiophen-2-ylmethyl]-2-propyl-2 H-pyrazole-3-carboxylic acid.

Other preferred compounds include compounds in the same general class as:

1-[5-(2-cyclopropyl-5,7-dimethylimidazo[4.5-b]pyridin-3-ylmethyl)thiophen-2-yl]cyclopenten-3-ene carboxylic acid benzenesulfonamide;

1-[5-(2-cyclopropyl-5,7-dimethylimidazo[4.5-b]pyridin-3-ylmethyl)thiophen-2-yl]cyclopenten-3-ene carboxylic acid p-toluenesulfonamide;

1-[5-(2-cyclopropyl-5,7-dimethylimidazo[4.5-b]pyridin-3-ylmethyl)thiophen-2-yl]cyclopenten-3-ene carboxylic acid methanesulfonamide; and 1-[5-(2-cyclopropyl-5,7-dimethylimidazo[4.5-b]pyridin-3-ylmethyl)thiophen-2-yl]cyclopenten-3-ene carboxylic acid trifluoromethanesulfonamide.

Various intermediates also fall within the scope of the present invention, including:

1-thiophen-2-yl-cyclopent-3-ene carboxylic acid ethyl ester;

1-(5-formylthiophen-2-yl)cyclopent-3-ene carboxylic acid ethyl ester;

1-(5-chloromethylthiophen-2-yl)cyclopent-3-ene carboxylic acid ethyl ester; and

1-[5-(2-ethyl-5,7-dimethylimidazo>4,5-b!pyridin-3-ylmethyl)thiophen-2-yl!cyclopent-3-ene carboxylic acid ethyl ester.

In other embodiments, the $AT_2$ receptor antagonist is selected from the disubstituted 6-aminoquinazolinone compounds listed in U.S. Pat. No. 5,385,894 and especially in the compound claims of this patent. Representative examples of such compounds are represented by the formula (IIa):

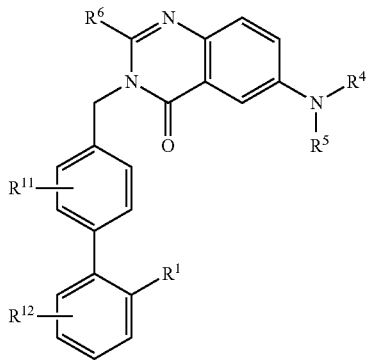

or a pharmaceutically compatible salt thereof, wherein:

$R^1$ is
(a) $CO_2R^2$,
(b) tetrazol-5-yl,
(c) $NHSO_2CF_3$,
(d) $SO_2NHCOR^3$, or
(e) $SO_2NH$-heteroaryl;

$R^2$ is
(a) hydrogen, or
(b) $C_1$-$C_6$ alkyl;

$R^3$ is
(a) $C_1$-$C_6$ alkyl,
(b) $C_3$-$C_7$ cycloalkyl,
(c) phenyl,
(d) substituted phenyl in which the substituent is F, Cl, Br, $C_1$-$C_4$ alkoxy, perfluoro $C_1$-$C_4$ alkyl, di-($C_1$-$C_4$-alkyl)amino, or $CO_2R^2$,
(e) substituted $C_1$-$C_8$ alkyl in which the substituent is $C_3$-$C_7$ cycloalkyl, $C_1$-$C_4$ alkoxy, hydroxy, di-($C_1$-$C_4$ alkyl)amino, $CO_2R_2$, morpholinyl, $C_1$-$C_4$ alkylpiperazinyl, $CF_3$, thio, $C_1$-$C_4$ alkylsulfinyl, $C_1$-$C_4$ alkylsulfonyl, heteroaryl, $NH_2$, or aryl, or
(f) heteroaryl;

$R^4$ is
(a) $C_1$-$C_6$ alkyl,
(b) substituted $C_1$-$C_6$ alkyl in which the substituent is $C_3$-$C_7$ cycloalkyl, alkoxy, hydroxy, alkyl)amino, $CO_2R_2$, morpholinyl, $C_1$-$C_4$ alkylpiperazinyl, $CF_3$, $C_1$-$C_4$ alkylthio, $C_1$-$C_4$ alkylsulfinyl, $C_1$-$C_4$ alkylsulfonyl, —CHO, $O(C_2$-$C_3$ alkyl-O—$)_n$ $C_1$-$C_3$ alkyl where n=1-5, or $NHCO_2(C_1$-$C_6$-alkyl).
(c) $C_2$-$C_6$ alkenyl,
(d) phenyl $C_1$-$C_6$ alkyl,
(e) substituted phenyl $C_1$-$C_6$ alkyl, in which the substituent on the phenyl group is hydroxy, $C_1$-$C_4$ alkoxy, F, Cl, I, Br, $NO_2$, cyano, $CO_2R^2$, di($C_1$-$C_4$ alkyl)amino, -Obenzyl, $CF_3$, phenyl-$C_1$-$C_4$-alkoxy, $C_1$-$C_4$ alkylthio, $C_1$-$C_4$-alkylsulfinyl, —OPO(O-benzyl)$_2$, or $C_1$-$C_4$ alkylsulfonyl, amino, P(O)(OH)$_2$, $C_1$-$C_4$ alkyl, —OPO(O—$C_1$-$C_6$ alkyl)$_2$, OPO(OH)$_2$, OCO(CH$_2$)$_2$COOH, OSO$_3$H, or O($C_2$-$C_3$ alkyl-O—$)_n$ $C_1$-$C_3$ alkyl,
(f) heteroaryl $C_1$-$C_6$ alkyl, or
(g) substituted heteroaryl $C_1$-$C_6$ alkyl, in which the substituent on the heteroaryl group is F, Cl, $NO_2$, $CO_2R^2$, or di-($C_1$-$C_4$ alkyl)amino;

$R^5$ is
(a) $CO_2R^7$,
(b) $CONR^8R^9$,
(c) $COR^{10}$,
(d) $SO^2NR^8R^9$, or
(e) $SO_2R^{10}$;

$R^6$ is
(a) $C_1$-$C_6$ alkyl,
(b) substituted $C_1$-$C_6$ alkyl in which the substituent is $C_3$-$C_7$ cycloalkyl, benzyl or $C_1$-$C_4$-alkoxy,
(c) cyclopropyl;

$R^7$ is
(a) $C_1$-$C_6$ alkyl,
(b) substituted $C_1$-$C_6$ alkyl in which the substituent is $C_1$-$C_4$ alkoxy, hydroxy, di($C_1$-$C_4$ alkyl)amino, $CO_2R^2$, morpholinyl, $C_1$-$C_4$ alkylpiperazinyl, $C_1$-$C_4$ alkylsulfinyl, $C_1$-$C_4$ alkylsulfonyl, or $O(C_2$-$C_3$ alkyl-O—$)_n$ $C_1$-$C_3$ alkyl,
(c) phenyl $C_1$-$C_6$ alkyl,
(d) substituted phenyl $C_1$-$C_6$ alkyl, in which the substituent on the phenyl group is hydroxy, $C_1$-$C_4$ alkoxy, F, Cl, $NO_2$, cyano, $CO_2R^2$, di($C_1$-$C_4$ alkyl)amino, $CF_3$, phenyl $C_1$-$C_4$ alkoxy, $C_1$-$C_4$ alkylthio, $C_1$-$C_4$ alkylsulfinyl, $C_1$-$C_4$ alkylsulfonyl, or $O(C_2$-$C_3$ alkyl-O—$)_n$ $C_1$-$C_3$ alkyl,
(e) heteroaryl $C_1$-$C_6$ alkyl, or
(f) substituted heteroaryl $C_1$-$C_6$ alkyl, in which the substituent on the heteroaryl group is F, Cl, $NO_2$, $CO_2R^2$, or di-($C_1$-$C_4$ alkyl)amino;

$R^8$ is
(a) hydrogen, or
(b) $C_1$-$C_6$ alkyl;

$R^9$ is
(a) $C_1$-$C_6$ alkyl, or
(b) substituted $C_1$-$C_6$ alkyl in which the substituent is $C_1$-$C_4$ alkoxy, hydroxy, di-($C_1$-$C_4$ alkyl)amino, $CO_2R^2$, morpholinyl, $C_1$-$C_4$ alkylpiperazinyl, $C_1$-$C_4$ alkylsulfinyl or $C_1$-$C_4$ alkylsulfonyl,
(c) perfluoro $C_1$-$C_6$ alkyl,
(d) phenyl,
(e) heteroaryl, or $R^8$ and $R^9$ taken together are morpholino,

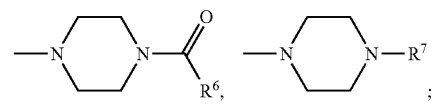

$R^{10}$ is
(a) phenyl,
(b) substituted phenyl in which the substituent is F, Cl, Br, I, $C_1$-$C_4$-alkoxy, $C_1$-$C_4$ alkyl, $NO_2$, cyano, $OC_6H_5$, $CO_2R_2$, di($C_1$-$C_4$ alkylamino), $CF_3$, $C_1$-$C_4$ alkylthio, $C_1$-$C_4$ alkylsulfinyl, $C_1$-$C_4$ alkylsulfonyl, —OPO($OC_1$-$C_6$-alkyl)$_2$, OPO(OH)$_2$, OPO(O-benzyl)$_2$, OCO(CH$_2$)$_2$ COOH, OSO$_2$OH, —PO($OC_1$-$C_6$-alkyl)$_2$, —PO(OH)$_2$, OBn, or O—($C_2$-$C_3$ alkyl-O)$_n$ $C_1$-$C_3$ alkyl,
(c) phenyl C1-C6 alkyl,
(d) heteroaryl,
(e) C1-C6 alkyl,
(f) substituted $C_1$-$C_6$ alkyl in which the substituent is $C_3$-$C_7$ cycloalkyl, $C_1$-$C_4$ alkoxy, hydroxy, di-($C_1$-$C_4$ alkyl)amino, $CO_2R^2$, morpholinyl, $C_4$ alkylpiperazinyl, $CF_3$, thio, $C_1$-$C_4$ alkylsulfinyl, $C_1$-$C_4$ alkylsulfonyl, imidazolyl, —N(COC1-C6 alkyl)piperazinyl, or N-aryl-piperazinyl (g) substituted phenyl $C_1$-$C_6$ alkyl, in which the substituent on the phenyl group is hydroxy, $C_1$-$C_4$ alkoxy, F, Cl, $NO_2$, cyano, $CO_2R^2$, di($C_1$-$C_4$ alkyl)amino, $CF_3$, phenyl $C_1$-$C_4$ alkoxy, thio, $C_1$-$C_4$ alkylsulfinyl, or $C_1$-$C_4$-alkylsulfonyl, or (h) $C_3$-$C_7$ cycloalkyl.

$R^{11}$ is (a) hydrogen, (b) F, Cl, Br or I (c) $C_1$-$C_4$ alkyl, (d) $C_1$-$C_4$ alkoxy, $R^{12}$ is (a) hydrogen, (b) $C_1$-$C_5$ alkyl, (c) phenyl, (d) substituted phenyl in which the substituent is $C_1$-$C_4$ alkoxy, F, Cl, $CO_2R^2$, di($C_1$-$C_4$ alkyl)amino, thio, $C_1$-$C_4$ alkylsulfinyl, $C_1$-$C_4$ alkylsulfonyl.

In some of the above embodiments, the term heteroaryl means an unsubstituted, monosubstituted or disubstituted five or six membered aromatic ring which contains 1 to 3 heteroatoms selected from O, S, or N and the substituents are selected from the group consisting of $C_1$-$C_4$ alkyl, F, Cl, $CO_2R^2$, or di-($C_1$-$C_4$ alkyl)amino.

The abbreviations defined in the table below are used in the specific embodiments which are illustrated in tabular form:

| Table of Abbreviations | | | |
|---|---|---|---|
| Me | methyl | iPn | isopentyl |
| Et | ethyl | Hex | n-hexyl |
| Pr | n-propyl | cHex | cyclohexyl |
| iPr | isopropyl | Boc | butyloxycarbonyl |
| cPr | cyclopropyl | Ph | phenyl |
| Bu | n-butyl | Bn | benzyl |
| iBu | isobutyl | Bz | benzoyl |
| tBu | tertbutyl | TET | tetrazol-5-yl |
| Pn | n-pentyl | PIP | Piperazinyl |

In a first specific embodiment of the compounds according to formula (IIa), $R^5$ is $CO_2R^7$. One class of this embodiment is represented by the compounds of the formula (IIa) wherein:

$R^1$ is tetrazol-5-yl or $SO_2NHCOR^3$ or $NHSO_2CF_3$ $R^3$ is a) phenyl, b) substituted phenyl in which the substituent is F, Cl, Br, I or $C_1$-$C_4$ alkoxy, c) $C_1$-$C_8$ alkyl substituted with di-($C_1$-$C_4$-alkyl)amino or $NH_2$, or d) $C_3$-$C_7$-cycloalkyl;

$R^4$ is a) $C_2$-$C_6$ alkyl, b) substituted $C_2$-$C_6$ alkyl in which the substituent is: CHO, $CO_2C_1$-$C_4$ alkyl, $CO_2H$, $OC_1$-$C_4$ alkyl, cyclohexyl, phenyl, $NHCO_2tBu$, c) benzyl, d) substituted benzyl in which the substituent on the phenyl group is: F, Cl, Br, I, OH, $OPO(OC_1$-$C_4$ alkyl$)_2$, OPO(Obenzyl$)_2$, OPO(OH$)_2$, $—PO(OC_1$-$C_4$ alkyl$)_2$, $—PO$(Obenzyl$)_2$, OPO(OH$)_2$, $NO_2$, $NH_2$, $N(C_1$-$C_4$ alkyl$)_2$, Obenzyl, e) $CH_2$-heteroaryl or f) $C_3$-$C_6$ alkenyl;

$R^6$ is a) $C_1$-$C_6$ alkyl, b) substituted $C_1$-$C_6$ alkyl in which the substituent is: -benzyl, $—C_1$-$C_3$ alkyl, or $—OC_1$-$C_4$ alkyl, or c) cyclopropyl;

$R^7$ is a) $C_1$-$C_6$ alkyl, b) benzyl, c) $C_2$-$C_4$ alkyl-O—$C_1$-$C_4$ alkyl or d) phenyl;

$R^{11}$ and $R^{12}$ are hydrogen,

Illustrating the first class of this embodiment are the following compounds (with their Compound Number designation) of the formula (IIa):

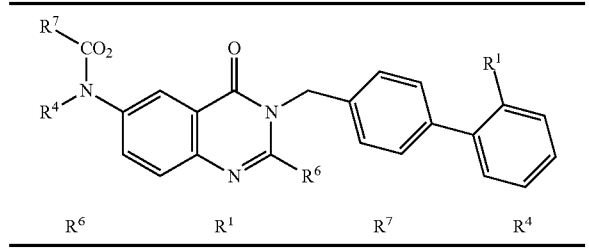

| $R^6$ | $R^1$ | $R^7$ | $R^4$ |
|---|---|---|---|
| Pr | TET | iBu | Et |
| Bu | TET | iBu | Bn |
| Bu | TET | tBu | Me |
| Pr | TET | iBu | Bu |
| Pr | TET | Et | Me |
| Pr | TET | iPr | Me |
| Pr | TET | Me | Me |
| Pr | TET | Bu | Me |
| Pr | TET | iBu | Pr |
| Pr | TET | iBu | Allyl |
| Pr | TET | iBu | Pn |
| Pr | TET | iBu | Pn |
| Pr | TET | iBu | $(CH_2)_3Ph$ |
| Pr | TET | Me | Bn |
| Pr | TET | iBu | Bn |
| Pr | TET | Pr | Bn |
| Pr | TET | Bu | Bn |
| Pr | TET | Bn | Bz |
| Pr | TET | Hex | Bn |
| Pr | TET | tBu | Bn |
| Pr | TET | $(CH_2)_2OMe$ | Bn |
| Pr | TET | Pr | $CH_2cHex$ |
| Pr | TET | Bu | Bu |
| Pr | TET | $(CH_2)_2OEt$ | $(CH_2)_2OMe$ |
| Et | TET | iBu | Me |
| Et | TET | iBu | Bn |
| iBu | TET | iBu | Me |
| iBu | TET | iBu | Bn |
| Me | TET | iBu | Bn |
| Me | TET | iBu | Me |
| Pr | $SO_2NHCOPh$ | iBu | Me |
| Pr | TET | Et | Bn |
| Pr | TET | Ph | $CH_2$-2-Pyr |
| Et | TET | tBu | Bn |
| Et | TET | Bn | Bn |
| Bu | $SO_2NHBz$ | iBu | Bn |
| Pr | $SO_2NHBz$ | Bu | Bn |
| Pr | $SO_2NHCOcPr$ | iBu | Bn |
| Pr | $SO_2NHCOcPr$ | iBu | Me |
| Pr | TET | Pr | $CH_2$-4-Pyr |
| Pr | TET | $(CH_2)_2OMe$ | Me |
| Pr | TET | Pr | $CH_2$-3-Pyr |
| Pr | TET | Pr | $CH_2$-2-Pyr |
| Pr | TET | $(CH_2)_2OMe$ | $CH_2$-4-Pyr |
| $CH_2OMe$ | TET | iBu | Me |
| $CH_2OMe$ | TET | Pr | $CH_2$-2-Pyr |
| Pr | $SO_2NHBz$ | Bn | Pn |
| Pr | TET | Et | $CH_2$-2-Pyr |
| Pr | TET | Pr | Bn-4-$NO_2$ |
| Pr | TET | Pr | Bn-4-$NH_2$ |

| $R^6$ | $R^1$ | $R^7$ | $R^4$ |
|---|---|---|---|
| Pr | TET | Pr | Bn-4-NMe$_2$ |
| H | TET | iBu | Me |

In a second specific embodiment of the compounds according to formula (IIa), $R^5$ is CONR$^8$R$^9$. One class of this embodiment is represented by the compounds of the formula (IIa) wherein:

$R^1$ is tetrazol-5-yl or SO$_2$NHCOR$^3$ or NHSO$_2$CF$_3$, $R^3$ is
 a) phenyl,
 b) substituted phenyl in which the substituent is F, Cl, Br, I or C$_1$-C$_4$ alkoxy,
 c) C$_1$-C$_8$ alkyl substituted with di-(C$_1$-C$_4$-alkyl)amino or NH$_2$, or
 d) C$_3$-C$_7$-cycloalkyl;

$R^4$ is
 a) C$_2$-C$_6$ alkyl,
 b) substituted C$_2$-C$_6$ alkyl in which the substituent is: CHO, CO$_2$C$_1$-C$_4$ alkyl, CO$_2$H, OC$_1$-C$_4$ alkyl, cyclohexyl, phenyl, or NHCO$_2$Bu,
 c) benzyl,
 d) substituted benzyl in which the substituent on the phenyl group is: F, Cl, Br, I, OH, OPO(OC$_1$-C$_4$ alkyl)$_2$, OPO(Obenzyl)$_2$, OPO(OH)$_2$, —PO(OC$_1$-C$_4$alkyl)$_2$, —PO(Obenzyl)$_2$, —OPO(OH)$_2$, NO$_2$, N(C$_1$-C$_4$ alkyl)$_2$, or Obenzyl,
 e) CH$_2$-heteroaryl, or
 f) C$_3$-C$_6$ alkenyl;

$R^6$ is
 a) C$_1$-C$_6$ alkyl,
 b) substituted C$_1$-C$_6$ alkyl in which the substituent is: -benzyl, —C$_1$-C$_3$ alkyl, or —OC$_1$-C$_4$ alkyl, or
 c) cyclopropyl;

$R^8$ is
 a) C$_1$-C$_6$ alkyl or
 b) hydrogen;

$R^9$ is
 a) C$_1$-C$_6$ alkyl, or
 b) when taken with R$^8$ and the nitrogen atom to which they are attached from a morpholinyl, N—(C$_1$-C$_6$ alkyl)piperazinyl, N—(COC$_1$-C$_6$ alkyl)piperazinyl, or N-arylpiperazinyl ring system, $R^{11}$ and $R^{12}$ are hydrogen.

Illustrating the first class of this second embodiment are the following compounds (with their Compound Number designation) of the formula (IIa):

| $R^6$ | $R^1$ | N(R$^8$)R$^9$ | $R^4$ |
|---|---|---|---|
| Bu | TET | N(Me)iPr | Me |
| Pr | TET | N(Pn)$_2$ | Me |
| Pr | TET | N(Me)Pr | Bn |
| Pr | TET | N(Me)Et | Bn |
| Pr | TET | morpholino | Bn |
| Et | TET | NHPr | Bn |
| Pr | TET | N(Me)iPr | Bn-4-F |
| Pr | TET | N(Me)iPr | CH$_2$-2-Pyr |

In a third specific embodiment of the compounds of the formula (IIa), $R^5$ is COR$^{10}$. One class of this embodiment is represented by the compounds of the formula (IIa) wherein:

$R^{11}$ is tetrazol-5-yl, SO$_2$NHCOR$^3$ or NHSO$_2$CF$_3$;

$R^3$ is
 a) phenyl,
 b) substituted phenyl in which the substituent is F, Cl, Br, I or C$_1$-C$_4$ alkoxy,
 c) C$_1$-C$_8$ alkyl substituted with di-(C$_1$-C$_4$ alkyl)amino or NH$_2$, or
 d) C$_3$-C$_7$-cycloalkyl;

$R^4$ is
 a) C$_2$-C$_6$ alkyl,
 b) substituted C$_2$-C$_6$ alkyl in which the substituent is: CHO, CO$_2$C$_1$-C$_4$ alkyl, CO$_2$H, OC$_1$-C$_4$ alkyl, cyclohexyl, phenyl, or NHCO$_2$tBu,
 c) benzyl,
 d) substituted benzyl in which the substituent on the phenyl group is: F, Cl, Br, I, OH, OPO(OC$_1$-C$_4$ alkyl)$_2$, OPO(Obenzyl)$_2$, OPO(OH)$_2$, —PO(OC$_1$-C$_4$ alkyl)$_2$, —PO(Obenzyl)$_2$, OPO(OH)$_2$, NO$_2$, NH$_2$, N(C$_1$-C$_4$ alkyl)$_2$, Obenzyl, OC$_1$-C$_4$ alkyl, COOH, or CO$_2$CH$_3$,
 e) CH$_2$-heteroaryl or
 f) C$_3$-C$_6$ alkenyl;

$R^6$ is
 a) C$_1$-C$_6$ alkyl,
 b) substituted C$_1$-C$_6$ alkyl in which the substituent is: -benzyl, —C$_1$-C$_3$ alkyl, or —OC$_1$-C$_4$ alkyl or
 c) cyclopropyl;

$R^{10}$) is
 (a) phenyl,
 (b) substituted phenyl in which the substituent is F, Cl, Br, I, methoxy, methyl, CF$_3$, SMe, SO$_2$Me, OH, OPO(O—C$_1$-C$_4$ alkyl)$_2$, OPO(OH)$_2$, OPO(OBn)$_2$, CO$_2$C$_1$-C$_4$ alkyl, COOH, Obenzyl or OC$_6$H$_5$,
 (c) benzyl,
 (d) heteroaryl,
 (e) C$_1$-C$_6$ alkyl or
 (f) substituted C$_1$-C$_6$ alkyl substituted with: imidazole, piperazine, morpholinyl, N—(C$_1$-C$_6$ alkyl)piperazinyl, N—(COC$_1$-C$_6$ alkyl)piperazinyl, or N-aryl-piperazinyl;

$R^{11}$ and $R^{12}$ are hydrogen.

Illustrating the first class of this third embodiment are the following compounds (with their Compound Number designation) of the formula (IIa):

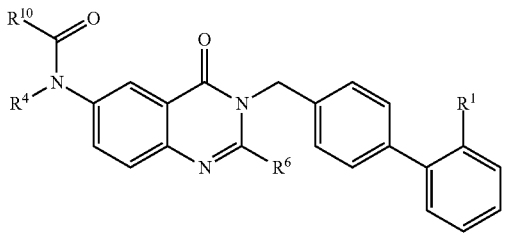
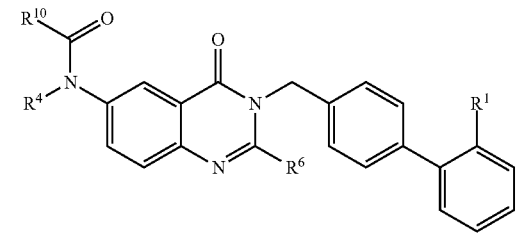

| R⁶ | R¹ | R¹⁰ | R⁴ | R⁶ | R¹ | R¹⁰ | R⁴ |
|---|---|---|---|---|---|---|---|
| Pr | TET | Ph | Pn | Me | TET | Ph | Bn-2-Cl |
| Pr | TET | Bn | Pn | Me | TET | 4-Pyr | Bn |
| Pr | TET | 4-Pyr | Pn | Pr | SO₂NHCOcPr | Me | Me |
| Pr | TET | Ph | Bn | Pr | TET | Ph | CH₂CO₂Et |
| Pr | TET | Ph-4-Cl | Pn | Me | TET | 4-Pyr | Bn-2-Cl |
| Pr | TET | Ph-4-Cl | Pn | Me | TET | 4-Pyr | CH₂CH=CMe₂ |
| Pr | TET | Ph-4-Ome | 4-Methylpentyl | Et | TET | Ph | Bn-4-I |
| Pr | TET | 2-Furyl | Pn | Pr | TET | 2-thienyl | Pn |
| Pr | TET | 3-methylbutyl | | Pr | TET | 2-thienyl | Me |
| Pr | TET | Bu | Pn | iPr | TET | Ph | Bn-4-I |
| Pr | TET | Ph-4-F | Bn | Et | TET | Ph-4-I | Bn |
| Pr | TET | Ph-4-F | Pn | Et | TET | Ph | Bz-2-I |
| Pr | TET | Ph-4-F | Bu | Et | TET | 2-thienyl | Bn |
| Pr | TET | Ph-4-Me | Pn | Pr | TET | 4-Pyr | (CH₂)₂OMe |
| Pr | TET | Ph-3-Br | Pn | Pr | TET | Ph | CH₂CO₂H |
| Pr | TET | 3-Methylbutyl | Bn-4-OH | CH₂OMe | TET | Ph-4-Cl | Pn |
| Pr | TET | Bu | Bu | Et | TET | 2-furoyl | Bn |
| Et | TET | Ph | Bn | Pr | TET | 2-thienyl | Bn |
| Pr | TET | Ph-4-CF₃ | Pn | Pr | TET | 2-thienyl | Et |
| Et | TET | Ph-4-F | Pn | Pr | TET | 2-furoyl | Et |
| 1-Methylpentyl | TET | Ph-4-F | Pn | Pr | TET | Ph-2-OMe | Bn |
| Et | TET | Ph-4-F | Bu | Pr | TET | Ph-2-OMe | Pr |
| Et | TET | Ph | Bn-4-F | Pr | TET | Ph-4-OBn | Pn |
| cPr | TET | Ph | Bn | Pr | TET | Ph-4-OBn | Pr |
| cPr | TET | Ph | Pn | Pr | TET | Ph-4-OH | Pn |
| 1-Methyl-3-phenethyl | TET | Ph | Bn | Pr | TET | Ph-4-OH | Pr |
| cPr | TET | Ph | Bn | Pr | TET | CH₂imidazole | Bn |
| cPr | TET | Ph | Bn | Pr | TET | CH₂PIPBoc | Bn |
| Pr | TET | 4-Py | Bu | Pr | TET | 3-Pyr | Bn |
| Me | TET | Ph | Bn | Pr | TET | 2-Pyr | Bn |
| iPr | TET | Ph | Bn | Pr | TET | Ph | CH₂-2-Pyr |
| Et | SO₂NHBz | Ph | Bn | Pr | TET | Ph | CH₂-4-Pyr |
| Pr | TET | 3-Pyr | Pn | Pr | TET | 4-Pyr | Bn |
| Pr | SO₂NHCOcPr | Ph | Pn | Pr | TET | 2-Pyr | Bn |
| Pr | SO₂NHBz | Ph | Pn | Pr | TET | Ph | CH₂-3-Pyr |
| Et | TET | 4-Pyr | Bn | Pr | TET | Ph | CH₂-2-Pyr |
| Pr | TET | Ph-4-SMe | Pn | Pr | TET | Ph-4-OPO(OBn)₂ | Pn |
| Pr | TET | Ph | Pr | Pr | TET | Ph-4-OH | Bu |
| Et | TET | Ph-2-Cl | Bn | Pr | TET | 4-Pyr | CH₂-2-Pyr |
| Et | TET | Ph-2-Cl | Bn-2-Cl | Pr | TET | Ph-4-OP(OH)₂ | Pn |
| Pr | TET | Ph-4-SOMe | Pn | Pr | TET | Ph-4-OH | Bn |
| Pr | TET | Ph | (CH₂)CHO | Pr | TET | 2-furoyl | CH₂-2-Pyr |
| Pr | TET | Ph-4-SO₂Me | Pn | Pr | TET | Ph-4-OPO(ONa)₂ | Bu |
| Et | TET | Ph | Bn-2-Cl | | | | |
| Et | TET | Ph | CH₂CH=CMe₂ | | | | |
| Pr | SO₂NHCOcPr | Me | Pr | | | | |
| Pr | SO₂NHCOcPr | cPr | Pn | | | | |
| Pr | SO₂NHCOcPr | Me | Pn | | | | |
| Pr | SO₂NHCOPh | cPr | Pr | | | | |
| Pr | TET | Ph-4-F | Pr | | | | |
| Et | TET | Ph | iPn | | | | |
| iPr | TET | Ph | Bn-2-Cl | | | | |
| iPr | TET | cPr | Bn | | | | |
| iPr | TET | cPr | Bn-2-Cl | | | | |
| H | TET | Ph | Bn | | | | |
| H | TET | Ph | Bn-2-Cl | | | | |
| Et | TET | Ph | Bn-4-Cl | | | | |
| Et | TET | Ph | Bn-4-F | | | | |
| 1-ethyl-ethyl | TET | Ph | -Bn-3-Et | | | | |
| 1-ethyl-ethyl | TET | Ph | Bn | | | | |
| 1-ethyl-ethyl | TET | Ph | Bn-2-Cl | | | | |
| Pr | TET | Ph | iBu | | | | |
| Pr | TET | Ph | (CH₂)₃CO₂Et | | | | |
| Pr | NHSO₂CF₃ | Ph | Pn | | | | |
| Pr | TET | Ph | (CH₂)₃CO₂H | | | | |

In a fourth embodiment of the compounds of the formula (IIa), $R^5$ is $SO_2R^{10}$. One class of this embodiment is represented by the compounds of the formula (IIa) wherein:
$R^1$ is tetrazol-5-yl, $SO_2NHSO_2CF_3$ or $NHSO_2CF_3$
$R^3$ is
(a) phenyl,
(b) substituted phenyl in which the substituent is F, Cl, Br, I or $C_1$-$C_4$ alkoxy,
(c) $C_1$-$C_8$ alkyl substituted with di-($C_1$-$C_4$ alkyl)amino or $NH_2$, or
(d) $C_3$-$C_7$-cycloalkyl;
$R^4$ is
(a) $C_2$-$C_6$ alkyl,
(b) substituted $C_1$-$C_6$ alkyl in which the substituent is: CHO, $CO_2C_1$-$C_4$ alkyl, $CO_2H$, $OC_1$-$C_4$ alkyl, cyclohexyl, phenyl, or $NHCO_2tBu$,
(c) benzyl,
(d) substituted benzyl in which the substituent on the phenyl group is: F, Cl, Br, I, OH, $OPO(OC_1$-$C_4$ alkyl)$_2$, OPO(Obenzyl)$_2$, OPO(OH)$_2$, —PO(OC$_1$-C$_4$ alkyl)$_2$, —PO(Obenzyl)$_2$, —OPO(OH)$_2$, NO$_2$, NH$_2$, N(C$_1$-C$_4$ alkyl)$_2$, or Obenzyl,
(e) CH$_2$-heteroaryl or
(f) C$_3$-C$_6$ alkenyl;
R$^6$ is
(a) C$_1$-C$_6$ alkyl,
(b) substituted C$_1$-C$_6$ alkyl in which the substituent is: -benzyl, —C$_1$-C$_3$ alkyl, or —OC$_1$-C$_4$ alkyl or,
(c) cyclopropyl;
R$^{10}$ is
(a) phenyl,
(b) substituted phenyl in which the substituent is F, Cl, Br, I, methoxy, methyl, CF$_3$, SMe, SOMe, SO$_2$Me, OH, OPO(O—C$_1$-C$_4$ alkyl)$_2$, OPO(OH)$_2$, OPO(OBn)$_2$, CO$_2$C$_1$-C$_4$ alkyl, or COOH,
(c) benzyl,
(d) heteroaryl,
(e) C$_1$-C$_6$ alkyl, or
(f) substituted C$_1$-C$_6$ alkyl substituted with: imidazole, piperazine, morpholinyl, N—(C$_1$-C alkyl)-piperazinyl, N—(COC$_1$-C$_6$ alkyl)-piperazinyl, or N-aryl-piperazinyl;
R$^{11}$ and R$^{12}$ are hydrogen.

Illustrating this class of the fourth embodiment is the following compounds (with its Example Number designation) of the formula (IIa):

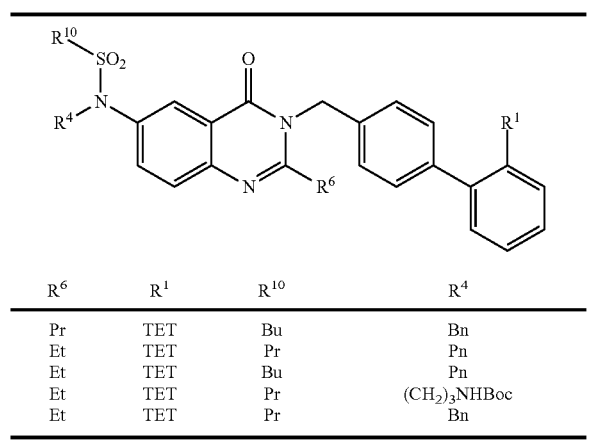

| R$^6$ | R$^1$ | R$^{10}$ | R$^4$ |
|---|---|---|---|
| Pr | TET | Bu | Bn |
| Et | TET | Pr | Pn |
| Et | TET | Bu | Pn |
| Et | TET | Pr | (CH$_2$)$_3$NHBoc |
| Et | TET | Pr | Bn |

In still other embodiments, the AT$_2$ receptor antagonist is selected from the substituted quinazolinone compounds listed in U.S. Pat. No. 5,441,959 and especially in the compound claims of this patent. Representative examples of such compounds are represented by the formula (IIIa):

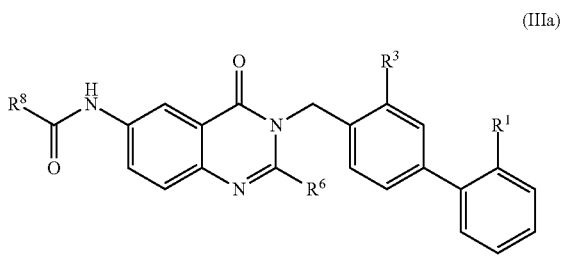

(IIIa)

or a pharmaceutically compatible salt thereof, wherein:
R$^1$ is —SO$_2$NHCO$_2$R$^{23}$;
R$^3$ is
(a) halogen (Cl, Br, I, F),
(b) C$_1$-C$_4$ alkyl, or
(c) CF$_3$;
R$^6$ is straight chain C$_1$-C$_4$ alkyl;
R$^8$ is
(a) R$^{23'}$
(b) NR$^{24}$R$^{23'}$;
R$^{23}$ and R$^{23'}$ are independently
(a) aryl, wherein aryl is defined as phenyl or naphthyl unsubstituted or substituted with one or two substituents selected from the group consisting of: halogen (Cl, Br, I, F), N(R$^{24}$)$_2$, CO$_2$R$^{24}$, C$_1$-C$_4$ alkyl, C$_1$-C$_4$ alkoxyl, NO$_2$, CF$_3$, C$_1$-C$_4$ alkylthio, OH, —SO$_2$N(R$^{24}$)$_2$, C$_3$-C$_7$ cycloalkyl, C$_3$-C$_{10}$ alkenyl and S(O)$_n$(C$_1$-C$_4$ alkyl); where n=1 or 2,
(b) heteroaryl, wherein heteroaryl is an unsubstituted or mono or disubstituted heteroaromatic 5- or 6-membered ring which can contain one or two heteroatoms selected from the group consisting of N, O and S and wherein the substituents are members selected from the group consisting of —OH, —SH, C$_1$-C$_4$ alkyl, C$_1$-C$_4$ alkoxy, CF$_3$, halogen (Cl, Br, I, F) and NO$_2$,
(c) C$_3$-C$_7$ cycloalkyl,
(d) C$_1$-C$_6$ alkyl optionally substituted with a substituent selected from the group consisting of aryl as defined above, heteroaryl as defined above, —OH, —SH, C$_1$-C$_4$ alkyl, —O(C$_1$-C$_4$ alkyl), C$_3$-C$_7$ cycloalkyl, —S(O)$_n$ (C$_1$-C$_4$ alkyl), —CF$_3$, halogen (Cl, Br, F, I), —NO$_2$, —CO$_2$H, CO$_2$—(C$_1$-C$_4$ alkyl), —NH$_2$, —NH(C$_1$-C$_4$ alkyl), —N(C$_1$-C$_4$ alkyl)$_2$, or
(e) perfluoro-C$_1$-C$_4$ alkyl; and
R$^{24}$ is
(a) H,
(b) C$_1$-C$_4$ alkyl, unsubstituted or substituted with aryl as defined above or heteroaryl as defined above, or
(c) aryl; and
R$^{23'}$ and R$^{24}$ when taken together may form a morpholine or piperazine ring, wherein the piperazine ring may be substituted on the nitrogen with C$_1$-C$_4$ alkyl or C$_1$-C$_4$ acyl.

One embodiment of the compounds of formula (IIIa) are those wherein:

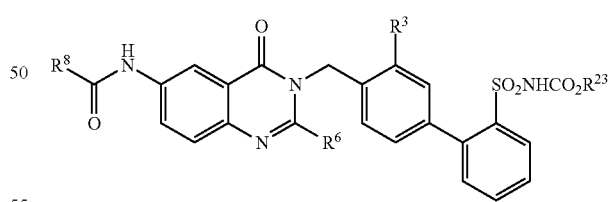

R$^3$ is
(a) F,
(b) Me, or
(c) CF$_3$;
R$^6$ is straight chain C.sub.1-C.sub.4 alkyl;
R$^8$ is R$^{23'}$;
R$^{23'}$ is
(a) aryl, wherein aryl is defined as phenyl or naphthyl unsubstituted or substituted with one or two substituents selected from the group consisting of: halogen (Cl, Br, I, F), N(R$^{24}$)$_2$, CO$_2$R$^{24}$, C$_1$-C$_4$ alkyl, C$_1$-C$_4$ alkoxyl, NO$_2$, CF$_3$, C$_1$-C$_4$ alkylthio, OH, —SO$_2$N(R$^{24}$)$_2$, C$_3$-C$_7$ cycloalkyl, C$_3$-C$_{10}$ alkenyl and S(O)$_n$ (C$_1$-C$_4$ alkyl); where n=1 or 2, (b) heteroaryl, wherein heteroaryl is an unsubstituted or mono- or disubstituted heteroaromatic 5- or 6-membered ring which can contain one or two heteroatoms selected from the group consisting of N, O and S and Wherein the substituents are members selected from the group consisting of —OH, —SH, C$_1$-C$_4$ alkyl, C$_1$-C$_4$ alkoxy, CF$_3$, halogen (Cl, Br, I, F) and NO$_2$, (c) C$_1$-C$_6$ alkyl unsubstituted or substituted with a substituent selected from the group consisting of aryl as defined above, heteroaryl as defined above, —OH, —SH, C$_1$-C$_4$ alkyl, —O(C$_1$-C$_4$ alkyl), C$_3$-C$_7$ cycloalkyl, —CF$_3$, halogen (Cl, Br, F, I), —N(C$_1$-C$_4$ alkyl)$_2$, or C$_3$-C$_7$ cycloalkyl; and R$^{23}$ is (a) C$_1$-C$_6$-alkyl, unsubstituted or substituted with a substituent selected from the group consisting of: aryl as defined above, heteroaryl as defined above, C$_1$-C$_4$ alkyl, CF$_3$, —O(C$_1$-C$_4$ alkyl), C$_3$-C$_7$ cycloalkyl, or (b) perfluoro-C$_1$-C$_4$-alkyl.

This embodiment is exemplified further by:

| R$^{23}$ | R$^3$ | R$^6$ | R$^8$ |
|---|---|---|---|
| iPn | F | Pr | Ph |
| iPn | F | Pr | -2-furoyl |
| iPn | F | Bu | Et |
| iPn | F | Bu | Pr |
| iPn | F | Pr | CH$_2$OCH$_2$CH$_3$ |
| iPn | F | Et | -2-furoyl |
| iPn | F | Et | Ph |
| iPn | F | Et | -3-pyridyl |
| iPn | F | Et | -4-pyridyl |
| iPn | F | Et | -2-pyridyl |
| (CH$_2$)$_2$cPr | F | Et | Ph |
| (CH$_2$)$_2$cPr | F | Et | -2-furoyl | wherein:

Et is ethyl,

Pr is n-propyl, cPr is cyclopropyl,

Bu is n-butyl, iPn is 3-methylbutyl, and

Ph is phenyl.

A second embodiment of structures of formula (IIIa) are those wherein R$^{23}$, R$^3$, R$^6$ are as recited in the first embodiment and all other substituents are as recited below:

R$^8$ is —NR$^{24}$R$^{23'}$;

R$^{23'}$ is C$_1$-C$_6$ alkyl which is unsubstituted or substituted with a substituent selected from the group aryl, heteroaryl, C$_1$-C$_4$ alkyl, —O(C—C$_4$ alkyl), CF$_3$, NH(C$_1$-C$_4$ alkyl), N(C$_1$-C$_4$ alkyl)$_2$, C$_3$-C$_7$ cycloalkyl;

R$^{24}$ is (a) C$_1$-C$_6$ alkyl which is unsubstituted or substituted with aryl or heteroaryl, or (b) H; and R$^{23'}$ and R$^{24}$ when taken together may form a morpholine or piperazine ring, wherein the piperazine ring may be substituted on the nitrogen with C$_1$-C$_4$ alkyl or C$_1$-C$_4$ acyl.

Compounds exemplifying this embodiment include:

| R$^{23}$ | R$^3$ | R$^6$ | R$^{23'}$ | R$^{24}$ |
|---|---|---|---|---|
| iPn | Me | Pr | iPr | H |
| Bu | Me | Pr | iPr | H |
| Bu | F | Pr | iPr | H |
| iPn | F | Pr | iPr | H |
| iPn | Me | Pr | iPr | H |
| Bu | F | Bu | iPr | Me |
| iPn | F | Pr | iPr | H |
| (CH$_2$)$_2$cPr | F | Bu | iPr | Me |
| (CH$_2$)$_2$cPr | F | Et | Et | H |
| Me | F | Et | Et | H |
| iPn | F | Pr | morpholino | |
| iPn | F | Bu | iPr | Me |
| iPn | F | Et | iPr | Me |
| iPn | F | Et | morpholino | |
| Bu | F | Et | morpholino | |
| iPn | F | Bu | piperazinyl-4-methyl | |
| Bu | F | Et | iPr | Me |
| (CH$_2$)$_2$tBu | F | Pr | iPr | H |
| tBu | F | Pr | iPr | H |
| iPr | F | Pr | Me | Me |
| iHex | F | Et | morpholino | |
| iPn | F | Et | Me | Me |
| (CH$_2$)$_2$cPr | F | Et | iPr | H |
| (CH$_2$)$_2$cPr | F | Et | iPr | Me |
| iPn | F | Me | iPr | H |
| iPn | F | Me | iPr | Me |
| (CH$_2$)$_2$cPr | F | Me | Me | Me |
| iBu | F | Et | iPr | Me |
| iPn | F | Et | iPr | Me | wherein:

Me is methyl,

Et is ethyl,

Pr is n-propyl, cPr is cyclopropyl, iPr is isopropyl,

Bu is n-butyl, iBu is isobutyl,
tBu is t-butyl,
iPn is 3-methylbutyl, and
iHex is 4-methylpentyl.

In the above embodiments described above for compounds according to formula (IIIa), the heteroaryl substituent represents any 5 or 6-membered aromatic ring containing from one to three heteroatoms selected from the group consisting of nitrogen, oxygen, and sulfur, for example, pyridyl, thienyl, furyl, pyrazolyl, pyrrolyl, imidazolyl, pyridazinyl, pyrimidinyl, pyrazinyl, isoxazolyl, isothiazolyl, oxazolyl, triazolyl and thiazolyl.

In still other embodiments, the $AT_2$ receptor antagonist is selected from the imidazole compounds listed in U.S. Pat. No. 5,545,651 and especially in the compound claims of this patent. Representative examples of such compounds are represented by the formula (IVa):

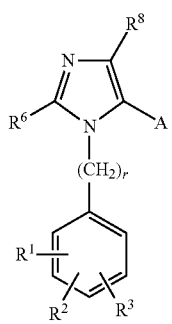
(IV)

wherein:
$R^1$ is in the meta or para position and is
(a) 4-$CO_2H$,
(b) —$CH_2CO_2H$,
(c) —$C(CF_3)_2OH$,
(d) —$CONHNHSO_2CF_3$,
(e) 4-$CONHCH(CO_2H)CH_2C_6H_5$(L-isomer),
(f) 4-$CONHOR^{12}$,
(g) —$CONHSO_2R^{10}$,
(h) —$CONHSO_2NHR^9$,
(i) —$C(OH)R^9PO_3H_2$,
(j) —$NHCOCF_3$,
(k) —$NHCONHSO_2R^{10}$,
(l) —$NHPO_3H_2$,
(m) 4-$NHSO_2R^{10}$,
(n) —$NHSO_2NHCOR^{10}$,
(o) —$OPO_3H_2$,
(p) —$OSO_3H$,
(q) —$PO_3H_2$,
(r) —$PO(OH)R^9$,
(s) —$SO_3H$,
(t) —$SO_2NHR^9$,
(u) —$SO_2NHCOR^{10}$,
(v) —$SO_2NHCONHR^9$,

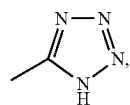
(w)

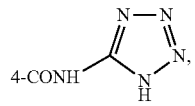
(x)

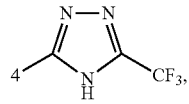
(y)

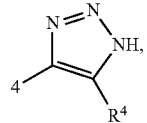
(z)

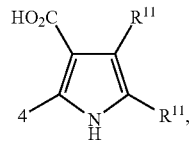
(aa)

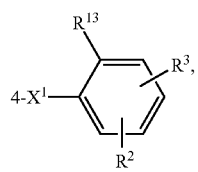
(bb)

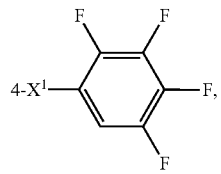
(cc)

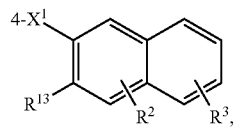
(dd)

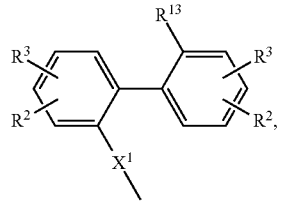
(ee)

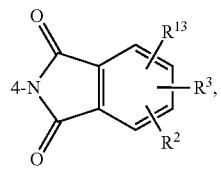
(ff)

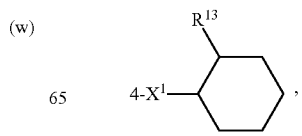
(gg)

(hh) 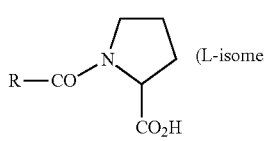 (L-isomer), (ii) —SO$_2$NHCO$_2$R$^{10}$,

R$^2$ is independently
(a) H,
(b) halo (F, Cl, Br, I),
(c) C$_1$-C$_4$-alkyl,
(d) C$_1$-C$_4$alkoxy,
(e) C$_1$-C$_4$-acyloxy,
(f) C$_1$-C$_4$-alkylthio,
(g) C$_1$-C$_4$-alkylsulfinyl,
(h) C$_1$-C$_4$-alkylsulfonyl,
(i) —(C$_1$-C$_4$-alkyl)-OH,
(j) —(C$_1$-C$_4$) alkyl-aryl,
(k) —CO$_2$H,
(l) —CN,
(m) tetrazol-5-yl,
(n) —CONHOR$^{12}$,
(o) —SO$_2$NHR$^9$,
(p) —NH$_2$,
(q) C$_1$-C$_4$-alkylamino,
(r) C$_1$-C$_4$-dialkylamino,
(s) —NHSO$_2$R$^{10}$,
(t) —NO$_2$,
(u) furyl,
(v) phenyl or phenyl optionally substituted with one or two substituents selected from the group consisting of halo, C$_1$-C$_4$-alkyl, C$_1$-C$_4$-alkoxy, —NO$_2$, —CF$_3$, C$_1$-C$_4$-alkylthio, —OH, —NH$_2$, C$_1$-C$_4$-alkylamino, C$_1$-C$_4$-dialkylamino, —CN, —CO$_2$R$^{12}$, acetyl;

R$^3$ is independently
(a) H,
(b) halo,
(c) C$_1$-C$_4$-alkyl,
(d) C$_1$-C$_4$-alkoxy, or
(e) —C$_1$-C$_4$-alkyl-(C$_1$-C$_4$-alkoxy);

R$^4$ is
(a) —CN,
(b) —NO$_2$, or
(c) —CO$_2$R$^{11}$;

R$^5$ is
(a) H,
(b) C$_1$-C$_6$-alkyl,
(c) C$_3$-C$_6$-cycloalkyl,
(d) C$_2$-C$_4$-alkenyl, or
(e) C$_2$-C$_4$-alkynyl;

R$^6$ is
(a) C$_1$-C$_{10}$-alkyl,
(b) C$_3$-C$_{10}$-alkenyl,
(c) C$_3$-C$_{10}$-alkynyl,
(d) C$_3$-C$_8$-cycloalkyl,
(e) C$_3$-C$_4$-cycloalkenyl,
(f) —C$_1$-C$_3$-alkyl-(C$_3$-C$_8$-cycloalkyl),
(g) —C$_1$-C$_3$-alkenyl-(C$_5$-C$_{10}$-cycloalkyl),
(h) —C$_1$-C$_3$-alkynyl-(C$_5$-C$_{10}$-cycloalkyl),
(i) —(CH$_2$)$_s$S(CH$_2$)$_m$R$^5$, or
(j) benzyl, optionally substituted on the phenyl ring with 1-2 substituents selected from the group consisting of halo, C$_1$-C$_4$-alkyl, C$_1$-C$_4$-alkoxy or —NO$_2$;

R$^7$ is
(a) C$_1$-C$_6$-alkyl,
(b) C$_3$-C$_6$-cycloalkyl,
(c) aryl, or
(d) benzyl, optionally substituted on the phenyl ring with 1-2 substituents selected from the group consisting of halo, C$_1$-C$_4$-alkyl, C$_1$-C$_4$-alkoxy or —NO$_2$;

R$^8$ is
(a) H,
(b) halogen (F, Cl, Br, I),
(c) phenyl, or phenyl optionally substituted with halogen (F, Cl, Br, I), C$_1$-C$_4$-alkyl, —OH, C$_1$-C$_4$-alkoxy, —NO$_2$, —NR$^{26}$R$^{27}$, —NR$^{26}$COR$^{11}$, —NR$^{26}$CO$_2$R$^7$, —S(O)$_r$R$^{10}$, —SO$_2$NR$^{26}$R$^{27}$, —NR$^{26}$CF$_3$,
(d) C$_1$-C$_6$-alkyl, optionally substituted with
  i) OR$^{25}$,
  ii) S(O)$_r$R$^{10}$,
  iii) NR$^{23}$R$^{24}$,
  iv) NR$^{26}$COR$^{11}$,
  v) NR$^{26}$CO$_2$R$^7$,
  vi) NR$^{26}$CONR$^{23}$R$^{24}$,
  vii) OCONR$^{23}$R$^{24}$,
  viii) OCOR$^{11}$,
  ix) aryl,
(e) C$_2$-C$_4$-alkenyl,
(f) —C$_1$-C$_4$-alkyl-aryl,
(h) C$_1$-C$_4$-alkoxy,
(i) C$_v$F$_{2v+1}$ where v=1 to 3,
(j) —S(O)$_r$R$^{10}$,
(k) —S(O)$_2$NR$^{23}$R$^{24}$,
(l) —CONR$^{23}$R$^{24}$,
(m) —COR$^7$, or
(n) —CO$_2$R$^{12}$;

R$^9$ is
(a) H,
(b) C$_1$-C$_5$-alkyl,
(c) aryl,
(d) —(C$_1$-C$_4$-alkyl)-aryl,
(e) heteroaryl, or
(f) C$_3$-C$_5$-cycloalkyl;

R$^{10}$ is
(a) aryl,
(b) C$_3$-C$_7$-cycloalkyl,
(c) C$_1$-C$_4$-perfluoroalkyl,
(d) C$_1$-C$_1$-alkyl, optionally substituted with a substituent selected from the group consisting of aryl, heteroaryl, —OH, —SH, C$_1$-C$_4$-alkyl, C$_1$-C$_4$-alkoxy, C$_1$-C$_4$-alkylthio, —CF$_3$, halo, —NO$_2$, —CO$_2$R$^{12}$, —NH$_2$, C$_1$-C$_4$-alkylamino, C$_1$-C$_4$-dialkylamino, —PO$_3$H$_2$, or
(e) heteroaryl;

R$^{11}$, R$^{11a}$ and R$^{11b}$ are independently
(a) H,
(b) C$_1$-C$_6$-alkyl,
(c) C$_3$-C$_6$-cycloalkyl,
(d) aryl,
(e) —(C$_1$-C$_5$-alkyl)-aryl, or
(f) heteroaryl;

R$^{12}$ is
(a) H,
(b) methyl, or
(c) benzyl, optionally substituted on the phenyl ring with 1-2 substituents selected from the group consisting of halo, C$_1$-C$_4$-alkyl, C$_1$-C$_4$-alkoxy or —NO$_2$;

R$^{13}$ is
(a) —CO$_2$H,
(b) —CH$_2$CO$_2$H,
(c) —C(CF$_3$)$_2$OH, (d) —CONHNHSO$_2$CF$_3$,
(e) —CONHOR$^{12}$,
(f) —CONHSO$_2$R$^{10}$,
(g) —CONHSO$_2$NHR$^9$,
(h) —C(OH)R$^9$PO$_3$H$_2$,
(i) —NHCOCF$_3$,
(j) —NHCONHSO$_2$R$^{10}$,
(k) —NHPO$_3$H$_2$,
(l) —NHSO$_2$R$^{10}$,
(m) —NHSO$_2$NHCOR$^{10}$,
(n) —OPO$_3$H$_2$,
(o) —OSO$_3$H,
(p) —PO(OH)R$^9$,
(q) —PO(OH)$_2$,
(r) —SO$_3$H,
(s) —SO$_2$NHR$^9$,
(t) —SO$_2$NHCOR$^{10}$,
(u) —SO$_2$NHCONHR$^9$,
(v) —SO$_2$NHCO$_2$R$^{10}$,

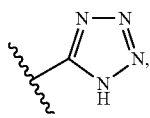
(w)

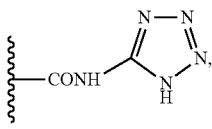
(x)

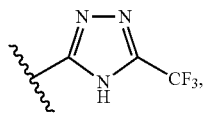
(y)

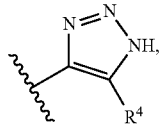
(z)

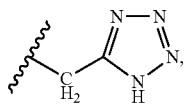
(aa)

R$^{14}$ is
(a) H,
(b) C$_1$-C$_6$-alkyl,
(c) —CH$_2$CH=CH$_2$, or
(d) benzyl, optionally substituted on the phenyl ring with 1-2 substituents selected from the group consisting of halo, C$_1$-C$_4$-alkyl, C$_1$-C$_4$-alkoxy or —NO$_2$;
R$^{15}$ is
(a) H,
(b) C$_1$-C$_8$-alkyl,
(c) C$_1$-C$_8$-perfluoroalkyl,
(d) C$_3$-C$_6$-cycloalkyl,
(e) aryl, or
(f) benzyl, optionally substituted on the phenyl ring with 1-2 substituents selected from the group consisting of halo, C$_1$-C$_4$-alkyl, C$_1$-C$_4$-alkoxy or —NO$_2$;

R$^{16}$ is
(a) H,
(b) C$_1$-C$_6$-alkyl, or
(c) benzyl, optionally substituted on the phenyl ring with 1-2 substituents selected from the group consisting of halo, C$_1$-C$_4$-alkyl, C$_1$-C$_4$-alkoxy or —NO$_2$;
R$^{17}$ is
(a) H,
(b) C$_1$-C$_6$-alkyl,
(c) C$_3$-C$_6$-cycloalkyl,
(d) aryl, or
(e) benzyl, optionally substituted on the phenyl ring with 1-2 substituents selected from the group consisting of halo, C$_1$-C$_4$-alkyl, C$_1$-C$_4$alkoxy or —NO$_2$;
R$^{18}$ is
(a) —NR$^{19}$R$^{20}$
(b) —NHCONH$_2$,
(c) —NHCSNH$_2$, or
(d) —NHSO$_2$—C$_6$H$_5$;
R$^{19}$ and R$^{20}$ are independently
(a) H,
(b) CC$_1$-C$_5$-alkyl, or
(c) aryl,
R$^{21}$ and R$^{22}$ are independently
(a) C$_1$-C$_4$-alkyl,
or taken together are
(b) —(CH$_2$)$_q$—;
R$^{23}$ and R$^{24}$ are, independently
(a) H,
(b) C$_1$-C$_6$-alkyl,
(c) aryl, or
(d) —(C$_1$-C$_4$-alkyl)-aryl, or
(e) R$^{23}$ and R$^{24}$ when taken together constitute a pyrrolidine, piperidine or morpholine ring;
R$^{25}$ is
(a) H,
(b) C$_1$-C$_4$-alkyl,
(c) aryl,
(d) —(C$_1$-C$_4$-alkyl)-aryl,
(e) C$_3$-C$_6$-alkenyl, or
(f) —(C$_3$-C$_6$-alkenyl)-aryl;
R$^{26}$ and R$^{27}$ are independently
(a) H,
(b) C$_1$-C$_4$-alkyl,
(c) aryl, or
(d) —CH$_2$-aryl;
R$^{28}$ is
(a) aryl, or
(b) heteroaryl;
R$^{29}$ is
(a) —CHO,
(b) —CONH$_2$,
(c) —NHCHO,
(d) —CO—(C$_1$-C$_6$ perfluomalkyl),
(e) —S(O)$_r$—(C$_1$-C$_6$ perfluoroalkyl),
(f) —O—(C$_1$-C$_{66}$ perfluoroalkyl), or
(g) —NR$^{11a}$—(C$_1$-C$_6$ perfluoroalkyl);
R$^{30}$ is
(a) —CHO,
(b) —SO$_2$—(C$_1$-C$_6$ perfluoroalkyl), or
(c) —CO—(C$_1$-C$_6$ perfluoroalkyl);
A is
(a) —(CH$_2$)$_n$-L$^1$-B-(T)$_y$-(B)$_y$—X$^2$—(B)$_y$—R$^{28}$,
(b) —(CH$_2$)$_n$-L$^1$-B-T-(B)$_y$—R$^{28}$,
(c) —(CH$_1$)$_n$-L-B-(T)$_y$-(B)$_y$—X$^2$—B,
(d) —(CH$_2$)$_n$-L-B-T-(B)$_y$—R$^{29}$,
(e) —(CH$_2$)$_n$-L$^1$-T-(B)$_y$—X$^2$ (B)$_y$—R$^{28}$, (f) —(CH$_2$)$_n$-L$^1$-T-(B)$_y$—R$^{28}$,
(g) —(CH$_2$)$_n$-L$^1$-T-(B)$_y$—X$^2$—B,
(h) —(CH$_2$)$_n$-L$^1$-(CR$^{19}$R$^{20}$)-D-(T)$_y$-(B)$_y$—X$^3$—(B)$_y$—R$^{28}$,
(i) —(CH$_2$)$_n$-L$^1$-(CR$^{19}$R$^{20}$)-D-T-(B)$_y$—R$^{28}$,
(j) —(CH$_2$)$_n$-L$^1$-(CR$^{19}$R$^{20}$)-D-(T)$_y$-(B)$_y$—X$^3$—B,
(k) —(CH$_2$)$_n$-L$^1$-(CR$^{19}$R$^{20}$)-D-T-(B)$_y$—R$^{29}$,
(l) —(CH$_2$)$_n$-L$^1$-(CR$^{19}$R$^{20}$)-D-T-(B)$_y$—X$^4$—(B)$_y$—R$^{28}$,
(m) —(CH$_2$)$_n$-L$^1$-(CR$^{19}$R$^{20}$)-D-B—X$^4$—(B)$_y$—R$^{28}$,
(n) —(CH$_2$)$_n$-L$^1$-(CR$^{19}$R$^{20}$)-D-T-(B)$_y$—X$^4$—B,
(o) —(CH$_2$)$_n$-L$^1$-(CR$^{19}$R$^{20}$)-D-B—X$^4$—B,
(p) —(CH$_2$)$_n$-L$^2$-B-(T)$_y$-(B)$_y$—X$^2$—(B)$_y$—R$^{28}$,
(q) —(CH$_2$)$_n$-L$^2$-B-T-(B)$_y$—R$^{28}$,
(r) —(CH$_2$)$_n$-L$^2$-B-(T)$_y$-(B)$_y$—X$^2$—B,
(s) —(CH$_2$)$_n$-L$^2$-B-T-(B)$_y$—R$^{29}$,
(t) —(CH$_2$)$_n$-L$^2$-T-(B)$_y$—X$^2$—(B)$_y$—R$^{28}$,
(u) —(CH$_2$)$_n$-L$^2$-T-(B)$_y$—R$^{28}$,
(v) —(CH$_2$)$_n$-L$^2$-T-(B)$_y$—X$^2$—B,
(w) —(CH$_2$)$_n$-L$^2$-D-(T)$_y$-(B)$_y$—X$^3$—(B)$_y$—R$^{28}$,
(x) —(CH$_2$)$_n$-L$^2$-D-T-(B)$_y$—R$^{28}$,
(y) —(CH$_2$)$_n$-L$^2$-D-(T)$_y$-(B)$_y$—X$^3$—B,
(z) —(CH$_2$)$_n$-L$^2$-D-T-(B)$_y$—R$^{29}$,
(aa) —(CH$_2$)$_n$-L$^2$-D-T-(B)$_y$—X$^4$—(B)$_y$—R$^{28}$,
(bb) —(CH$_2$)$_n$-L$^2$-D-B—X$^4$—(B)$_y$—R$^{28}$,
(cc) —(CH$_2$)$_n$-L$^2$-D-T-(B)$_y$—X$^4$—B,
(dd) —(CH$_2$)$_n$-L$^2$-D-B—X$^4$—B,
(ee) —(CH$_2$)$_m$-L$^3$-B-(T)$_y$-(B)$_y$—X$^2$—(B)$_y$—R$^{28}$,
(ff) —(CH$_2$)$_m$-L$^3$-B-T-(B)$_y$—R$^{28}$,
(gg) —(CH$_2$)$_m$-L$^3$-B-(T)$_y$-(B)$_y$—X$^2$—B,
(hh) —(CH$_2$)$_m$-L$^3$-B-T-(B)$_y$—R$^{29}$,
(ii) —(CH$_2$)$_m$-L$^3$-T-(B)$_y$—X$^2$—(B)$_y$—R$^{28}$,
(jj) —(CH$_2$)$_m$-L$^3$-T-(B)$_y$—R$^{28}$,
(kk) —(CH$_2$)$_m$-L$^3$-T-(B)$_y$—X$^2$—B,
(ll) —(CH$_2$)$_m$-L$^3$-(CR$^{19}$R$^{20}$)-D-(T)$_y$-(B)$_y$—X$^3$—(B)$_y$—R$^{28}$,
(mm) —(CH$_2$)$_m$-L$^3$-(CR$^{19}$R$^{20}$)-D-T-(B)$_y$—R$^{28}$,
(nn) —(CH$_2$)$_m$-L$^3$-(CR$^{19}$R$^{20}$)-D-(T)$_y$-(B)$_y$—X$^3$—B,
(oo) —(CH$_2$)$_m$-L$^3$-(CR$^{19}$R$^{20}$)-D-T-(B)$_y$—R$^{29}$,
(pp) —(CH$_2$)$_m$-L$^3$-(CR$^{19}$R$^{20}$)-D-T-(B)$_y$—X$^4$—(B)$_y$—R$^{28}$,
(qq) —(CH$_2$)$_m$-L$^3$-(CR$^{19}$R$^{20}$)-D-(B)—X$^4$—(B)$_y$—R$^{28}$,
(rr) —(CH$_2$)$_m$-L$^3$-(CR$^{19}$R$^{20}$)-D-T-(B)$_y$—X$^4$—B,
(ss) —(CH$_2$)$_m$-L$^3$-(CR$^{19}$R$^{20}$)-D-B—X$^4$—B,

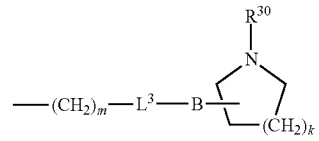
(tt)

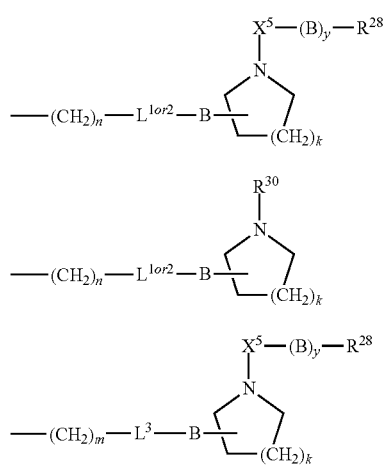
(uu)
(vv)

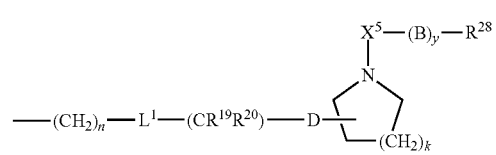
(ww)

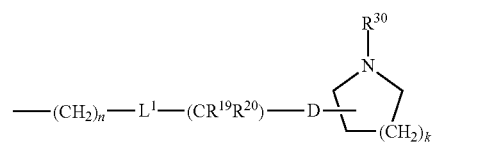
(xx)

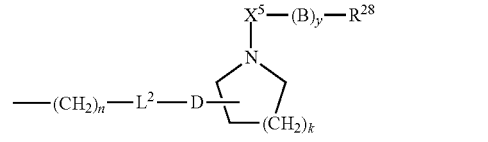
(yy)

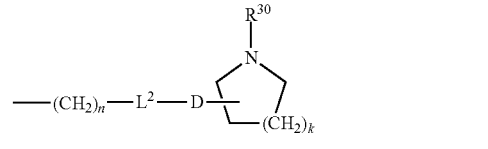
(zz)

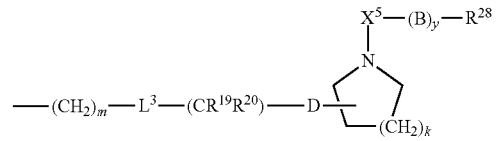
(aaa)

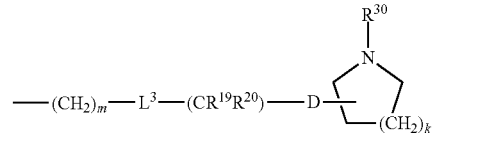
(bbb)
(ccc)

L$^1$ is
(a) —CO$_2$—,
(b) —CONR$^{11a}$—,
(c) —NR$^{11a}$CO$_2$—, or
(d) —NR$^{11a}$CONR$^{11b}$—;
L$^2$ is
(a) —CO—,
(b) NR$^{11a}$CO—, or
(c) —O$_2$C—;
L$_3$ is
(a) —O—,
(b) —SO—, or
(c) —NR$^{11a}$—;
B is C$_1$-C$_6$ alkyl;
D is C$_2$-C$_8$ alkenyl or C$_2$-C$_8$ alkynyl;
T is
(a) arylene, or
(b) heteroarylene
X$^1$ is
(a) a carbon-carbon single bond,
(b) —CO—, (c) —C(R$^{19}$)(R$^{20}$)—,
(d) —O—,
(e) —S—,
(f) —SO—,
(g) —SO$_2$—,
(h) —NR$^{14}$—,
(i) —CONR$^{16}$—,
(j) —NR$^{16}$CO—,
(k) —OC(R$^{19}$)(R$^{20}$)—,
(l) —C(R$^{19}$)(R$^{20}$)O—,
(m) —SC(R$^{19}$)(R$^{20}$)—,
(n) —C(R$^{19}$)(R$^{20}$)S—,
(o) —NHC(R$^{19}$)(R$^{20}$)—,
(p) —C(R$^{19}$)(R$^{20}$)NH—,
(q) —NR$^{16}$SO$_2$—,
(r) —SO$_2$NR$^{16}$—,
(s) —CH=CH—,
(t) —CF=CF—,
(u) —CF=CH—,
(v) —CH=CF—,
(w) —CF$_2$CF$_2$—,
(x) —CH(OR$^{15}$)—,
(y) —CH(OCOR$^{17}$)—,
(z) —C(=NR$^{18}$)—,
(aa) —C(OR$^{21}$)(OR$^{22}$)—,
(bb) 1,2-cyclopropyl, or
(cc) 1,1-cyclopropyl;
X$^2$ is
(a) —CO—,
(b) —O—,
(c) —S(O)$_r$—,
(d) —(C.sub.1-C.sub.4-alkylene)-,
(e) —NR$^{11a}$CONR$^{11b}$—,
(f) —CONR$^{11a}$—,
(g) —NR$^{11a}$CO—,
(h) —SO$_2$NR$^{16}$—,
(i) —NR$^{16}$SO$_2$—,
(j) —OCONR$^{11a}$SO$_2$—,
(k) —SO$_2$NR$^{11a}$CO—,
(l) —SO$_2$NR$^{11a}$CO—,
(m) —OCONR$^{11a}$SO$_2$—,
(n) —SO$_2$NR$^{11a}$CONR$^{11b}$—,
(o) —NR$^{11a}$CONR$^{11b}$SO$_2$—,
(p) —SO$_2$NR$^{11a}$SO$_2$—,
(q) —CONR$^{11a}$SO$_2$NR$^{11b}$—, or
(r) —NR$^{11a}$SO$_2$NR$^{11b}$CO—;
X$^3$ is
(a) —C—,
(b) —SO—,
(c) —SO$_2$—,
(d) single bond,
(e) —CONR$^{11a}$—,
(f) —SO$_2$NR$^{16}$—,
(g) —CONR$^{11a}$SO$_2$—,
(h) —SO$_2$NR$^{11a}$CO—,
(i) —SO$_2$NR$^{11a}$CO$_2$—,
(j) —SO$_2$NR$^{11a}$CONR$^{11b}$—,
(k) —SO$_2$NR$^{11a}$SO$_2$—, or
(l) —CONR$^{11a}$SO$_2$NR$^{11b}$—;
X$^4$ is
(a) —NR$^{11a}$CONR$^{11b}$—,
(b) —OCONR$^{11a}$SO$_2$,
(c) —NR$^{16}$SO$_2$—,
(d) —OCONR$^{11a}$SO$_2$,
(e) —NR$^{11a}$CONR$^{11b}$SO$_2$—, or
(f) —NR$^{11a}$SO$_2$NR$^{11b}$CO—;

X$^5$ is
(a) —CO—,
(b) —SO$_2$—,
(c) —COO—, or
(d) —CONR$^{11a}$—;
Z is
(a) —O—,
(b) —S—, or
(c) —NR$^{11}$—;
k is 1 or 2;
m is 1 to 5;
n is 0 to 2;
q is 2 to 3;
r is 0 to 2;
s is 0 to 5;
t is 0 to 3;
u is 2 to 5;
y is 0 or 1;
and pharmaceutically compatible salts of these compounds.

In specific embodiments, the above compounds are those of formula (IVa) wherein
A is
(a) —(CH$_2$)$_n$-L$^1$-S-(T), —(S)$_y$—X$^2$—(S)$_y$—R$^{28}$,
(b) —(CH$_2$)$_n$-L$^1$-B-T-(B)$_y$—R$^{28}$,
(c) —(CH$_2$)$_n$-L-B-(T)$_y$-(B)$_y$—X$^2$—B,
(d) —(CH$_2$)$_n$-L$^1$-B-T-(B)$_y$—R$^{29}$
(e) —(CH$_2$)$_n$-L$^2$-B-(T)$_y$-(B)$_y$—X$^2$—(B)$_y$—R$^{28}$,
(f) —(CH$_2$)$_n$-L$^2$-B-T-(B)$_y$—R$^{28}$, or
(g) —(CH$_2$)$_n$-L$^2$-B-(T)$_y$-(B)$_y$—X$^2$—B,
(h) —(CH$_2$)$_n$-L$^2$-B-T-(B)$_y$—R$^{29}$;
An illustrative example of the specific embodiments described above is a compound of formula (Va)

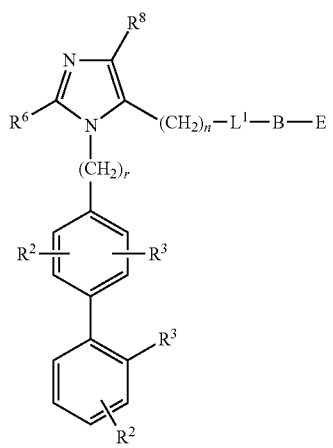

(V)

wherein
R$^2$ is independently
(a) H,
(b) halo (F, Cl, Br, I), or
(c) C$_1$-C$_4$-alkyl;
R$^3$ is
(a) H, or
(b) halo (F, Cl, Br, I);
R$^6$ is
(a) C$_1$-C$_{10}$ alkyl,
(b) C$_3$-C$_{10}$ alkenyl, or
(c) C$_3$-C$_{10}$ alkynyl;

R$^9$ is
(a) H,
(b) C$_1$-C$_5$-alkyl,
(c) aryl,
(d) —(C$_1$-C$_4$-alkyl)-aryl, or
(e) heteroaryl;
R$^{10}$ is
(a) aryl,
(b) C$_3$-C$_7$-cycloalkyl,
(c) C$_1$-C$_4$-perfluoroalkyl,
(d) C$_1$-C$_4$-alkyl, optionally substituted with a substituent selected from the group consisting of aryl, heteroaryl, —OH, —SH, C$_1$-C$_4$ alkyl, C$_1$-C$_4$-alkoxy, C$_1$-C$_4$-alkylthio, —CF$_3$, halo, —NO$_2$, —CO$_2$R$^{12}$, —NH$_2$, C$_1$-C$_4$-alkylamino, C$_1$-C$_4$-dialkylamino, —PO$_3$H$_2$, or
(e) heteroaryl;
R$^{11}$, R$^{11a}$ and R$^{11b}$ are independently
(a) H,
(b) C$_1$-C$_6$-alkyl,
(c) C$_3$-C$_6$-cycloalkyl,
(d) aryl,
(e) —(C$_1$-C$_5$-alkyl)-aryl, or
(f) heteroaryl;
R$^{13}$ is
(a) —CO$_2$H,
(b) —CONHSO$_2$R$^{10}$,
(c) —CONHSO$_2$NHR$^9$,
(d) —NHCONHSO$_2$R$^{10}$,
(e) —NHSO$_2$R$^{10}$,
(f) —NHSO$_2$NHCOR$^{10}$,
(g) —SO$_2$NHR$^9$,
(h) —SO$_2$NHCOR$^{10}$,
(i) —SO$_2$NHCONHR$^9$,
(j) —SO$_2$NHCO$_2$R$^{10}$, or

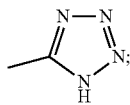
(k)

R$^{16}$ is
(a) H,
(b) C$_1$-C$_6$-alkyl, or
(c) benzyl, optionally substituted on the phenyl ring with 1-2 substituents selected from the group consisting of halo, C$_1$-C$_4$-alkyl, C$_1$-C$_4$-alkoxy or —NO$_2$;
R$^{28}$ is
(a) aryl, or
(b) heteroaryl;
R$^{29}$ is
(a) —CHO,
(b) —CONH$_2$,
(c) —NHCHO,
(d) —CO—(C$_1$-C$_6$ perfluomalkyl),
(e) —S(O)$_r$—(C$_1$-C$_6$ perfluoroalkyl),
E is
(a) -(T)$_y$-(B)$_y$—X$^2$—(B)$_y$—R$^{28}$,
(b) -T-(B)$_y$—R$^{28}$,
(c) -(T)$_y$-(B)$_y$—X$^2$—B or,
(d) -T-(B)$_y$—R$^{29}$;
L$^1$ is
(a) —CO$_2$—,
(b) —CONR$^{11a}$—,
(c) —NR$^{11a}$CO$_2$—,
(d) —NR$^{11a}$CONR$^{11b}$—;

B is C$_1$-C$_6$ alkyl;
X$^2$ is
(a) —CO—,
(b) —O—,
(c) —S(O)$_r$—,
(d) —(C$_1$-C$_4$-alkylene)-,
(e) —NR$^{11a}$CONR$^{11b}$—,
(f) —CONR$^{11a}$—,
(g) —NR$^{11a}$CO—,
(h) —SO$_2$NR$^{16}$—,
(i) —NR$^{16}$SO$_2$—,
(j) —CONR$^{11a}$SO$_2$—,
(k) —SO$_2$NR$^{11a}$CO—,
(l) —SO$_2$NR$^{11a}$CO$_2$—,
(m) —OCONR$^{11a}$SO$_2$—,
(n) —SO$_2$NR$^{11a}$CONR$^{11b}$—,
(o) —NR$^{11a}$CONR$^{11b}$SO$_2$—,
(p) —SO$_2$NR$^{11a}$SO$_2$—,
(q) —CONR$^{11a}$SO$_2$NR$^{11b}$—, or
(r) —NR$^{11a}$SO$_2$NR$^{11b}$CO—,
and pharmaceutically compatible salts of these compounds.

Another illustrative example of the specific embodiments described above is a compound of formula (VIa)

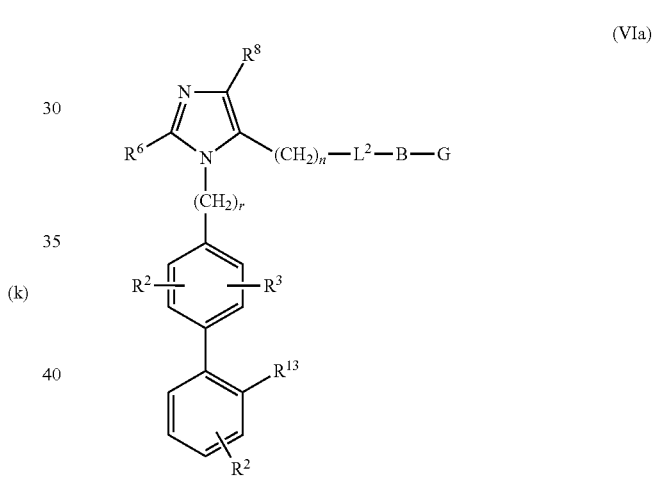

wherein
R$^2$ is independently
(a) H,
(b) halo (F, Cl, Br, I), or
(c) C$_1$-C$_4$-alkyl;
R$^3$ is
(a) H, or
(b) halo (F, Cl, Br, I);
R$^6$ is
(a) C$_1$-C$_{10}$ alkyl,
(b) C$_3$-C$_{10}$ alkenyl, or
(c) C$_3$-C$_{10}$ alkynyl;
R$^9$ is
(a) H,
(b) C$_1$-C$_5$-alkyl,
(c) aryl
(d) —(C$_1$-C$_4$-alkyl)-aryl, or
(e) heteroaryl;
R$^{10}$ is
(a) aryl,
(b) C$_3$-C$_7$-cycloalkyl,
(c) C$_1$-C$_4$-perfluoroalkyl, (d) $C_1$-$C_4$-alkyl, optionally substituted with a substituent selected from the group consisting of aryl, heteroaryl, —OH, —SH, $C_1$-$C_4$-alkyl, $C_1$-$C_4$-alkoxy, $C_1$-$C_4$-alkylthio, —$CF_3$, halo, —$NO_2$, —$CO_2R^{12}$, $C_1$-$C_4$alkylamino, $C_1$-$C_4$-dialkylamino, —$PO_3H_2$, or
(e) heteroaryl;
$R^{11}$, $R^{11a}$ and $R^{11b}$ are independently
(a) H,
(b) $C_1$-$C_6$-alkyl,
(c) $C_3$-$C_6$-cycloalkyl,
(d) aryl,
(e) —($C_1$-$C_5$-alkyl)-aryl, or
(f) heteroaryl;
$R^{13}$ is
(a) —$CO_2H$,
(b) —$CONHSO_2R^{19}$,
(c) —$CONHSO_2NHR^9$,
(d) —$NHCONHSO_2R^{10}$,
(e) —$NHSO_2R^{10}$,
(f) —$NHSO_2NHCOR^{10}$,
(g) —$SO_2NHR^9$,
(h) —$SO_2NHCOR^{10}$,
(i) —$SO_2NHCONHR^9$,
(j) —$SO_2NHCO_2R^{10}$, or

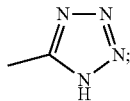 (k)

$R^{16}$ is
(a) H,
(b) $C_1$-$C_6$-alkyl, or
(c) benzyl, optionally substituted on the phenyl ring with 1-2 substituents selected from the group consisting of halo, $C_1$-$C_4$-alkyl, $C_1$-$C_4$-alkoxy or —$NO_2$;
$R^{28}$ is
(a) aryl, or
(b) heteroaryl;
$R^{29}$ is
(a) —CHO,
(b) —$CONH_2$,
(c) —NHCHO,
(d) —CO—($C_1$-$C_6$ perfluoroalkyl),
(e) —$S(O)_r$—($C_1$-$C_6$ perfluoroalkyl),
G is
(a) -$(T)_y$-$(B)_y$—$X^2$—$(B)_y$—$R^{28}$,
(b) -T-$(B)_y$—$R^{28}$,
(c) -$(T)_y$-$(B)_y$—$X^2$—B, or
(d) -T-$(B)_y$—$R^{29}$;
$L^2$ is —CO—, —$NR^{11a}CO$— or —$O_2C$—;
B is $C_1$-$C_6$ alkyl;
$X_2$ is
(a) —CO—,
(b) —O—,
(c) —$S(O)_r$—,
(d) —($C_2$-$C_4$-alkylene)-,
(e) CO, —$NR^{11a}CONR^{11b}$—
(f) —$CONR^{11a}$—,
(g) —$NR^{11a}CO$—,
(h) —$SO_2NR^{16}$—,
(i) —$NR^{16}SO_2$—,
(j) —$SO_2NR^{11a} SO_2$—,
(k) —$SO_2NR^{11a}CO_2$—,
(l) —$SO_2NR^{11a}CO_2$—,
(m) —$OCONR^{11a}SO_2$—,
(n) —$SO_2NR^{11a}CONR^{11b}$—,
(o) —$N^{R11a}CONR^{11b}SO_2$—,
(p) —$SO_2NR^{11a}SO_2$—,
(q) —$CONR^{11a}SO_2NR^{11b}$—, or
(r) —$NR^{11a}SO_2NR^{11b}CO$—, and pharmaceutically compatible salts of these compounds.

Illustrative of the compounds according to the specific embodiments mentioned above are the following:

1-((2'-((i-Amyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1H-imidazole, 1-((2'-((n-Butyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1H-imidazole, 1-((2'-((n-Propyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1,1-imidazole, 1-((2'-((n-Butyloxycarbonylamino)sulfonyl)-3-fluoro-(1,1'-biphenyl)-4-yl)methyl)-5-[2-(N-benzoyl-N-butylamino)ethylcarbonyl]-4-ethyl-2-propyl-1H-imidazole, 1-((2'-((n-Butyloxycarbonylamino)sulfonyl)-3-fluoro-(1,1'-biphenyl)-4-yl)methyl)-5-[2-(N-benzoyl-N-propylamino)ethylcarbonyl]-4-ethyl-2-propyl-1H-imidazole, 1-((2'-((n-Butyloxycarbonylamino)sulfonyl)-3-fluoro-(1,1'-biphenyl)-4-yl)methyl)-5-[2-(N-butyryl-N-propylamino)ethylcarbonyl]-4-ethyl-2-propyl-1H-imidazole, 1-((2'-((n-Butyloxycarbonylamino)sulfonyl)-3-fluoro-(1,1'-biphenyl)-4-yl)methyl)-5-[2-(N-butyryl-N-phenylamino)ethylcarbonyl]-4-ethyl-2-propyl-1H-imidazole, 1-((2'-((i-Amyloxycarbonylamino)sulfonyl)-3-fluoro-(1,1'-biphenyl)-4-yl)methyl)-5-[2-(N-butyryl-N-phenylamino)ethylcarbonyl]-4-ethyl-2-propyl-1H-imidazole, 1-((2'-((i-Amyloxycarbonylamino)sulfonyl)-3-fluoro-(1,1'-biphenyl)-4-yl)methyl)-5-[2-(N-isonicotinoyl-N-pyridin-3-ylamino)ethylcarbonyl]-4-ethyl-2-propyl-1H-imidazole, 1-((2'-((n-Butyloxycarbonylamino)sulfonyl)-3-fluoro-(1,1'-biphenyl)-4-yl)methyl)-5-[2-(N-isonicotinoyl-N-pyridin-3-ylamino)ethylcarbonyl]-4-ethyl-2-propyl-1H-imidazole, 1-((2'-((n-Butyloxycarbonylamino)sulfonyl)-3-fluoro-(1,1'-biphenyl)-4-yl)methyl)-5-[2-(N-nicotinoyl-N-pyridin-3-ylamino)ethylcarbonyl]-4-ethyl-2-propyl-1H-imidazole, 1-((2'-((i-Amyloxycarbonylamino)sulfonyl)-3-fluoro-(1,1'-biphenyl)-4-yl)methyl)-5-[2-(N-nicotinoyl-N-pyridin-3-ylamino)ethylcarbonyl]-4-ethyl-2-propyl-1H-imidazole, 1-((2'-((i-Amyloxycarbonylamino)sulfonyl)-3-fluoro-(1,1'-biphenyl)-4-yl)methyl)-5-[2-(N-nicotinoyl-N-pyridin-2-ylamino)ethylcarbonyl]-4-ethyl-2-propyl-1H-imidazole, 1-((2'-((i-Amyloxycarbonylamino)sulfonyl)-3-fluoro-(1,1'-biphenyl)-4-yl)methyl)-5-[2-(N-isonicotinoyl-N-phenylamino)ethylcarbonyl]-4-ethyl-2-propyl-1H-imidazole, 1-((2'-((i-Amyloxycarbonylamino)sulfonyl)-3-fluoro-(1,1'-biphenyl)-4-yl)methyl)-5-[2-(N-butyryl-N-pyridin-3-ylamino)ethylcarbonyl]-4-ethyl-2-propyl-1H-imidazole, 1-((2'-((i-Amyloxycarbonylamino)sulfonyl)-3-fluoro-(1,1'-biphenyl)-4-yl)methyl)-5-[2-(N-isobutyryl-N-pyridin-3-ylamino)ethylcarbonyl]-4-ethyl-2-propyl-1H-imidazole, 1-((2'-((n-Butyloxycarbonylamino)sulfonyl)-3-fluoro-(1,1'-biphenyl)-4-yl)methyl)-5-[2-(N-acetyl-N-pyridin-3-ylamino)ethylcarbonyl]-4-ethyl-2-propyl-1H-imidazole, 1-((2'-((i-Amyloxycarbonylamino)sulfonyl)-3-fluoro-(1,1'-biphenyl)-4-yl)methyl)-5-[2-(N-butyryl-N-pyridin-2-ylamino)ethylcarbonyl]-4-ethyl-2-propyl-1H-imidazole 1-((2'-((i-Amyloxycarbonylamino)sulfonyl)-(1,1'-biphenyl)-4-yl)methyl)-5-[2-(N-butyryl-N-pyridin-3-ylamino)ethylcarbonyl]-2-butyl-4-chloro-1H-imidazole, 1-((2'-((i-amyloxycarbonylamino)sulfonyl)-3-fluoro-(1,1'-biphenyl)-4-yl)methyl)-5-[2-(N-propionyl-N-pyridin-3-ylamino)ethylcarbonyl]-4-ethyl-2-propyl-1H-imidazole, 1-((2'-((i-Amyloxycarbonylamino)sulfonyl)(1,1'-biphenyl)-4-yl)methyl)-5-[2-(N-nicotinoyl-N-pyridin-3-ylamino)ethylcarbonyl]-4-ethyl-2-propyl-1H-imidazole, 1-((2'-((i-Amyloxycarbonylamino)sulfonyl)(1,1'-biphenyl)-4-yl)methyl)-5-[2(N-butyryl-N-pyridin-3-ylamino)ethylcarbonyl]-4-ethyl-2-propyl-1H-imidazole, 1-((2'-((n-Butyloxycarbonyl-amino)sulfonyl)-3-fluoro-(1,1'-biphenyl)-4-yl)methyl)-4-ethyl-5-(2-(2-phenoxyphenyl)ethylcarbonyl)-2-propyl-1H-imidazole, 4-[((5-(2-Benzoylbenzyl oxycarbonyl)-4-ethyl-2-n-propyl)imidazol-1-yl)methyl]-3-fluoro-2'-n-butyloxycarbonylaminosulfonyl-1,1'-biphenyl, 4-[((5-(2-Benzoylbenzyloxycarbonyl)-4-ethyl-2-n-propyl)imidazol-1-yl)methyl]-3-fluoro-2'42-phenyl)ethyloxycarbonylaminosulfonyl)-1,1'-biphenyl, 4-[((5-(2-Benzoylbenzyloxycarbonyl)-4-ethyl-2-n-propyl)imidazol-1-yl)methyl]-2'-((2-phenyl)ethyloxycarbonylaminosulfonyl)-1,1'-biphenyl, 4-[((5-(2-Benzoylbenzyloxycarbonyl)-4-ethyl-2-n-propyl)imidazol-1-yl)methyl]-3-fluoro-2'-n-butyloxycarbonylaminosulfonyl-1,1'-biphenyl, 4-[((5-(2-Benzoylbenzyloxycarbonyl)-4-ethyl-2-n-propyl)imidazol-1-yl)methyl]-3-fluoro-2'-n-isoamyloxycarbonylaminosulfonyl-1,1'-biphenyl, 4-[((5-(2-Benzoylbenzyloxycarbonyl)-4-ethyl-2-n-propyl)imidazol-1-yl)methyl]-2'-n-isoamyloxycarbonylaminosulfonyl-1,1'-biphenyl, 4-[((5-(2-Benzoylbenzyloxycarbonyl)-4-ethyl-2-n-propyl)imidazol-1-yl)methyl]-3-fluoro-2'-n-propyloxycarbonylaminosulfonyl-1,1'-biphenyl, 4-[((5-(2-Isoamyloxybenzyloxycarbonyl)-4-ethyl-2-n-propyl)imidazol-1-yl)methyl]-3-fluoro-2'-n-butyloxycarbonylaminosulfonyl-1,1'-biphenyl, 4-[((5-(2-Phenylaminocarbonyl)benzyloxycarbonyl-4-ethyl-2-n-propyl)imidazol-1-yl)methyl]-3-fluoro-2'-n-butyloxycarbonylaminosulfonyl-1,1'-biphenyl, 4-[((5-(2-Benzoylbenzyloxycarbonyl)-4-ethyl-2-n-propyl)imidazol-1-yl)methyl]-3-fluoro-2'-(1H-tetrazol-5-yl)-1,1'-biphenyl, 4-[((5-)2-trifluorophenyl)methylaminocarbonyl)-4-ethyl-2-n-propyl)imidazol-1-yl)methyl]-3-fluoro-2'-isoamyloxycarbonylaminosulfonyl-1,1'-biphenyl, N-butyl, N-benzyl-2-(aminocarbonyl)ethynylmethyl 4-ethyl-2-propyl-1-[[2'-(1H-tetrazol-5-yl)biphenyl-4-yl]methyl]imidazole-5-carboxylate, N,N-diphenyl-2-(aminocarbonyl)ethynylmethyl 4-ethyl-2-propyl-1-[[2'-(1H-tetrazol-5-yl)biphenyl-4-yl]methyl]imidazole-5-carboxylate, N-phenyl-2-(aminocarbonyl)ethyl-4-ethyl-2-propyl-1-[[2'-(1H-tetrazol-5-yl)biphenyl-4-yl]methyl]imidazole-5-carboxylate, N-butyl, N-benzyl-4-(aminocarbonyl)propyl-4-ethyl-2-propyl-1-[[2'-(1H-tetrazol-5-yl)biphenyl-4-yl]methyl]imidazole-5-carboxylate, N,N-dipentyl-4-(aminocarbonyl)propyl 4-ethyl-2-propyl-1-[[2'-(tetrazol-5-yl)biphenyl-4-yl]methyl]imidazole-5-carboxylate, 4-[(5-((2-benzoyl)phenylcarbonyloxymethyl)-4-chloro-2-n-propylimidazol-1-yl)methyl]-3-fluoro-2'-isoamyloxycarbonylaminosulfonylbiphenyl, 1-((2'-((n-butyloxycarbonylamino)sulfonyl)-3-fluoro-(1,1'-biphenyl)-4-yl)methyl)-2-(n-propyl)-4-ethyl-5-(2-(phenoxy)phenoxy)acetyl-1H-imidazole, In the embodiments described above for compounds according to formulae (IVa)-(VIa), when an alkyl substituent is mentioned, the normal alkyl structure is meant (e.g. butyl is n-butyl) unless otherwise specified. However, in the definition of radicals above (e.g. $R^3$), both branched and straight chains are included in the scope of alkyl, alkenyl and alkynyl.

In the embodiments described above for compounds according to formulae (IVa)-(VIa), the term "aryl" is meant to include phenyl, biphenyl, napthyl, or fluorenyl group optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —NH.sub.2, —NH($C_1$-$C_4$-alkyl), —N($C_1$-$C_4$-alkyl)$_2$. The term heteroaryl is meant to include unsubstituted, monosubstituted or disubstituted 5- to 10-membered mono- or bicyclic aromatic rings which can optionally contain from 1 to 3 heteroatoms selected from the group consisting of O, N, and S. Included in the definition of the group heteroaryl, but not limited to, are the following: pyridyl, pyridazinyl, pyrimidinyl, pyrazinyl, 1,3,5-triazinyl, furyl, thiophenyl, imidazolyl, oxazolyl, thiazolyl, benzofuranyl, benzothiophenyl, benzimidazolyl, benzoxazolyl, benzothiazolyl, indolin-2-onyl, indolinyl, indolyl, pyrrolyl, quinonlinyl and isoquinolinyl. Particularly preferred are 2-, 3-, or 4-pyridyl; 2-, or 3-furyl; 2-, or 3-thiophenyl; 2-, 3-, or 4-quinolinyl; or 1-, 3-, or 4-isoquinolinyl optionally substituted with one to three substituents selected from the group consisting of —OH, —SH, $C_1$-$C_4$-alkyl, $C_1$-$C_4$-alkoxy, —$CF_3$, halo, $NO_2$, —$CO_2H$, —$CO_2CH_3$, —$CO_2$-benzyl, —$NH_2$, —NH($C_1$-$C_4$alkyl), —N($C_1$-$C_4$-alkyl)$_2$. The term arylene is meant to include a phenyl, biphenyl, napthyl, or fluorenyl group which is used as a link for two groups to form a chain. Included in the definition of arylene, but not limited to, are the following isomeric linkers: 1,2-phenyl, 1,3-phenyl, 1,4-phenyl; 4,4'-biphenyl, 4,3'-biphenyl, 4,2'-biphenyl, 2,4'-biphenyl, 2,3'-biphenyl, 2,2'-biphenyl, 3,4'-biphenyl, 3,3'-biphenyl, 3,2'-biphenyl, 1,2-napthyl, 1,3-napthyl, 1,4-napthyl, 1,5-napthyl, 1,6-napthyl, 1,7-napthyl, 1,8-napthyl, 2,6-napthyl, 2,3-napthyl; 1,4-fluorenyl. Particularly preferred are 1,2-phenyl, 1,3-phenyl, 1,4-phenyl, 4,4'-biphenyl, 3,3'-biphenyl, and 2,2'-biphenyl optionally substituted with one to three substituents selected from the group consisting of —OH, —SH, $C_1$-$C_4$-alkyl, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$.

In the embodiments described above for compounds according to formulae (IVa)-(VIa), the term heteroarylene is meant to include unsubstituted 5- to 10-membered aromatic ring which can optionally contain from 1 to 3 heteroatoms selected from the group consisting of O, N, and S which is used as a link for two groups to form a chain. Included in the definition of the group heteroaryl, but not limited to, are the following: 2,3-pyridyl, 2,4-pyridyl, 2,5-pyridyl, 2,6-pyridyl, 3,4-pyridyl, 3,5-pyridyl, 3,6-pyridyl; 2,3-furyl, 2,4-furyl, 2,5-furyl; 2,3-thiophenyl, 2,4-thiophenyl, 2,5-thiophenyl; 4,5-imidazolyl, 4,5-oxazolyl; 4,5-thiazolyl; 2,3-benzofuranyl; 2,3-benzothiophenyl; 2,3-benzimidazolyl; 2,3-benzoxazolyl; 2,3-benzothiazolyl; 3,4-indolin-2-onyl; 2,4-indolinyl; 2,4-indolyl; 2,4-pyrrolyl; 2,4-quinolinyl, 2,5-quinolinyl, 4,6-quinolinyl; 3,4-isoquinolinyl, 1,5-isoquinolinyl. Particularly preferred are 2,3-pyridyl, 3,4-pyridyl, 2,3-furyl, 3,4-furyl 2,3-thiophenyl, 3,4-thiophenyl, 2,3-quinolinyl, 3,4-quinolinyl and 1,4-isoquinolinyl optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$alkyl), —N($C_1$-$C_4$alkyl)$_2$;

It should be noted in the foregoing structural formula, when a radical can be a substituent in more than one previously defined radical, that first radical ($R^{11}$, B or y) can be selected independently in each previously defined radical. For example, $R^1$ and $R^2$ can each be —$CONHOR^{12}$. $R^{12}$ need not be the same substituent in each of $R^1$ and $R^2$, but can be selected independently for each of them. Or if, for example, the same R group (let us take $R^2$, for instance) appears twice in a molecule, each of those R groups is independent of each other (one $R^2$ group may be —$CONHOR^{12}$, while the other $R^2$ group may be —CN).

In still other embodiments, the $AT_2$ receptor antagonist is selected from the compounds listed in U.S. Pat. No. 5,338,740 and especially in the compound claims of this patent, which a heterocyclic ring (hereafter referred to as "Het") is connected to an aryl or thienyl group (hereafter referred to as "Ar") via a carbobicyclic or heterobicyclic spacer group (hereafter referred to as "W"). Representative examples of such compounds are represented by the formula (VIIa):

Ar—W-Het (VIIa)

wherein:
Ar is selected from the group consisting of

and $X^1$, $X^2$, $X^3$ and $X^4$ are independently selected from $CR^2$ and nitrogen;
one of $X^5$ and $X^6$ is CH and the other is S;
$R^1$ is selected from the group consisting of $CO_2H$, —$NHSO_2CF_3$, —$CONHSO_2$—($C_1$-$C_8$)alkyl, $PO_3H_2$, $SO_3H$, —$CONHSO_2(C_6H_5)$, —$CONHSO_2CF_3$, tetrazole,

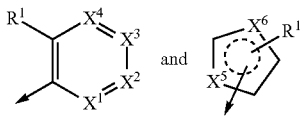

and —$SO_2NHCO_2$—($C_1$-$C_8$)alkyl;
$R^2$ is selected from hydrogen, ($C_1$-$C_8$)alkyl, ($C_2$-$C_{10}$)alkenyl, ($C_3$-$C_8$)cycloalkyl, halo, hydroxy, —O—($C_1$-$C_6$)alkyl, —S—($C_1$-$C_6$)alkyl, —SO—($C_1$-$C_6$)alkyl —$SO_2$—($C_1$-$C_6$)alkyl, —$NR^3R^4$, and phenyl, wherein said phenyl is optionally mono-, di- or tri-substituted with substituents independently selected from hydrogen, ($C_1$-$C_8$)alkyl, ($C_2$-$C_{10}$)alkenyl, ($C_3$-$C_8$)cycloalkyl, halo, ($C_1$-$C_6$)alkoxy, —S—($C_1$-$C_6$)alkyl, —SO—$C_1$-$C_6$)alkyl, —$SO_2$—($C_1$-$C_6$)alkyl, —O—($C_1$-$C_6$)alkyl, and —$NR^4R^4$;
$R^3$ and $R^4$ are independently selected from hydrogen, ($C_1$-$C_8$)alkyl, ($C_2$-$C_{10}$)alkenyl and ($C_1$-$C_8$)cycloalkyl, or $R^3$ and $R^4$, together with the nitrogen to which they are attached, form a cyclic 5-7 membered saturated or partially saturated carbocyclic or heterocyclic ring with one or two heteroatoms independently selected from nitrogen, oxygen and sulfur; and the dotted line represents that the ring containing $X^5$ and $X^6$ is aromatic:

W is a carbobicyclic or heterobicyclic ring system having the formula:

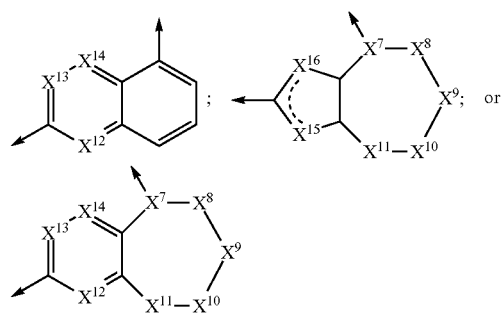

and $X^8$, $X^9$, $X^{10}$ and $X^{11}$ are present or absent, and each of $X^7$, $X^8$, $X^9$, $X^{10}$ and $X^{11}$ is independently selected from $CHR^5$, O, S, SO, $SO^2$, and $NR^6$;
$X^{12}$, $X^{13}$, and $X^{14}$ are independently selected from $CR^7$ or N;
$X^{15}$ and $X^{16}$ are independently selected from $CR^7$ and S;
$R^5$ is absent when the CH moiety of $CHR^5$ is connected to Het and when $R^5$ is present it is selected from hydrogen, ($C_1$-$C_8$)alkyl, ($C_2$-$C_{10}$)alkenyl, ($C_3$-$C_8$)cycloalkyl, —O—($C_1$-$C_6$)alkyl, and phenyl, wherein said phenyl is optionally mono-, di- or tri-substituted with substituents independently selected from hydrogen, ($C_1$-$C_8$)alkyl, ($C_2$-$C_{10}$)alkenyl, ($C_3$-$C_8$)cycloalkyl, halo, ($C_1$-$C_6$)alkoxy, —S—($C_1$-$C_6$)alkyl, —SO—($C_1$-$C_6$)alkyl, —$SO_2$—($C_1$-$C_6$)alkyl, —O—($C_1$-$C_6$)alkyl, and —$NR^3R^4$;
$R^6$ is selected from ($C_1$-$C_8$)alkyl, ($C_3$-$C_8$)cycloalkyl and phenyl, wherein said cycloalkyl is saturated or partially saturated and wherein said cycloalkyl may optionally contain a heteroatom selected from nitrogen, oxygen, and sulfur, and said phenyl is optionally mono-, di- or tri-substituted with substituents independently selected from hydrogen, ($C_1$-$C_8$)alkyl, ($C_1$-$C_{10}$)alkenyl, ($C_3$-$C_8$)cycloalkyl, halo, ($C_1$-$C_6$)alkoxy, —S—($C_1$-$C_6$)alkyl, —SO—($C_1$-$C_6$)alkyl, —$SO_2$—($C_1$-$C_6$)alkyl, —O—($C_1$-$C_6$)alkyl, and —$NR^3R^4$;
$R^7$ is selected from hydrogen, ($C_1$-$C_8$)alkyl, ($C_2$-$C_{10}$)alkenyl, ($C_3$-$C_8$)cycloalkyl, halo, hydroxy, —O—($C_1$-$C_6$)alkyl, —S—($C_1$-$C_6$)alkyl, —SO—($C_1$-$C_6$)alkyl, —$SO_2$-($C_1$-$C_6$)alkyl, —$NR^3R^4$, and phenyl, wherein said phenyl is optionally mono-, di- or tri-substituted with substituents selected from hydrogen, ($C_1$-$C_8$)alkyl, ($C_1$-$C_{10}$)alkenyl, ($C_3$-$C_8$)cycloalkyl, halo, ($C_1$-$C_6$)alkoxy, —S—($C_1$-$C_6$)alkyl, —SO—($C_1$-$C_6$)alkyl, —$SO_2$—($C_1$-$C_6$)alkyl, —O—($C_1$-$C_6$)alkyl, and —$NR^3R^4$;

and the dotted line represents that the ring containing $X^{15}$ and $X^{16}$ contain one or two double bonds; and Het is selected from the group consisting of:

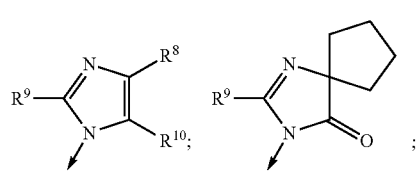

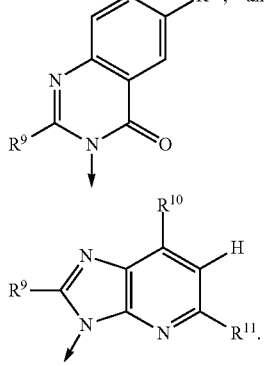

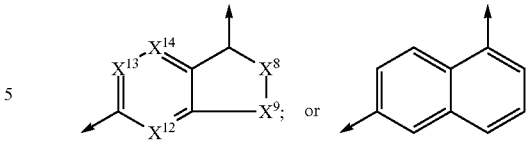

and $R^8$, $R^9$, $R^{10}$ and $R^{11}$ are independently selected from hydrogen, ($C_1$-$C_8$)alkyl, ($C_1$-$C_{10}$)alkenyl, ($C_3$-$C_8$)cycloalkyl, halo, ($C_1$-$C_8$)alkoxy, —S—($C_1$-$C_6$)alkyl, —SO—($C_1$-$C_6$)alkyl, —$CO_2H$, —$SO_2NR_3R_4$, —$NR_3R_4$, and phenyl, wherein said phenyl is optionally mono-, di-, or tri-substituted with halo, hydroxy, nitro, ($C_1$-$C_8$)alkyl, ($C_3$-$C_6$)cycloalkyl, ($C_1$-$C_7$)alkoxy, ($C_1$-$C_7$)alkylthio, and amino, wherein said amino is optionally mono- or di-substituted with ($C_1$-$C_7$)alkyl;

and wherein each occurrence of $R^3$ can be the same or different from any other occurrence of $R^3$, and each occurrence of $R^4$ can be the same or different from any other occurrence of $R^4$;

with the proviso that: (a) no more than two of $X^1$, $X^2$, $X^3$ and $X^4$ can be nitrogen; and (b) at least two of $X^7$, $X^8$, $X^9$, $X^{10}$ and $X^{11}$ are present;

and to pharmaceutically compatible salts thereof.

As used herein for compounds according to formula (VIIa):

the term "halo," unless otherwise indicated, includes chloro, fluoro, bromo and iodo;

the term "alkyl", unless otherwise indicated, includes saturated monovalent hydrocarbon radicals having straight, branched or cyclic moieties or combinations thereof, for example methyl, ethyl, n-propyl, isopropyl, n-butyl, isobutyl and t-butyl;

the term "alkenyl," unless otherwise indicated, means straight or branched unsaturated hydrocarbon radicals, for example, ethenyl, 1- or 2-propenyl, 2-methyl-1-propenyl and 1- or 2-butenyl;

the term "cycloalkyl," unless otherwise indicated, means a saturated carbocyclic radical, for example, cyclopropyl, cyclobutyl, cyclopentyl and cyclohexyl; and the term "alkoxy", unless otherwise indicated, includes O-alkyl groups wherein "alkyl" is defined as above.

In specific embodiments, compounds according to formula (VIIa) include those wherein W has the formula

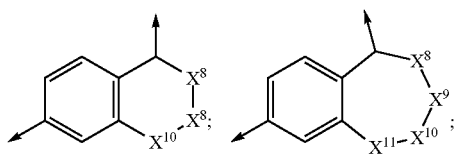

Examples of specific preferred compounds according to formula (VIIa) are:
2-butyl-5-chloro-1-{5-[2-(1H-tetrazol-5-yl)-phenyl]-indan-1-yl}-1H-imidazole-4-carboxylic acid ethyl ester;
2-butyl-5-chloro-1-{5-[2-(1H-tetrazol-5-yl)-phenyl]-indan-1-yl}-1H-imidazole-4-carboxylic acid;
2-butyl-3-{5-[2-(1H-tetrazol-5-yl)-phenyl]-indan-1-yl}-1,3-diazaspiro[4.4]non-1-en-4-one;
(2-butyl-5-chloro-1-{5-[2-(1H-tetrazol-5-yl)-phenyl]-indan-1-yl}-1H-imidazol-4-yl)methanol
2-ethyl-5,7-dimethyl-3-{5-[2-(1H-tetrazol-5-yl)-phenyl]-indan-1-yl}-3H-imidazole[4,5-b]pyridine;
(S)-2-ethyl-5,7-dimethyl-3-{5-[2-(1H-tetrazol-5-yl)-phenyl]-indan-1-yl}-3H-imidazo[4,5-b]pyridine;
(R)-2-ethyl-5,7-dimethyl-3-{5-[2-(1H-tetrazol-5-yl)-phenyl]-indan-1-yl}-3H-imidazol[4,5-b]pyridine;
2-ethyl-7-methyl-3-{5-[2-(1H-tetrazol-5-yl)-phenyl}-indan-1-yl}-3H-imidazo[4,5-b]pyridine;
5,7-dimethyl-2-propyl-3-{5-[2-(1H-tetrazol-5-yl)-phenyl]-indan-1-yl}-3H-imidazo[4,5-b]pyridine;
2-cyclopropyl-5,7-dimethyl-3-{5-[2-(1H-tetrazol-5-yl)-phenyl]-indan-1-yl}-3H-imidazo[4,5-b]pyridine;
2-butyl-5,7-dimethyl-3-{5-[2-(1H-tetrazol-5-yl)-phenyl]-indan-1-yl}-3H-imidazo[4,5-b]pyridine;
2-butyl-3-{5-[2-(1H-tetrazol-5-yl)-phenyl]-indan-1-yl}-3H-imidazo[4,5-b]pyridine;
2-[1-(2-ethyl-5,7-dimethyl-imidazo[4,5-b]pyridin-3-yl)-indan-5-yl-benzoic acid;
2-[5-(2-ethyl-5,7-dimethyl-imidazo[4,5-b]pyridin-3-yl)-5,6,7,8-tetrahydro-4H-naphthalen-2-yl]-benzoic acid;
2-ethyl-5,7-dimethyl-3-{6-[2-(1H-tetrazol-5-yl)-phenyl]-1,2,3,4-tetrahydro-4H-naphthalen-1-yl}-3H-imidazo[4,5-b]pyridine;
2-ethyl-5,7-dimethyl-3-{2-[2-(1H-tetrazol-5-yl)-phenyl]-6,7,8,9-tetrahydro-5H-benzocyclohepten-5-yl}-3H-imidazo[4,5-b]pyridine;
2-ethyl-5,7-dimethyl-3-{7-[2-(1H-tetrazol-5-yl)-phenyl]-chroman-4-yl}-3H-imidazo[4,5-b]pyridine;
2-ethyl-5,7-dimethyl-3-{3-[2-(1H-tetrazol-5-yl)-phenyl]-bicyclo[4.2.0]octa-1,3,5-trien-7-yl}-3H-imidazo[4,5-b]pyridine;
2-ethyl-5,7-dimethyl-3-{7-[2-(1H-tetrazol-5-yl)-phenyl]-chroman-4-yl}-3H-imidazo[4,5-b]pyridine;
2-ethyl-5,7-dimethyl-3-{3-[2-(1H-tetrazol-5-yl)-phenyl]-6,7-dihydro-5H-[1]pyridin-7-yl}-3H-imidazo[4,5-b]pyridine;
2-[5-(2-butyl-imidazo[4,5-b]pyridin-3-yl)-naphthalen-2-yl]-benzoic acid;
2-butyl-3-{6-[2-(1H-tetrazol-5-yl)-phenyl]-naphthalen-1-yl}3H-imidazo[4,5-b]pyridine; and
2-ethyl-5,7-dimethyl-3-{6-[2-(1H-tetrazol-5-yl)-phenyl-naphthalen-1-yl}-3 H-imidazo[4,5-b]pyridine.

Other compounds of according to formula (VIIa) include the following:
2-ethyl-5,7-dimethyl-3-{7-[2-(2H-tetrazol-5-yl)-phenyl]-thiochroman-4-yl}-3 H-imidazo[4,5-b]pyridine;
3-{1,1-dioxo-7-[2-(2H-tetrazol-5-yl)-phenyl]-thiochroman-4-yl}-2-ethyl-5,7-dimethyl-3H-imidazo[4,5-b]pyridine;

2-ethyl-5,7-dimethyl-3-{2-[2-(2H-tetrazol-5-yl)-phenyl]-5,6-dihydro-4H-thieno[2,3-b]thiopyran-4-yl}-3H-imidazo[4,5-b]pyridine;
2-ethyl-5,7-dimethyl-3-{2-[2-(2H-tetrazol-5-yl)-phenyl]-4,5,6,7-tetrahydrobenzo[b]thiophen-4-yl}-3H-imidazo[4,5-b]pyridine; P0 2-ethyl-5,7-dimethyl-3-{2-[2-(2H-tetrazol-5-yl)-phenyl]-5,6-dihydro-4H-cyclopenta[b]thiophen-4-yl}-3H-imidazo[4,5-b]pyridine;
2-ethyl-5,7-dimethyl-3-{6-[2-(2H-tetrazol-5-yl)-phenyl]-3,4-dihydro-2H-thieno[2,3-b]pyran-4-yl}-3H-imidazo[4,5-b]pyridine;
2-ethyl-5,7-dimethyl-3-{2-[2-(2H-tetrazol-5-yl)-phenyl]-6,7-dihydro-5H-[1]pyridin-5-yl}-3H-imidazo[4,5-b]pyridine;
5-(2-ethyl-5,7-dimethyl-imidazo[4,5-b]pyridin-3-yl)-2-[2-(2H-tetrazol-5-yl)-phenyl]-5,6,7,8-tetrahydro-quinoline;
4-(2ethyl-5,7-dimethyl-imidazo[4,5-b]pyridin-3-yl)-7-[2-(2H-tetrazol-5-yl)-phenyl]-3,4-dihydro-2H-thiopyrano[2,3-b]pyridine-1,1-dioxide;
2-ethyl-5,7-dimethyl-3-{2-[2-(2H-tetrazol-5-yl)-phenyl]-6,7-dihydro-5H-cyclopentapyrimidin-5-yl}-3H-imidazo[4,5-b]pyridine;
2-ethyl-5,7-dimethyl-3-{3-[2-(2H-tetrazol-5-yl)-phenyl]-6,7-dihydro-5H-[2]pyrindin-7-yl}-3H-imidazo[4,5-b]pyridine;
2-ethyl-5,7-dimethyl-3-{5-[3-(2H-tetrazol-5-yl)-thiophen-2-yl]-indan-1-yl}-3H-imidazo[4,5-b]pyridine;
2-ethyl-5,7-dimethyl-3-{5-[2-(2H-tetrazol-5-yl)-thiophen-3-yl]-indan-1-yl}-3H-imidazo[4,5-b]pyridine;
2-ethyl-5,7-dimethyl-3-{5-[4-(2H-tetrazol-5-yl)-thiophen-3-yl]-indan-1-yl}-3H-imidazo[4,5-b]pyridine;
2-ethyl-5,7-dimethyl-3-{5-[3-(2H-tetrazol-5-yl)-pyridin-4-yl]-indan-1-yl}-3H-imidazo[4,5-b]pyridine;
2-ethyl-5,7-dimethyl-3-{5-[4-(2H-tetrazol-5-yl)-pyridin-3-yl]-indan-1-yl}-3H-imidazo[4,5-b]pyridine;
2-ethyl-5,7-dimethyl-3-{5-[3-(2H-tetrazol-5-yl)-pyridin-2-yl]-indan-1-yl}-3H-imidazo[4,5-b]pyridine;
(2-butyl-5-chloro-3-{5-[2-(2H-tetrazol-5-yl)-phenyl]-indan-1-yl}-3H-imidazole-4-yl)methanol;
2-butyl-5-chloro-3-{5-[2-(2H-tetrazol-5-yl)-phenyl]-indan-1-yl}-3H-imidazole-4-carboxylic acid;
2-butyl-5-(1,1,2,2,2-pentafluoro-ethyl)-3-{5-[2-(2H-tetrazol-5-yl)-phenyl]-indan-1-yl}-3H-imidazole-4-carboxylic acid;
2-butyl-5-ethyl-3-{5-[2-(2H-tetrazol-5-yl)-phenyl]-indan-1-yl}-3H-imidazole-4-carboxylic acid;
2-ethoxy-3-{5-[2-(2H-tetrazol-5-yl)-phenyl]-indan-1-yl}-3H-benzoimidazole-4-carboxylic acid;
2-ethylsulfanyl-3-{5-[2-(2H-tetrazol-5-yl)-phenyl]-indan-1-yl}-3H-benzoimidazole-4-carboxylic acid;
N-benzoyl-2-[1-(2-ethyl-5,7-dimethyl-imidazo[4,5-b]pyridin-3-yl)-indan-5-yl]-benzenesulfonamide; and
N-{2-[1-(2-ethyl-5,7-dimethyl-imidazo[4,5-b]pyridin-3-yl)-indan-5-yl]-phenyl}-benzenesulfonamide.

In further embodiments, the $AT_2$ receptor antagonist is selected from $AT_2$ receptor antagonist peptides, illustrative examples of which include hexa-, hepta- and octapeptides represented by the formula:

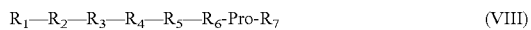

(VIII)

wherein:
$R_1$ is absent or is selected from hydrogen, succinyl, L-aspartyl, sarcosyl, L-seryl, succinamyl, L-propyl, glycyl, L-tyrosyl, $N_\alpha$-nicotinoyl-tyrosyl, or D- or L-asparagyl;
$R_2$ is selected from arginyl or N-benzoylcarbonyl arginyl;
$R_3$ is absent or valyl;
$R_4$ is absent or is selected from L-phenylalanyl or L-tyrosyl;
$R_5$ is selected from valyl, L-isoleucyl, L-alanyl or L-lysyl;
$R_6$ is selected from L-histidyl, L-isoleucyl, L-tyrosyl or p-aminophenylalanyl; and
$R_7$ is selected from L-alanine, L-tyrosine, L- or D-leucine, glycine, L-isoleucine or β-alanine residue.

and pharmaceutically acceptable salts of these peptides.

Representative examples according to formula (VIII) include, but are not limited to:

[SEQ ID NO: 1]
H-Asn-Arg-Val-Tyr-Val-His-Pro-Ala-OH;

[SEQ ID NO: 2]
H-Asn-Arg-Val-Tyr-Val-His-Pro-Leu-OH;

[SEQ ID NO: 3]
Succinyl-Arg-Val-Tyr-Val-His-Pro-Ala-OH;

[SEQ ID NO: 4]
H-Asp-Arg-Val-Tyr-Val-His-Pro-Ala-OH;

[SEQ ID NO: 5]
H-Arg-Val-Tyr-Val-His-Pro-Ala-OH;

[SEQ ID NO: 6]
H-Sar-Arg-Val-Tyr-His-Pro-Ala-OH;

[SEQ ID NO: 7]
H-Ser-Arg-Val-Tyr-His-Pro-Ala-OH;

[SEQ ID NO: 8]
Succinamyl-Arg-Val-Tyr-Val-His-Pro-Ala-OH;

[SEQ ID NO: 9]
H-Asn-Arg-Val-Tyr-Val-His-Pro-Gly-OH;

[SEQ ID NO: 10]
H-Asn-Arg-Val-Tyr-Val-His-Pro-Ile-OH;

[SEQ ID NO: 11]
H-Sar-Arg-Val-Tyr-Val-His-Pro-Gly-OH;

[SEQ ID NO: 12]
H-Pro-Arg-Val-Tyr-Val-His-Pro-Gly-OH;

[SEQ ID NO: 13]
H-Asn-Arg-Val-Tyr-Val-His-Pro-Gly-OH;

[SEQ ID NO: 14]
H-Sar-Arg-Val-Tyr-Val-His-Pro-β-Ala-OH;

[SEQ ID NO: 15]
H-Asn-Arg-Val-Tyr-Val-His-Pro-β-Ala-OH;

[SEQ ID NO: 16]
H-Gly-Arg-Val-Tyr-Val-His-Pro-Ala-OH;

[SEQ ID NO: 17]
H-Sar-Arg-Val-Tyr-Ile-His-Pro-Leu-OH;

[SEQ ID NO: 18]
H-Asn-Arg-Val-Tyr-Val-His-Pro-Leu-OH;

[SEQ ID NO: 19]
H-Sar-Arg-Val-Tyr-Ile-His-Pro-Ala-OH, also known as saralasin;

[SEQ ID NO: 20]
H-Asn-Arg-Val-Tyr-Ile-His-Pro-Ala-OH;

[SEQ ID NO: 21]
H-Asn-Arg-Val-Tyr-Ala-His-Pro-Ala-OH;

-continued

```
                                              [SEQ ID NO: 22]
H-Asp-Arg-Val-Phe-Ile-His-Pro-Tyr-OH, also known as Phe⁴-Tyr⁸-Ang II;

[SEQ ID NO: 23]
H-Asp-Arg-Val-Tyr-Ile-p-NH₂Phe-Pro-Phe-OH, also known as [p-NH₂Phe]⁶-Ang II;
and
                                              [SEQ ID NO: 24]
nicotinic acid-Tyr-(N-benzoylcarbonyl-Arg)-Lys- His-Pro-Ile-OH, also known as CGP-42112A;
```

In other embodiments, the $AT_2$ receptor antagonist is selected from antigen-binding molecules that are immuno-interactive with an $AT_2$ receptor polypeptide. Illustrative antigen-binding molecules include whole polyclonal antibodies. Such antibodies may be prepared, for example, by injecting an $AT_2$ receptor polypeptide or fragment thereof into a production species, which may include mice or rabbits, to obtain polyclonal antisera. Methods of producing polyclonal antibodies are well known to those skilled in the art. Exemplary protocols which may be used are described for example in Coligan et al., "Current Protocols In Immunology", (John Wiley & Sons, Inc, 1991), and Ausubel et al., (Current Protocols in Molecular Biology", John Wiley & Sons Inc, 1994-1998), in particular Section III of Chapter 11.

In lieu of the polyclonal antisera obtained in the production species, monoclonal antibodies may be produced using the standard method as described, for example, by Köhler and Milstein (1975, Nature 256, 495-497), or by more recent modifications thereof as described, for example, in Coligan et al., (1991, supra) by immortalizing spleen or other antibody-producing cells derived from a production species which has been inoculated with an $AT_2$ receptor polypeptide or fragment thereof.

The invention also contemplates as antigen-binding molecules Fv, Fab, Fab' and F(ab')$_2$ immunoglobulin fragments. Alternatively, the antigen-binding molecule may be in the form of a synthetic stabilized Fv fragment, a single variable region domain (also known as a dAbs), a "minibody" and the like as known in the art.

Also contemplated as antigen binding molecules are humanized antibodies. Humanized antibodies are produced by transferring complementary determining regions from heavy and light variable chains of a non human (e.g., rodent, preferably mouse) immunoglobulin into a human variable domain. Typical residues of human antibodies are then substituted in the framework regions of the non human counterparts. The use of antibody components derived from humanized antibodies obviates potential problems associated with the immunogenicity of non human constant regions. General techniques for cloning non human, particularly murine, immunoglobulin variable domains are described, for example, by Orlandi et al. (1989, Proc. Natl. Acad. Sci. USA 86: 3833). Techniques for producing humanized monoclonal antibodies are described, for example, by Jones et al. (1986, Nature 321:522), Carter et al. (1992, Proc. Natl. Acad. Sci. USA 89: 4285), Sandhu (1992, Crit. Rev. Biotech. 12: 437), Singer et al. (1993, J. Immun. 150: 2844), Sudhir (ed., Antibody Engineering Protocols, Humana Press, Inc. 1995), Kelley ("Engineering Therapeutic Antibodies," in Protein Engineering: Principles and Practice Cleland et al. (eds.), pages 399-434 (John Wiley & Sons, Inc. 1996), and by Queen et al., U.S. Pat. No. 5,693,762 (1997).

Illustrative antigen-binding molecules that are immuno-interactive with $AT_2$ receptor polypeptides and methods for their preparation are described by Nora et al. (1998, Am J Physiol. 275(4 Pt 2):H1395-403), Yiu et al. (1997, Regul Pept. 70(1):15-21), Reagan et al. (1993, Proc Natl Acad Sci USA. 90(17):7956-7960), Rakugi et al. (1997, Hypertens Res. 20(1):51-55) and Wang et al. (1998 Hypertension. 32(1): 78-83), and some are available commercially, such as but not limited to H-143 (Santa Cruz Biotechnology, Santa Cruz, Calif.), which is directed against amino acid residues 221-363 from the carboxy terminus of human $AT_2$, rAT2 (Ab #1), which is directed against an 18-residue C-terminal fragment of rat $AT_2$), rAT2 (Ab #2) which is directed against an 18-residue C-terminal fragment of rat $AT_2$) and rAT2 (Ab #3), which is directed against a 10-residue N-terminal fragment of rat $AT_2$ (Alpha Diagnostic International, Inc.—5415 Lost Lane, SA).

In still other embodiments, the $AT_2$ receptor antagonist is selected from nucleic acid molecules that inhibit or otherwise reduce the level or functional activity of an expression product of an $AT_2$ gene, illustrative examples of which include antisense molecules, ribozymes and RNAi molecules. Thus, the present invention contemplates antisense RNA and DNA molecules as well as ribozymes and RNAi molecules that function to inhibit the translation, for example, of Agtr2 mRNA. Antisense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of an Agtr2 gene, are desirable. Exemplary antisense oligonucleotides can be derived from any nucleic acid molecule that encodes an $AT_2$ receptor, such as those described in U.S. Pat. No. 5,556,780, and in U.S. Pat. Appl. Pub. No. 20030083339. Therapeutic methods utilizing antisense oligonucleotides have been described in the art, for example, in U.S. Pat. Nos. 5,627,158 and 5,734,033. Generally, antisense molecules comprise from about 8 to about 30 bases (i.e., from about 8 to about 30 linked nucleosides) and typically comprise from about 12 to about 25 bases.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of Agtr2 RNA sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both antisense RNA and DNA molecules and ribozymes may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to nucleic acid molecules may be introduced as a means of increasing intracellular stability and half-life. Possible modifications include but are not limited to the addition of flanking sequences of ribo- or deoxy-nucleotides to the 5' and/or 3' ends of the molecule or the use of artificial linkages rather than phosphodiesterase linkages within the oligodeoxyribonucleotide backbone. Illustrative modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Other agents that may be used to decrease the expression of an Agtr2 gene or the level and/or functional activity of an expression product of that gene include RNA molecules that mediate RNA interference (RNAi) of a Agtr2 gene or gene transcript. RNAi refers to interference with or destruction of the product of a target gene by introducing a single stranded, and typically a double stranded RNA (dsRNA), which is homologous to the transcript of the target gene. Thus, in one embodiment, dsRNA per se and especially dsRNA-producing constructs that encode an amino acid sequence corresponding to at least a portion of an $AT_2$ receptor polypeptide may be used to decrease its level and/or functional activity. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a target gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and Ketting, 2000, Current Opinion in Genetics and Dev. 10: 562-567). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are preferably at least about 100 nucleotides in length. RNA-encoding constructs that express a single RNA designed to form a dsRNA via internal folding are preferably at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In another embodiment, RNA molecules of about 21 to about 23 nucleotides, which direct cleavage of specific mRNA to which they correspond, as for example described by Tuschl et al. in U.S. Pat. Appl. Pub. No. 20020086356, can be utilised for mediating RNAi. Such 21-23 nt RNA molecules can comprise a 3' hydroxyl group, can be single-stranded or double stranded (as two 21-23 nt RNAs) wherein the dsRNA molecules can be blunt ended or comprise overhanging ends (e.g., 5', 3').

4. Identification of $AT_2$ Receptor Antagonists

The invention also features methods of screening for agents that antagonize an $AT_2$ receptor, including reducing the expression of an $AT_2$ gene (also known as an Agtr2 gene) or the level and/or functional activity of an expression product of that gene. Thus, a candidate agent identified according to these methods has an ability to reduce the biological activity or property of an $AT_2$ receptor polypeptide.

Candidate agents falling within the scope of the present invention include antagonistic antigen-binding molecules, and inhibitor peptide fragments, antisense molecules, ribozymes, RNAi molecules and co-suppression molecules. Other candidate agents include small organic compounds having a molecular weight of more than 50 and less than about 2,500 Dalton and will typically comprise functional groups necessary for structural interaction with proteins, particularly hydrogen bonding, and typically include at least an amine, carbonyl, hydroxyl or carboxyl group, suitably at least two of the functional chemical groups. Candidate agents often comprise cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule $AT_2$ receptor antagonists are generally advantageous because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (e.g., by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc to produce structural analogues.

Screening may also be directed to known pharmacologically active compounds and chemical analogues thereof.

In some embodiments, the methods comprise: (1) contacting a preparation with a test agent, wherein the preparation contains (i) a polypeptide comprising an amino acid sequence corresponding to at least a biologically active fragment of an $AT_2$ receptor, or to a variant or derivative thereof; or (ii) a polynucleotide comprising at least a portion of a genetic sequence that regulates an $AT_2$ gene, which is operably linked to a reporter gene; and (2) detecting a decrease in the level and/or functional activity of the polypeptide, or an expression product of the reporter gene, relative to a normal or reference level and/or functional activity in the absence of the test agent, which indicates that the agent antagonizes the $AT_2$ receptor.

In illustrative examples of this type, the methods comprise the steps of establishing a control system comprising an $AT_2$ receptor polypeptide and a ligand which is capable of binding to the polypeptide; establishing a test system comprising an $AT_2$ receptor polypeptide, the ligand, and a candidate compound; and determining whether the candidate compound inhibits or otherwise reduces the functional activity of the polypeptide by comparison of the test and control systems. Representative ligands can comprise a compound according to any one of formulae I-VIII, and in these embodiments, the functional activity screened can include binding affinity. In certain embodiments, the methods comprise (a) incubating an $AT_2$ receptor polypeptide with a ligand (e.g., angiotensin II) in the presence of a test inhibitor compound; (b) determining an amount of ligand that is bound to the $AT_2$ receptor polypeptide, wherein decreased binding of ligand to the $AT_2$ receptor polypeptide in the presence of the test inhibitor compound relative to binding in the absence of the test inhibitor compound is indicative of inhibition; and (c) identifying the test compound as an $AT_2$ receptor antagonist if decreased ligand binding is observed. In other embodiments, the methods comprise: (a) incubating a cell membrane, which comprises an $AT_2$ receptor polypeptide, with a first ligand (e.g., angiotensin II) in the presence of a test inhibitor compound; (b) optionally blocking any $AT_1$ receptors present on or in the membrane with a second ligand that binds specifically to the $AT_1$ receptor (e.g., losartan or candesartan) if the first ligand also binds to the $AT_1$ receptor; (c) determining an amount of first ligand that is bound to the membrane, wherein decreased binding of ligand to the membrane in the presence of the test inhibitor compound relative to binding in the absence of the test inhibitor compound is indicative of inhibition; and (d) identifying the test compound as $AT_2$ receptor antagonist if decreased first ligand binding is observed.

In other illustrative examples, a form of an $AT_2$ receptor polypeptide or a catalytic or immunogenic fragment or oligopeptide thereof, is used for screening libraries of compounds in any of a variety of drug screening techniques. The fragment employed in such a screening can be affixed to a solid support. The formation of binding complexes, between an $AT_2$ receptor polypeptide and the agent being tested, will be detected. In specific embodiments, an $AT_2$ receptor polypeptide comprises an amino acid sequence corresponding to any one of:

[SEQ ID NO: 25]
MKGNSTLATTSKNITSGLHFGLVNISGNNESTLNCSQKPSDKHLDAIP

ILYYIIFVIGFLVNIVVVTLFCCQKGPKKVSSIYIFNLAVADLLLLATLP

LWATYYSYRYDWLFGPVMCKVFGSFLTLNMFASIFFITCMSVDRYQSVIY

PFLSQRRNPWQASYIVPLVWCMACLSSLPTFYFRDVRTIEYLGVNACIMA

FPPEKYAQWSAGIALMKNILGFIIPLIFIATCYFGIRKHLLKTNSYGKNR

ITRDQVLKMAAAVVLAFIICWLPFHVLTFLDALAWMGVINSCEVIAVIDL

ALPFAILLGFTNSCVNPFLYCFVGNRFQQKLRSVFRVPITWLQGKRESMS

CRKSSSLREMETFVS (human AGTR2);

[SEQ ID NO: 26]
MKDNFSFAATSRNITSSRPFDNLNATGTNESAFNCSHKPSDKHLEAIP

VLYYMIFVIGFAVNIVVVSLFCCQKGPKKVSSIYIFNLALADLLLLATLP

LWATYYSYRYDWLFGPVMCKVFGSFLTLNMFASIFFITCMSVDRYQSVIY

PFLSQRRNPWQASYVVPLVWCMACLSSLPTFYFRDVRTIEYLGVNACIMA

FPPEKYAQWSAGIALMKNILGFIIPLIFIATCYFGIRKHLLKTNSYGKNR

ITRDQVLKMAAAVVLAFIICWLPFHVLTFLDALTWMGIINSCEVIAVIDL

ALPFAILLGFTNSCVNPFLYCFVGNRFQQKLRSVFRVPITWLQGKRETMS

CRKGSSLREMDTFVS (murine AGTR2);
and

[SEQ ID NO: 27]
MKDNFSFAATSRNITSSLPFDNLNATGTNESAFNCSHKPADKHLEAIP

VLYYMIFVIGFAVNIVVVSLFCCQKGPKKVSSIYIFNLAVADLLLLATLP

LWATYYSYRYDWLFGPVMCKVFGSFLTLNMFASIFFITCMSVDRYQSVIY

PFLSQRRNPWQASYVVPLVWCMACLSSLPTFYFRDVRTIEYLGVNACIMA

FPPEKYAQWSAGIALMKNILGFIIPLIFIATCYFGIRKHLLKTNSYGKNR

ITRDQVLKMAAAVVLAFIICWLPFHVLTFLDALTWMGIINSCEVIAVIDL

ALPFAILLGFTNSCVNPFLYCFVGNRFQQKLRSVFRVPITWLQGKRETMS

CRKSSSLREMDTFVS (rat AGTR2).

In still other illustrative examples, a plurality of different small test compounds are synthesized on a solid substrate, such as plastic pins or some other surface. The test compounds are reacted with an $AT_2$ receptor polypeptide, or fragments thereof. Bound polypeptide is then detected by methods well known to those of skill in the art. The polypeptide can also be placed directly onto plates for use in the aforementioned drug screening techniques.

In other illustrative examples, the methods comprise: contacting an $AT_2$ receptor polypeptide with individual members of a library of test samples; detecting an interaction between a test sample and an $AT_2$ receptor polypeptide; identifying a test sample that interacts with an $AT_2$ receptor polypeptide; and isolating a test sample that interacts with an $AT_2$ receptor polypeptide.

In each of the foregoing embodiments, an interaction can be detected spectrophotometrically, radiologically or immunologically. An interaction between $AT_2$ receptor polypeptide and a test sample can also be quantified using methods known to those of skill in the art.

In still other embodiments, the methods comprise incubating a cell (e.g., an endothelial cell such as a coronary endothelial cell (CEC), a PC12W cell, a SK-UT-1 cell, a 3T3 fibroblast cell or a NG108-15 cell), which naturally or recombinantly expresses an $AT_2$ receptor on its surface, in the presence and absence of a candidate agent under conditions in which the $AT_2$ receptor is able to bind an $AT_2$ receptor ligand, and the level of $AT_2$ receptor activation is measured by a suitable assay. For example, an $AT_2$ receptor antagonist can be identified by measuring the ability of a candidate agent to decrease $AT_2$ receptor activation in the cell from a baseline value in the presence of receptor ligand. In illustrative examples, PC12W cells are exposed to, or cultured in the presence of angiotensin II and in the presence and absence of the candidate agent under conditions in which the $AT_2$ receptor is active on the cells, and differentiation of the cells is measured. An agent tests positive for $AT_2$ receptor antagonism if it inhibits differentiation of the cells. In other illustrative examples, PC12W cells are exposed to, or cultured in the presence of angiotensin II and in the presence and absence of, the candidate agent under conditions in which the $AT_2$ receptor is active on the cells, and the level of nitric oxide or the level or functional activity of nitric oxide synthase in the cells is measured. An agent tests positive for $AT_2$ receptor antagonism if it inhibits nitric oxide or the level or functional activity of nitric oxide synthase. In still other illustrative examples, coronary endothelial cells are exposed to, or cultured in the presence of angiotensin II and in the presence and absence of, the candidate agent under conditions in which the $AT_2$ receptor is active on the cells, and expression of Zfhep, which is a protein associated with cell differentiation, in the cells is measured. An agent tests positive for $AT_2$ receptor antagonism if it inhibits Zfhep expression in the cells. In specific embodiments, any $AT_1$ receptors on the surface of the cells is blocked using an $AT_1$ receptor ligand such as losartan and candesartan.

5. Compositions

Another aspect of the present invention provides compositions for treating, preventing and/or relieving the symptoms of a neuropathic condition, comprising an effective amount of an $AT_2$ receptor antagonist and a pharmaceutically acceptable carrier and/or diluent.

Any known $AT_2$ receptor antagonist can be used in the methods of the present invention, provided that the $AT_2$ receptor antagonist are pharmaceutically active. A "pharmaceutically active" $AT_2$ receptor antagonist is in a form which results in the treatment and/or prevention of a neuropathic condition, including the prevention of incurring a symptom, holding in check such symptoms or treating existing symptoms associated with the neuropathic condition, when administered to an individual.

The effect of compositions of the present invention may be examined by using one or more of the published models of pain/nociception or of neuropathy, especially peripheral neuropathy, and more especially neuropathic pain that occurs secondary to mechanical nerve injury or a diabetes-induced nerve injury (PDN), known in the art. This may be demonstrated, for example using a model which assesses the onset and development of tactile allodynia, the defining symptom of neuropathic pain, as for example described herein. The analgesic activity of the compounds of this invention can be evaluated by any method known in the art. Examples of such methods include von Frey filaments (Chaplan et al., 1995, Anesthesiology 83: 775-85. are the Tail-flick test (D'Amour et al. 1941, J. Pharmacol. Exp. and Ther. 72: 74-79); the Rat Tail Immersion Model, the Carrageenan-induced Paw Hyperalgesia Model, the Formalin Behavioral Response Model (Dubuisson et al., 1977, Pain 4: 161-174), the Von Frey Filament Test (Kim et al., 1992, Pain 50: 355-363), the Radiant Heat Model, the Cold Allodynia Model (Gogas et al., 1997, Analgesia 3: 111-118), the paw pressure test (Randall and Selitto, 1957, Arch Int Pharmacodyn 111: 409-419) and the paw thermal test (Hargreaves et al., 1998, Pain 32: 77-88). An in vivo assay for measuring the effect of a test compound on the tactile allodynia response in neuropathic rats is described in the Experimental section of the Examples. Compositions which test positive in such assays are particularly useful for the prevention, reduction, or reversal of pain in a variety of pain-associated conditions or pathologies including cancer, and are especially useful for the prevention, reduction, or reversal of neuropathic pain found, for example, in diabetic patients.

The active compounds of the present invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutical compositions suitable for use in the present invention include compositions wherein the pharmaceutically active compounds are contained in an effective amount to achieve their intended purpose. The dose of active compounds administered to a patient should be sufficient to achieve a beneficial response in the patient over time such as a reduction in at least one symptom associated with a neuropathic condition, which is suitably neuropathic pain such as diabetic neuropathic pain or neuropathic pain that occurs secondary to nerve trauma or infection. The quantity of the pharmaceutically active compounds(s) to be administered may depend on the subject to be treated inclusive of the age, sex, weight and general health condition thereof. In this regard, precise amounts of the active compound(s) for administration will depend on the judgement of the practitioner. In determining the effective amount of the active compound(s) to be administered in the treatment or prophylaxis of the neuropathic condition, the physician may evaluate numbness, weakness, pain, and loss of reflexes. In any event, those of skill in the art may readily determine suitable dosages of the $AT_2$ receptor antagonists of the invention.

An effective amount of an $AT_2$ receptor antagonist is one that is effective for the treatment or prevention of a neuropathic condition, including the prevention of incurring a symptom, holding in check such symptoms (e.g., pain), and/or treating existing symptoms associated with the neuropathic condition. Modes of administration, amounts of $AT_2$ receptor antagonist administered, and $AT_2$ receptor antagonist formulations, for use in the methods of the present invention, are discussed below. Whether the neuropathic condition has been treated is determined by measuring one or more diagnostic parameters indicative of the course of the disease, compared to a suitable control. In the case of an animal experiment, a "suitable control" is an animal not treated with the $AT_2$ receptor antagonist, or treated with the pharmaceutical composition without the $AT_2$ receptor antagonist. In the case of a human subject, a "suitable control" may be the individual before treatment, or may be a human (e.g., an age-matched or similar control) treated with a placebo. In accordance with the present invention, the treatment of pain includes and encompasses without limitation: (i) preventing pain experienced by a subject which may be predisposed to the condition but has not yet been diagnosed with the condition and, accordingly, the treatment constitutes prophylactic treatment for the pathologic condition; (ii) inhibiting pain initiation or a painful condition, i.e., arresting its development; (iii) relieving pain, i.e., causing regression of pain initiation or a painful condition; or (iv) relieving symptoms resulting from a disease or condition believed to cause pain, e.g., relieving the sensation of pain without addressing the underlying disease or condition.

The methods of the present invention are suitable for treating an individual who has been diagnosed with a neuropathic condition, who is suspected of having a neuropathic condition, who is known to be susceptible and who is considered likely to develop a neuropathic condition, or who is considered likely to develop a recurrence of a previously treated neuropathic condition.

In some embodiments, and dependent on the intended mode of administration, the $AT_2$ receptor antagonist-containing compositions will generally contain about 0.000001% to 90%, about 0.0001% to 50%, or about 0.01% to about 25%, by weight of $AT_2$ receptor antagonist, the remainder being suitable pharmaceutical carriers or diluents etc. In some embodiments, a daily dose of the $AT_2$ receptor antagonist, PD-123,319, may be from about 0.01 to 6000 mg per day, from about 0.02 to 3000 mg per day or from 0.05 to 1500 mg per day. In other embodiments, a daily dose of the $AT_2$ receptor antagonist, L-159,686, may be from about 0.01 to 12000 mg per day, from about 0.02 to 6000 mg per day or from 0.05 to 3000 mg per day. In still other embodiments, a daily dose of the $AT_2$ receptor antagonist, PD-121,981, may be from about 0.001 µg to 6000 mg per day, from about 0.002 µg to 3000 mg per day or from 0.005 µg to 1500 mg per day. In some embodiments, a daily dose of the $AT_2$ receptor antagonist, PD-126,055, may be from about 0.001 µg to 100 mg per day, from about 0.002 µg to 50 mg per day or from 0.05 µg to 20 mg per day. In other embodiments, a daily dose of the $AT_2$ receptor antagonist, L-161,638, may be from about 0.05 µg to 10000 mg per day, from about 0.1 µg to 5000 mg per day or from 0.5 µg to 2500 mg per day. In other embodiments, a daily dose of the $AT_2$ receptor antagonist, L-163,579, may be from about 0.001 µg to 3000 mg per day, from about 0.002 µg to 1500 mg per day or from 0.005 µg to 750 mg per day. The dosage of the $AT_2$ receptor antagonist can depend on a variety of factors, such as mode of administration, the species of the affected subject, age and/or individual condition, and can be easily determined by a person of skill in the art using standard protocols.

Depending on the specific neuropathic condition being treated, the active compounds may be formulated and administered systemically, topically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, inhaled, intranasal, or intraocular injections. For injection, the therapeutic agents of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Alternatively, the compositions of the invention can be formulated for local or topical administration. In this instance, the subject compositions may be formulated in any suitable manner, including, but not limited to, creams, gels, oils, ointments, solutions and suppositories. Such topical compositions may include a penetration enhancer such as benzalkonium chloride, digitonin, dihydrocytochalasin B, capric acid, increasing pH from 7.0 to 8.0. Penetration enhancers which are directed to enhancing penetration of the active compounds through the epidermis are preferred in this regard. Alternatively, the topical compositions may include liposomes in which the active compounds of the invention are encapsulated.

The compositions of this invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the active compounds of the present invention can be formulated readily using pharmaceutically acceptable carriers well known in the art into dosages suitable for oral administration, which is also preferred for the practice of the present invention. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, eg. by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceuticals which can be used orally include push-fit capsules made of gelatine, as well as soft, sealed capsules made of gelatine and a plasticiser, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the active compounds of the invention may also include injecting or implanting controlled releasing devices designed specifically for this purpose or other forms of implants modified to act additionally in this fashion. Controlled release of an active compound of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes and/or microspheres.

The active compounds of the invention may be administered over a period of hours, days, weeks, or months, depending on several factors, including the severity of the neuropathic condition being treated, whether a recurrence of the condition is considered likely, etc. The administration may be constant, e.g., constant infusion over a period of hours, days, weeks, months, etc. Alternatively, the administration may be intermittent, e.g., active compounds may be administered once a day over a period of days, once an hour over a period of hours, or any other such schedule as deemed suitable.

The compositions of the present invention may also be administered to the respiratory tract as a nasal or pulmonary inhalation aerosol or solution for a nebuliser, or as a microfine powder for insufflation, alone or in combination with an inert carrier such as lactose, or with other pharmaceutically acceptable excipients. In such a case, the particles of the formulation may advantageously have diameters of less than 50 micrometers, suitably less than 10 micrometers.

In order that the invention may be readily understood and put into practical effect, particular preferred embodiments will now be described by way of the following non-limiting examples.

EXAMPLES

Example 1

Figure 2:
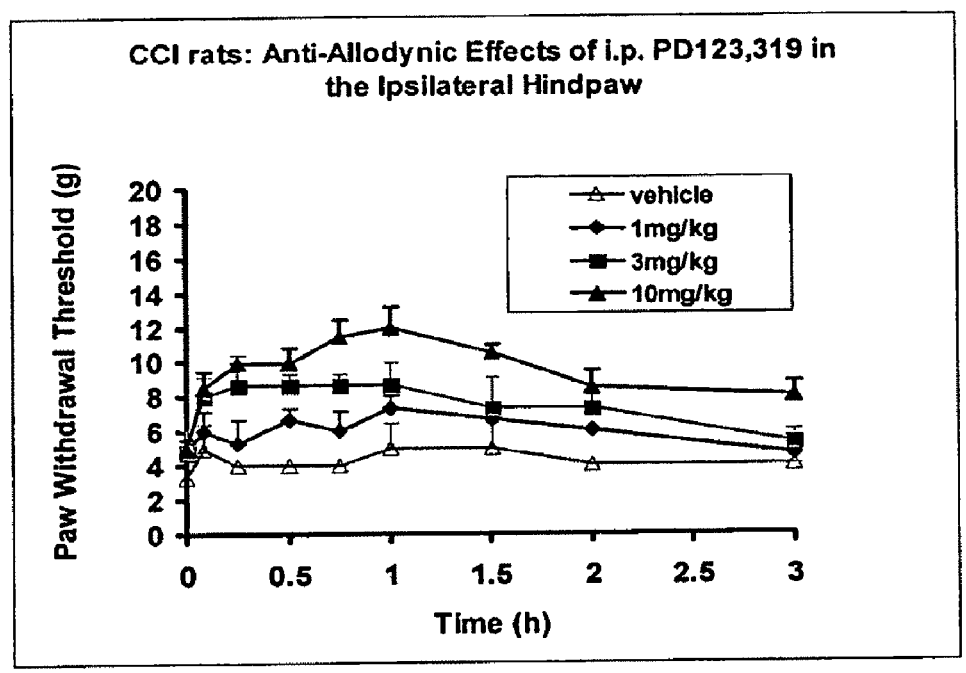
FIG. 2 is a graphical representation showing that single bolus doses of intraperitoneal (i.p.) PD-123,319 (1-10 mg/kg) produce dose-dependent (A) relief of tactile allodynia in the ipsilateral hindpaw of CCI-rats (n=3-4) and (B) antinociception in the contralateral hindpaw of the same animals. By contrast, i.p. administration of single bolus doses of vehicle did not produce significant anti-allodynia or antinociception in the ipsilateral and contralateral hindpaws respectively.
Figure 2:
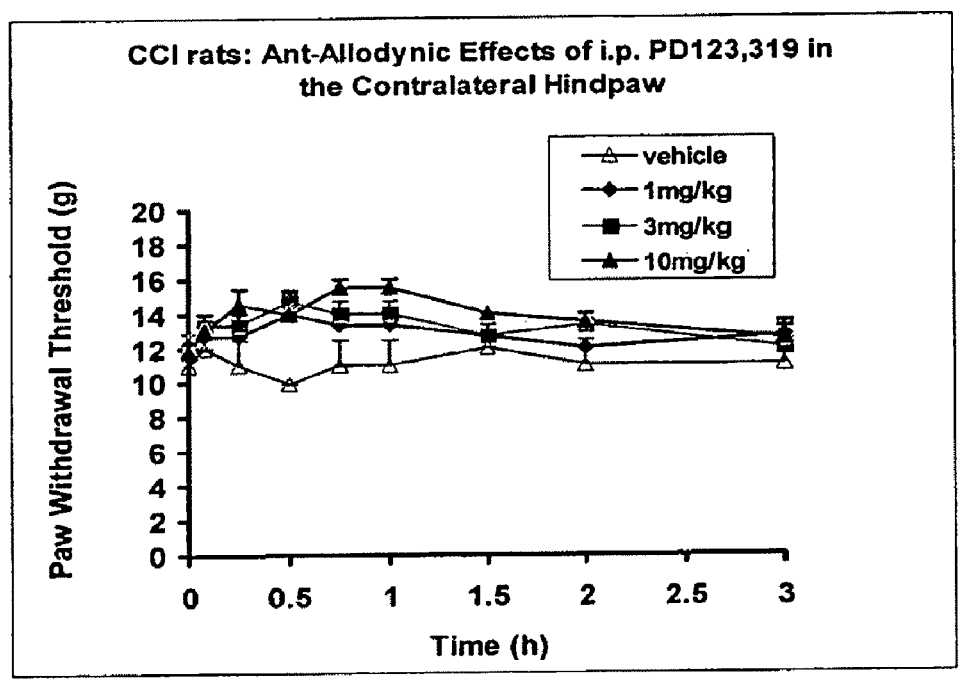

PD-123,319 Alleviates Neuropathic Pain in Rats with a Chronic Constriction Injury (CCI) of the Sciatic Nerve After administration of single bolus doses of i.v. the $AT_2$ receptor antagonist, PD-123,319, (0.1-0.3 mg/kg, n=2, FIG. 1) or the i.p. (1-10 mg/kg, n=3-4, FIG. 2) route to CCI-rats, there was dose-dependent relief of tactile allodynia (the defining symptom of neuropathic pain) in the ipsilateral (injured) hindpaws and antinociception in the contralateral hindpaws. By contrast, i.p. administration of vehicle (water for injection) did not produce significant relief of tactile allodynia or antinociception in the ipsilateral or contralateral hindpaws respectively.

Example 2

L-159,686 Alleviates Neuropathic Pain in CCI-Rats

Figure 3:
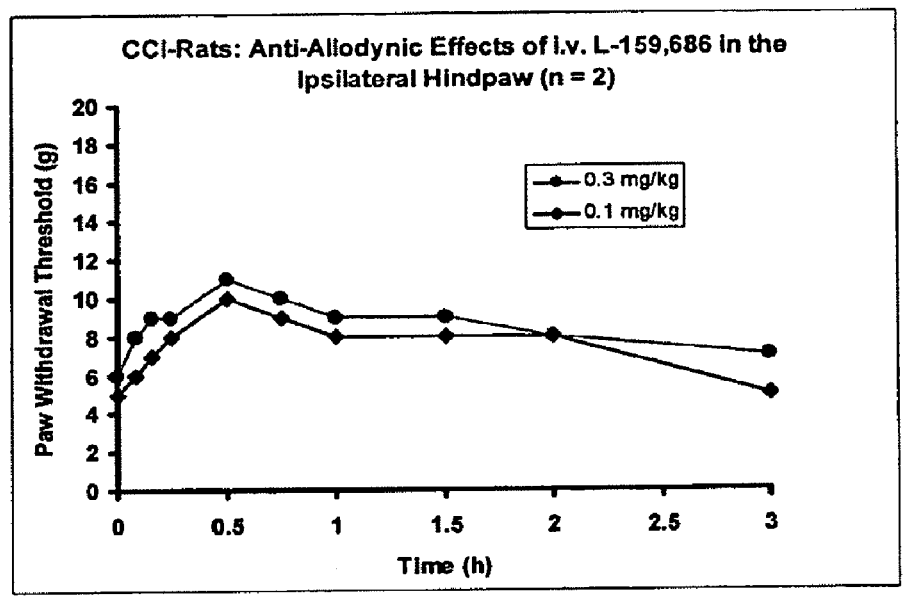
FIG. 3 is a graphical representation showing that single bolus doses of i.v. L-159,686 (0.1-0.3 mg/kg) produce dose-dependent (A) relief of tactile allodynia in the ipsilateral hindpaw of CCI-rats (n=2) and (B) antinociception in the contralateral hindpaw of the same animals.
Figure 3:
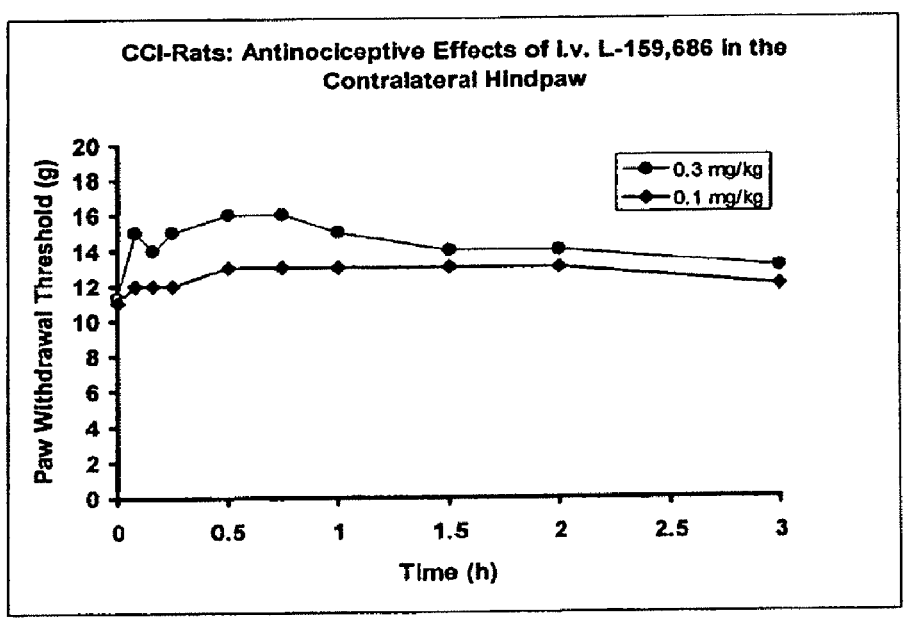

After administration of single bolus doses of the $AT_2$ receptor antagonist, L-159,686, (0.1-0.3 mg/kg) by the i.v. (n=2) route to CCI-rats, there was dose-dependent relief of tactile allodynia (the defining symptom of neuropathic pain) in the ipsilateral (injured) hindpaw and antinociception in the contralateral hindpaw (FIG. 3).

Example 3

PD-123,319 Alleviates Neuropathic Pain in STZ-Diabetic Rats

Figure 4:
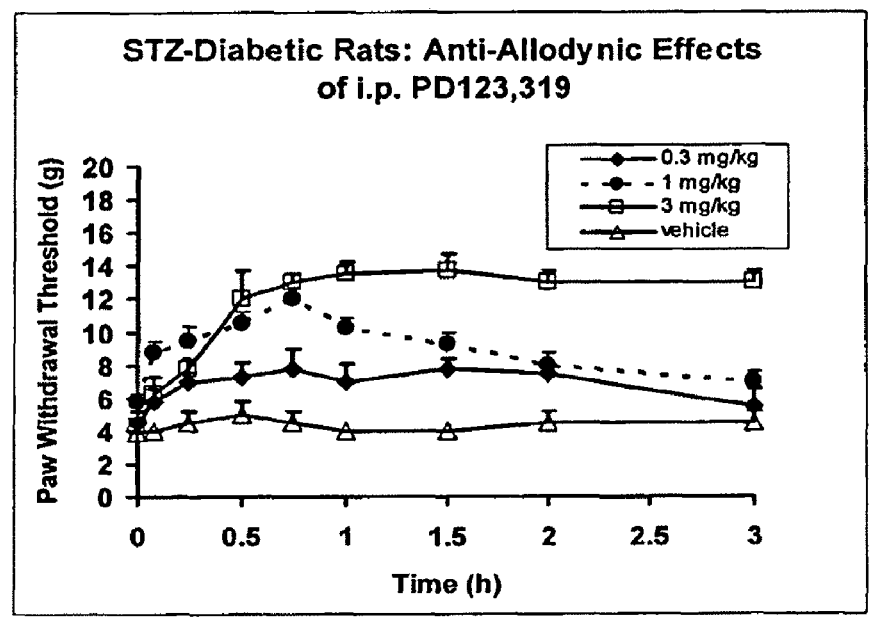
FIG. 4 is a graphical representation showing that single bolus doses of i.p. PD-123,319 (0.3-3.0 mg/kg) produce dose-dependent relief of tactile allodynia in the hindpaws of STZ-diabetic rats (n=4). By contrast, single bolus doses of i.p. vehicle did not produce significant relief of tactile allodynia in the hindpaws of STZ-diabetic rats.

Following i.p. injection of single bolus doses of PD-123, 319 (0.3-3.0 mg/kg) to STZ-diabetic rats (n=4) with fully developed tactile allodynia (~8-wks after induction of diabetes with STZ), there was dose-dependent relief of tactile allodynia, the defining symptom of painful diabetic neuropathy (FIG. 4). By contrast, i.p. injections of vehicle (water for injection) did not produce significant relief of tactile allodynia in STZ-diabetic rats.

Experimental for Examples 1-3

Drugs and Materials

Xylazine hydrochloride (Xylazil-20™), tiletamine HCl/zolazepam HCl combined (Zoletil 100®), and topical antibiotic powder (neomycin sulfate 2.5 mg, sulfacetamide sodium 100 mg, nitrofurazone 2 mg, phenylmercuric nitrate 0.05 mg and benzocaine 5 mg, in 50 g soluble powder) were purchased from Provet Qld Pty Ltd (Brisbane, Australia). Sodium benzylpenicillin (Benpen™) was purchased from the Royal Brisbane Hospital Pharmacy (Brisbane, Australia). Isoflurane (Isoflo™) was purchased from Abbott Australasia (Sydney, Australia), while medical grade $CO_2$ and $O_2$ were purchased from BOC Gases Ltd. (Brisbane, Australia). Streptozotocin, citric acid and trisodium citrate were purchased from Sigma-Aldrich (Sydney, Australia). Blood glucose meters (Precision Q.I.D™) and glucose testing electrodes (Precision Plus™) were purchased from the Campus Pharmacy at The University of Queensland (Brisbane, Australia). Sterile siliconized silk sutures (Dysilk™) were obtained from Dynek Pty Ltd (Adelaide, South Australia). Single lumen polyethylene tubing (0.5-mm internal diameter) was purchased from Critchley Electrical Products Pty Ltd (Auburn, Australia). PD-123,319, as described in U.S. Pat. No. 4,812,462, was synthesized in the laboratory of Dr Craig Williams, Dept of Chemistry, The University of Queensland (Brisbane, Australia). L-159,686, as described in International Publication No. WO 92/20661, was purchased from Chembridge Corporation (San Diego, USA).

Rats with a Chronic Constriction Injury (CCI) of the Sciatic Nerve

Adult male Sprague-Dawley (SD) rats were anaesthetized with Zoletil 100® (0.09 ml/200 g) and Xylazil-20™ (0.1 mL/200 g) administered by intraperitoneal (i.p.) injection, and a chronic constriction injury (CCI) of the sciatic nerve was produced according to the method of Bennett and Xie (1988). Briefly, the left common sciatic nerve was exposed at mid-thigh level by blunt dissection through the biceps femoris. Proximal to the trifurcation, 10 mm of nerve was freed of adhering tissue and four loose ligatures (3.0 silk) were tied around the sciatic nerve (≈1 mm apart). The incision was closed in layers. After surgery, rats received benzylpenicillin (60 mg s.c.) to prevent infection and were kept warm during surgical recovery. Rats were housed singly for 10-14 days prior to AT2 receptor antagonist or vehicle (normal saline) administration. After CCI-surgery, rats were inspected daily with regard to posture of the affected hindpaw, exploring behavior, body weight and water intake, and any signs of autotomy.

Induction of Diabetes with Streptozotocin

Adult male SD rats were anaesthetized in a manner similar to that described above, to facilitate insertion of a polyethylene cannula (previously filled with 0.1 ml of sterile saline) into the right common jugular vein. Jugular vein cannulae were tested for correct placement by the withdrawal of a small amount of blood. Diabetes was induced following an acute i.v. injection of streptozotocin (STZ) (80 mg/kg) in 0.1 M citrate buffer (pH 4.5) into the jugular vein. Diabetes was confirmed by monitoring the water intake and blood glucose concentration in individual rats. Blood glucose was monitored using either (Glucostix™) or a Precision QID™ test kit. Consistent with previous studies in the literature (Calcutt et al., 1996, Pain. 68(2-3):293-9), rats that drank more than 100 mL of water per day by 10 days post-STZ injection, were classified as diabetic, and only rats with blood glucose concentrations exceeding 15 mM were included in the subsequent experiments. By comparison, the water intake of control non-diabetic rats was approximately 20 mL per day and blood glucose concentrations were in the range 5-6 mM, consistent with the literature (Calcutt et al., 1996, supra).

Drug Dosing Regimens

Whilst under light anaesthesia with $CO_2/O_2$ (50:50%), CCI-rats or STZ-diabetic rats received a single bolus injection (200 µL) of one $AT_2$ receptor antagonist (PD123,319 or L-159,686) by the intravenous (i.v.) or the intraperitoneal (i.p.) route, using a 250 µL Hamilton syringe. The test compounds were administered to CCI-rats at 14 days after CCI-surgery and to STZ-diabetic rats at approximately 8-wks after the induction of diabetes with STZ. Relief of tactile (mechanical) allodynia, the defining symptom of neuropathic pain, by each of the test agents, PD123,319 or L-159,686, was quantified using calibrated von Frey filaments as described below.

Assessment of Antinociception

Tactile allodynia was quantified using calibrated von Frey filaments. Rats were placed in wire mesh testing cages (20 cm×20 cm×20 cm) and allowed to acclimatise for approximately 15-30 min. Von Frey filaments were used to determine the lowest mechanical threshold required for a brisk paw withdrawal reflex. Briefly, the filament that produced the lowest force was applied to the plantar surface of the hindpaw until the filament buckled slightly. Absence of a response after 5 s prompted use of the next filament in an ascending sequence. Filaments used produced a buckling weight of 2, 4, 6, 8, 10, 12, 14, 16, 18 and 20 g and these were calibrated prior to each testing session. A score of 20 g was given to animals that did not respond to any of the von Frey filaments.

For CCI-rats, baseline von Frey paw withdrawal thresholds (PWTs) were quantified prior to CCI-surgery, and at 14 days post-surgery immediately prior to drug administration. For STZ-diabetic rats, baseline von Frey PWT values were determined prior to the induction of diabetes with STZ and at 1-2 weekly intervals thereafter for 8 weeks to document the temporal development of tactile allodynia. For all rats, baseline PWTs were the mean of three readings taken ≈5 min apart before drug administration and were determined separately for each hindpaw. After administration of each test compound, von Frey PWTs were determined at the following post-dosing times: 0.08, 0.25, 0.5, 0.75, 1, 1.25, 1.5, 2 and 3 h.

Data Analysis

Paw withdrawal thresholds (PWTs; g) were plotted against time to construct response versus time curves for each of the two test compounds (PD123,319 and L-159,686) for each dose and dosing route.

Example 4

PD-121,981 Relieves Tactile Allodynia in the STZ-Diabetic Rat Model of PDN

Figure 5:
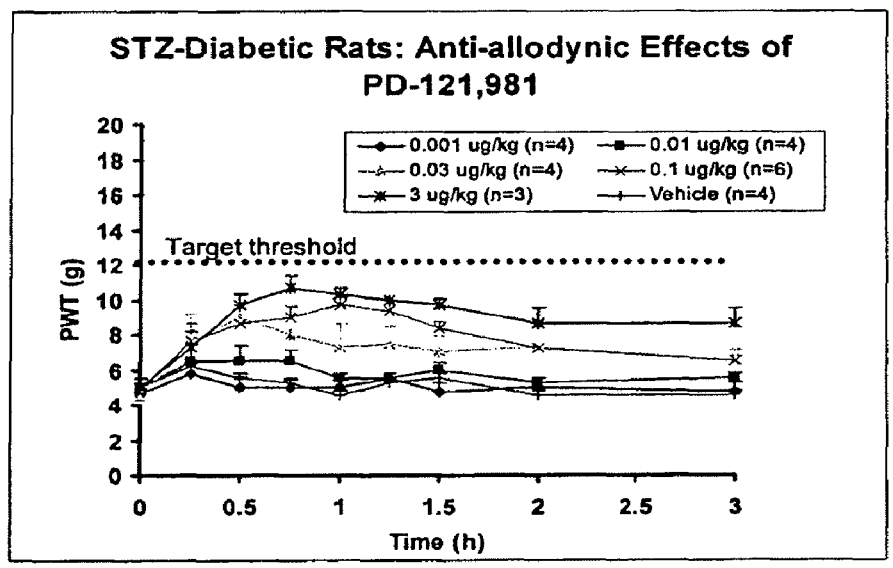
FIG. 5 is a graphical representation showing that single bolus i.p. doses of PD-121,981 (0.001-3 µg/kg) produce dose-dependent relief of tactile allodynia in STZ-diabetic rats.

After administration of i.p. bolus doses of PD-121,981 (0.001 to 3.0 µg/kg) to STZ-diabetic rats, there was dose-dependent relief of tactile allodynia with a rapid onset of action (FIG. 5). Peak anti-allodynia was achieved at 0.5-1.0 h post-dosing. For doses in the range 0.03-3.0 µg/kg, the duration of action was >3 h. Consistent with expectations, bolus doses of vehicle did not produce significant anti-allodynia.

Figure 6:
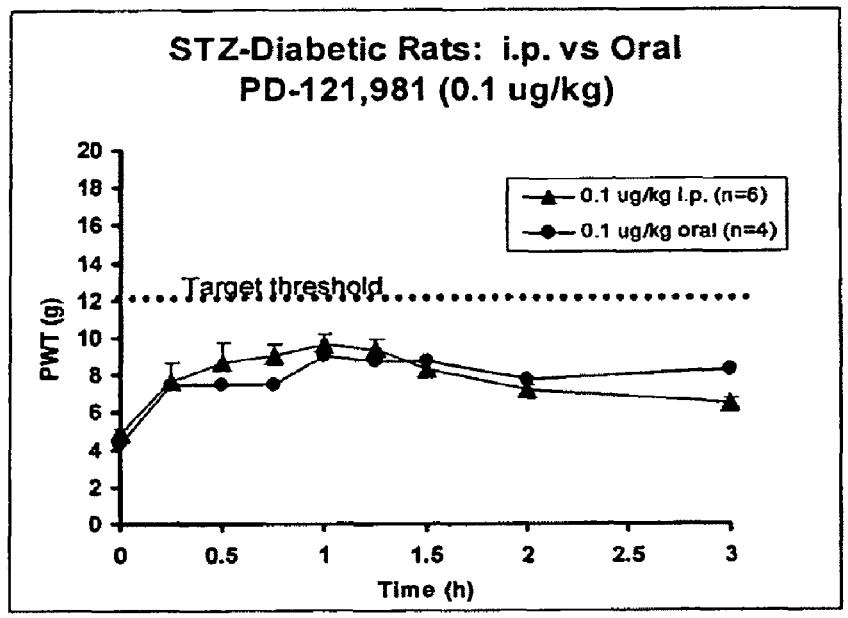
FIG. 6 is a graphical representation showing that the extent and duration of the anti-allodynic effects produced by single bolus i.p. and oral doses of PD-121,981 (0.1 µg/kg) are similar for the two routes of administration in STZ-diabetic rats.

Following oral administration of bolus doses of PD-121,981 (0.1 µg/kg) to STZ-diabetic rats, the extent and duration of the anti-allodynic response was similar to that produced by the same dose of PD-121,981 administered to STZ-diabetic rats by the i.p. route (FIG. 6). Irrespective of dosing route, the duration of action exceeded 3 h (FIG. 6).

Example 5

PD-126,055 Relieves Tactile Allodynia in the STZ-Diabetic Rat Model of PDN

Figure 7:
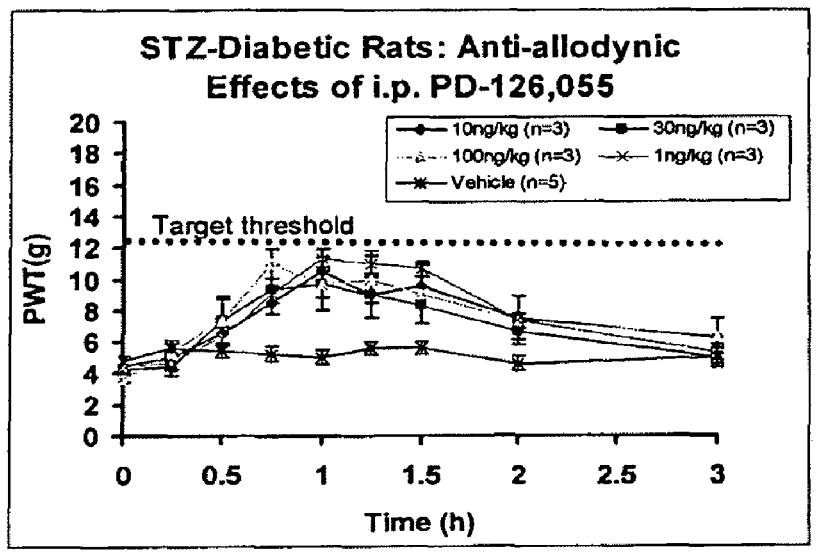
FIG. 7 is a graphical representation showing that single bolus i.p. doses of PD-126,055 (1.0-100 ng/kg) produced significant relief of tactile allodynia in STZ-diabetic rats.

Administration of i.p. bolus doses of PD-126,055 (1.0 to 100 ng/kg) to STZ-diabetic rats, produced significant relief of tactile allodynia (FIG. 7). The onset of action was at ~0.5 h post-dosing and peak anti-allodynia was achieved at ~0.75-1.0 h post-dosing. For the doses tested, the duration of action was in the range 2-3 h. Consistent with expectations, bolus doses of vehicle did not produce significant anti-allodynia.

Example 6

Figure 8:
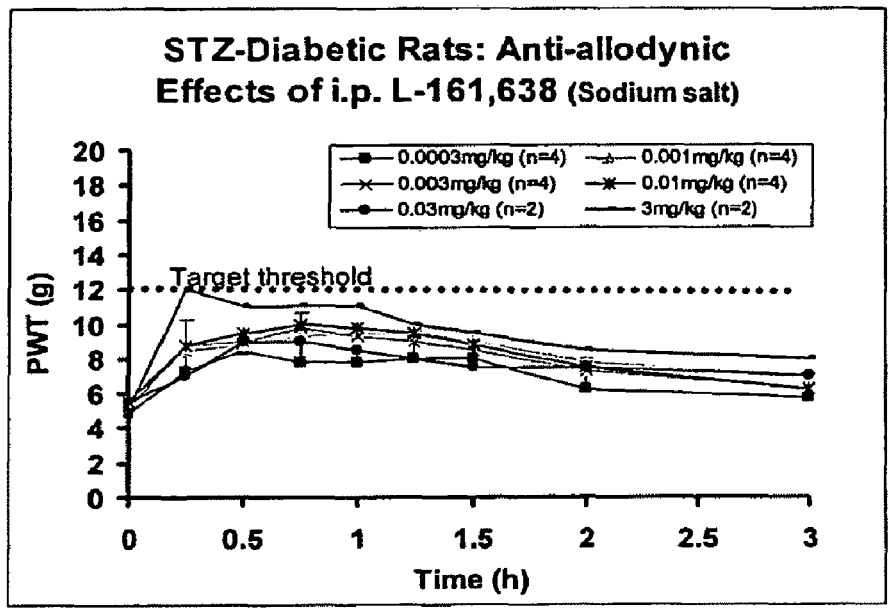
FIG. 8 is a graphical representation showing that single bolus i.p. doses of L-161,638 (sodium salt) (0.0003-3 mg/kg) produce dose-dependent relief of tactile allodynia in STZ-diabetic rats.

Sodium Salt of L-161,638 Relieves Tactile Allodynia in the STZ-Diabetic Rat Model of PDN Following i.p. administration of bolus doses of L-161,638 (0.0003 to 3 mg/kg) to STZ-diabetic rats, there was a rapid onset of relief of tactile allodynia with peak effects observed at 0.25-0.75 h post-dosing (FIG. 8). For doses in the range 0.0003-0.03 µg/kg, the duration of action was ~3 h. For the 3 mg/kg dose, the duration of action was >3 h.

Example 7

L-163,579 Relieves Tactile Allodynia in the STZ-Diabetic Rat Model of PDN

Figure 9:
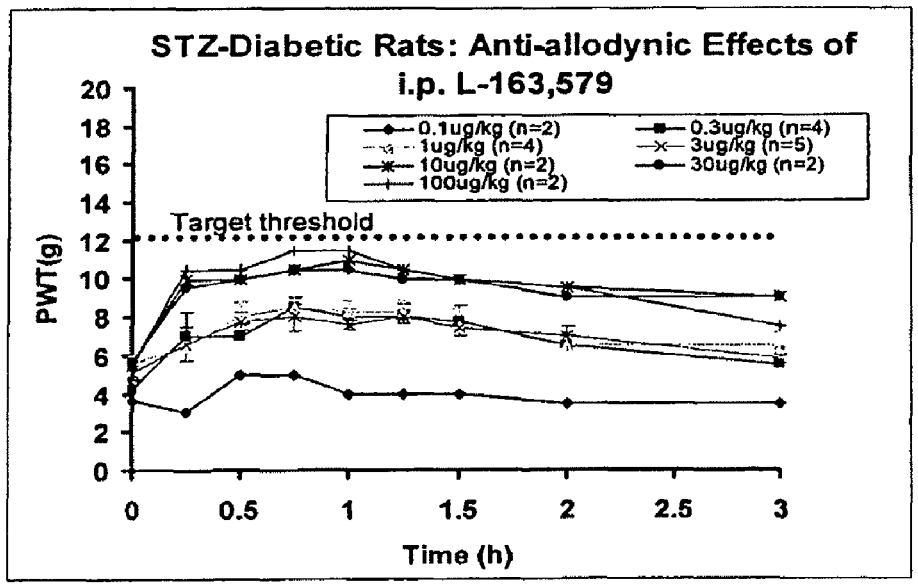
FIG. 9 is a graphical representation showing that single bolus i.p. doses of L-163,579 (0.1-10 µg/kg) produce dose-dependent relief of tactile allodynia in STZ-diabetic rats. Further increasing the dose of L-163,579 (30-100 µg/kg) produce similar responses to those evoked by the 10 µg/kg dose.

After i.p. administration of bolus doses of L-163,579 (0.1 to 10 µg/kg) to STZ-diabetic rats, there was dose-dependent relief of tactile allodynia characterized by a rapid onset of action (FIG. 9). Peak anti-allodynia was observed at 0.5-1 h post-dosing (FIG. 9) and the duration of action exceeded 3 h for the majority of the doses tested.

Example 8

L-159,686 Relieves Tactile Allodynia in the STZ-Diabetic Rat Model of PDN

Figure 10:
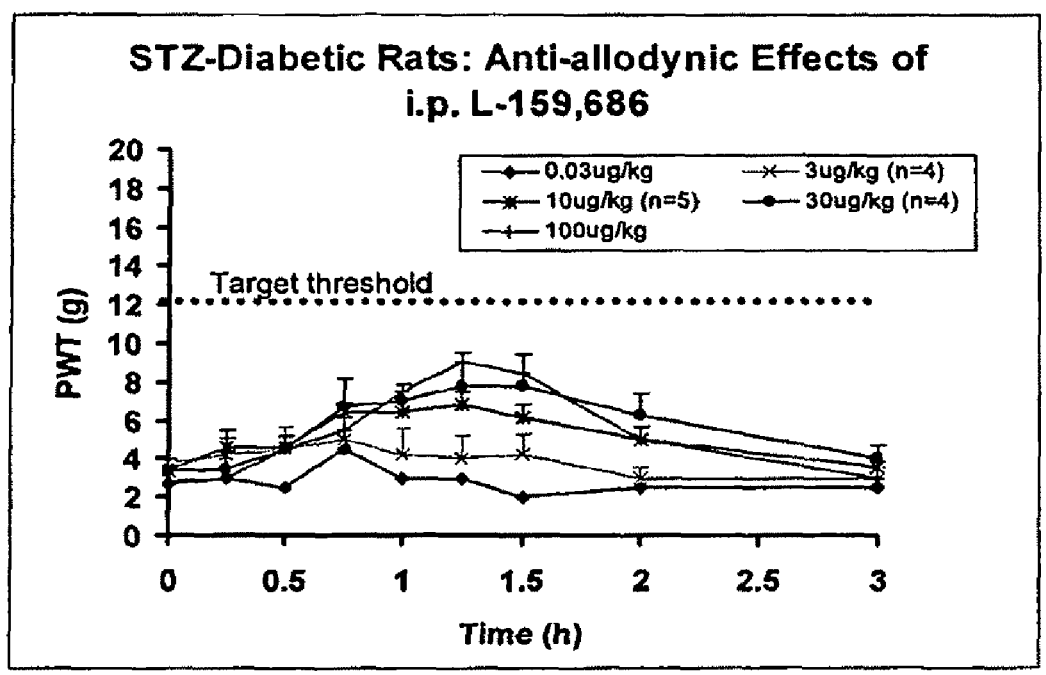
FIG. 10 is a graphical representation showing that single bolus i.p. doses of L-159,686 (0.03-10 µg/kg) produce dose-dependent relief of tactile allodynia in STZ-diabetic rats. Further increasing the dose to 30 and 100 µg/kg did not appear to significantly alter the magnitude or the duration of the anti-allodynic response.

Following i.p. administration of bolus doses of L-159,686 (0.03 to 10 µg/kg) to STZ-diabetic rats, there was dose-dependent relief of tactile allodynia (FIG. 10) but the onset of action was relatively slow with peak effects occurring at ~1.25 h post-dosing. Escalation of the doses to 30 and 100 µg/kg did not produce a faster onset of action and it did not increase the extent or the duration of the anti-allodynic response. For the doses investigated, the duration of action was 2-3 h.

Example 9

PD-121,981 Relieves Tactile Allodynia in CCI Rats

Figure 11:
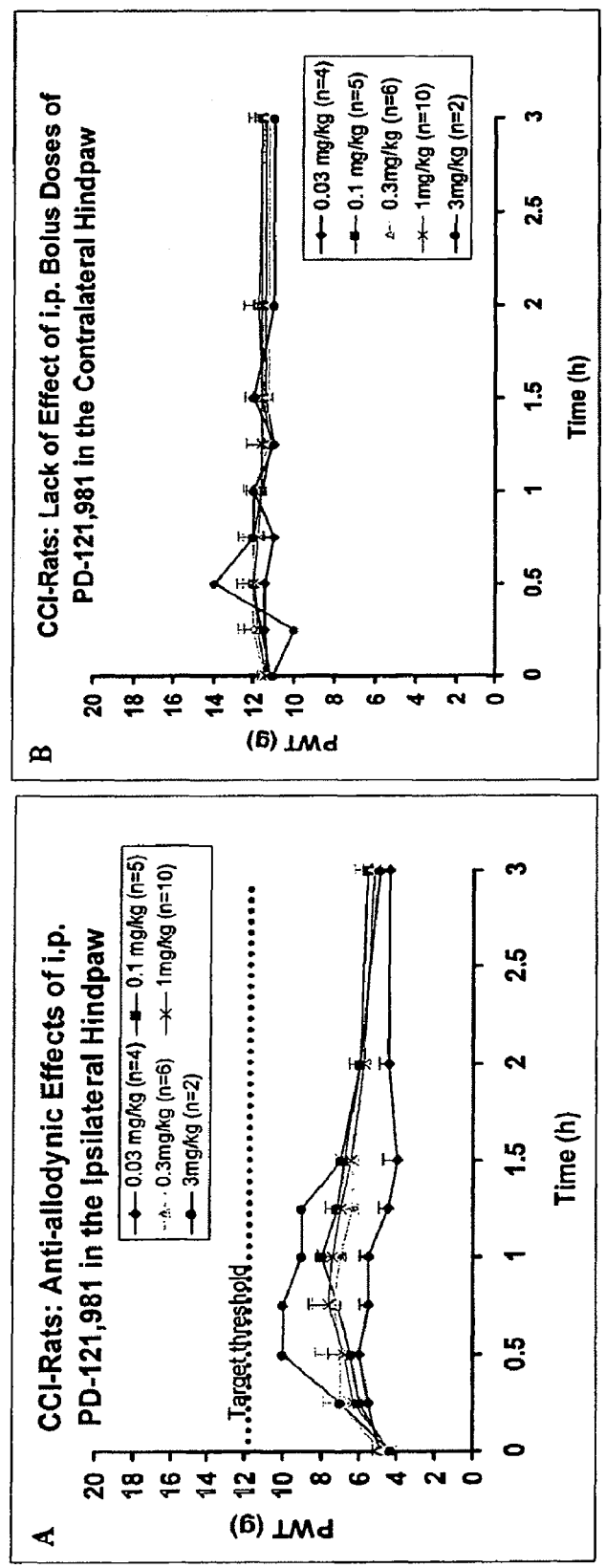
FIG. 11 is a graphical representation showing that: (A) single i.p. bolus doses of PD-121,981 (0.03-3 mg/kg) produce dose-dependent relief of tactile allodynia in the ipsilateral hindpaw of CCI-rats; and that (B) the same doses of PD-121,981 produces insignificant antinociception in the contralateral hindpaws of the same animals.
Figure 12:
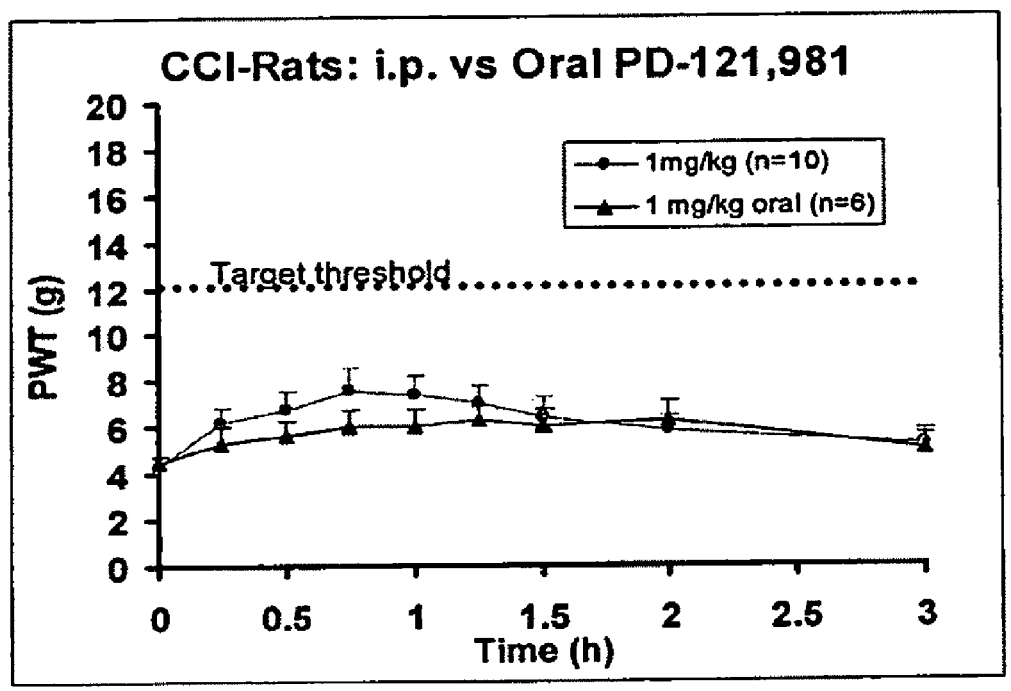
FIG. 12 is a graphical representation showing that the extent and duration of the anti-allodynic effects produced by single bolus i.p. and oral doses of PD-121,981 (1 mg/kg) are similar for the two routes of administration in CCI-rats.

Following i.p. administration of bolus doses of PD-121, 981 (0.03 to 3 mg/kg) in CCI-rats, there was a rapid onset of dose-dependent anti-allodynia in the ipsilateral hindpaw that peaked at 0.5-0.75 h post-dosing (FIG. 11A). For the doses tested, peak anti-allodynia in the ipsilateral hindpaw occurred at 0.5-1.0 h post-dosing and the corresponding durations of action were 2-3 h. Administration of PD-121,981 in doses up to 3 mg/kg in CCI-rats produced insignificant antinociception in the contralateral hindpaw (FIG. 11B). Following oral administration of bolus doses of PD-121,981 (1 mg/kg) to CCI-rats, the extent and duration of the anti-allodynic response was similar to that produced by the same dose of PD-121,981 administered to CCI-rats by the i.p. route (FIG. 12). Irrespective of dosing route, the duration of action was ~3 h (FIG. 12).

Example 10

PD-126,055 Relieves Tactile Allodynia in CCI RATS

Figure 13:
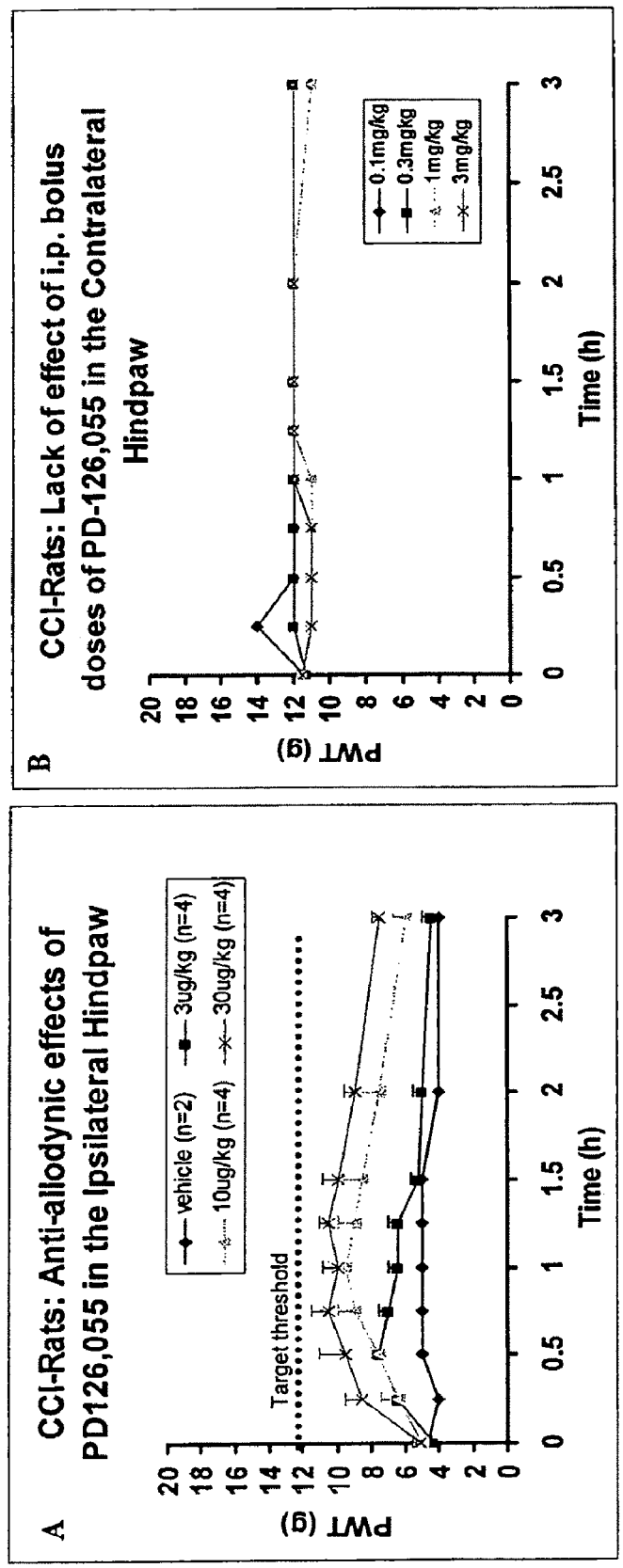
FIG. 13 is a graphical representation showing that (A) single i.p. bolus doses of PD-126,055 (3-30 µg/kg) produce dose-dependent relief of tactile allodynia in the ipsilateral hindpaw of CCI-rats. (B) By contrast, the same doses of PD-126,055 produced insignificant antinociception in the contralateral hindpaws of the same animals.
Figure 14:
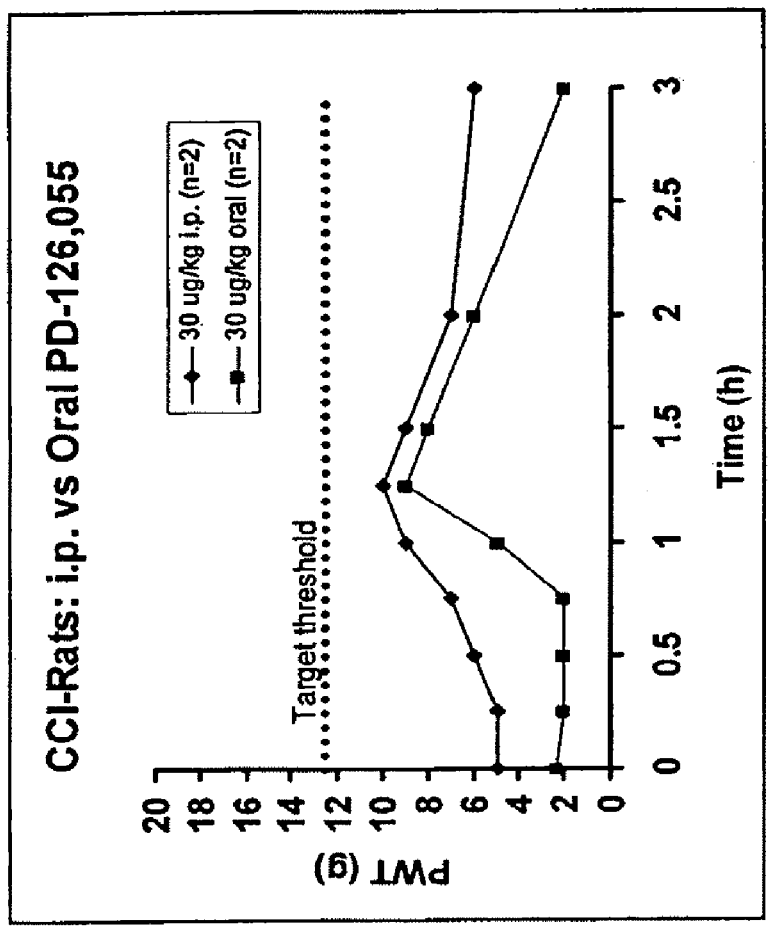
FIG. 14 is a graphical representation showing that the extent and duration of the anti-allodynic effects produced by single bolus i.p. and oral doses of PD-126,055 (30 µg/kg) are similar for the two routes of administration in CCI-rats.

Bolus i.p. doses of PD-126,055 (3 to 30 µg/kg), or vehicle were administered to CCI-rats once tactile allodynia was fully developed in the ipsilateral (injured) hindpaw. Administration of PD-126,055 in doses of 3 to 30 µg/kg, produced a rapid dose-dependent onset of anti-allodynia in the ipsilateral hindpaw (FIG. 13A) with peak responses observed at 0.75-1 h post-dosing. The corresponding durations of action were 1.5 at the lowest dose tested (3 µg/kg) and >3 h for doses larger than 3 µg/kg. Administration of PD-126,055 in doses up to 30 µg/kg in CCI-rats produced insignificant antinociception in the contralateral hindpaw (FIG. 13B). Following oral administration of bolus doses of PD-126,055 (30 µg/kg) to CCI-rats, the extent and duration of the anti-allodynic response was similar to that produced by the same dose of PD-126,055 administered to CCI-rats by the i.p. route (FIG. 14). Irrespective of dosing route, the duration of action was ~3 h (FIG. 14).

Example 11

L-161,638 (Sodium Salt) Relieves Tactile Allodynia in CCI Rats

Figure 15:
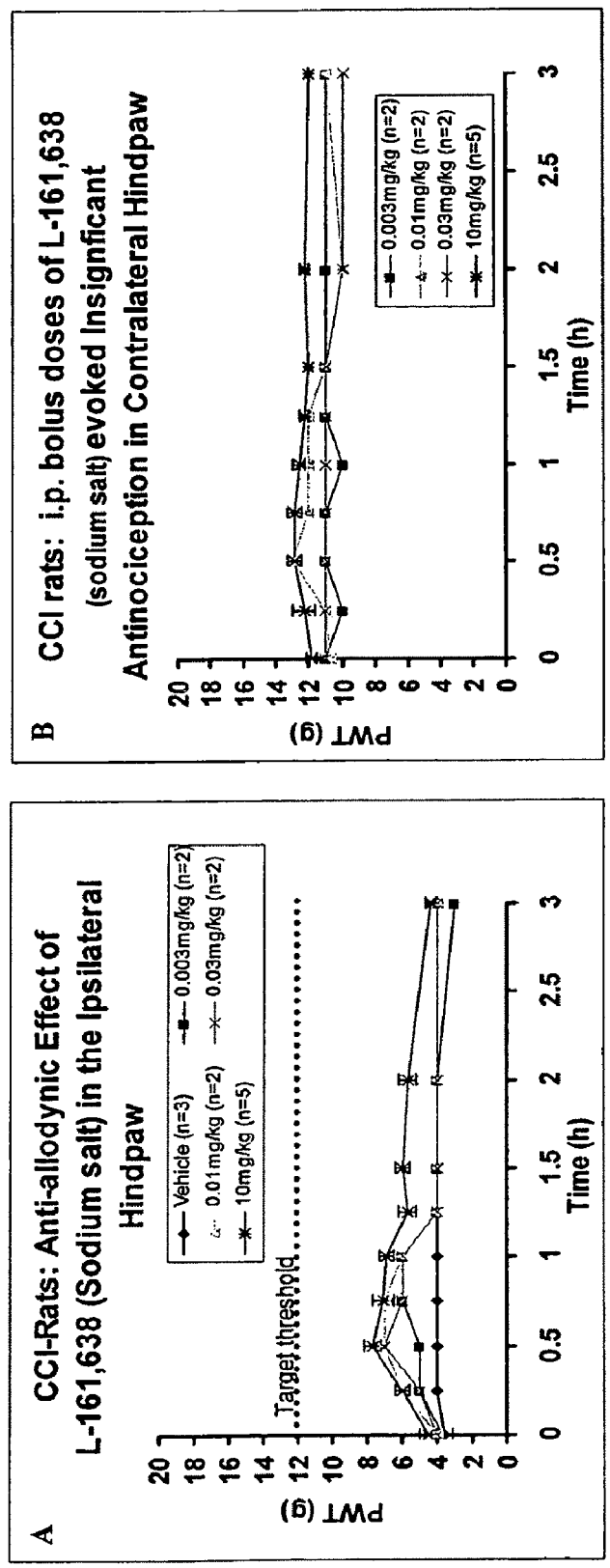
FIG. 15 is a graphical representation showing that administration of bolus i.p. doses of L-161,638 (sodium salt) (0.003-10 mg/kg) produced (A) dose-dependent relief of tactile allodynia in the ipsilateral hindpaw and (B) insignificant antinociception the contralateral hindpaw of the same animals.

Bolus i.p. doses of L-161,638 (0.003 to 10 mg/kg) produced a rapid onset of dose-dependent anti-allodynia in the ipsilateral hindpaw of CCI-rats with peak responses observed at 0.5-0.75 h post-dosing (FIG. 15A). By contrast, i.p. administration of vehicle produced insignificant relief of tactile allodynia (FIG. 15A). The corresponding durations of action were in the range 1.5-3 h. Administration of L-161,638 in doses up to 10 mg/kg in CCI-rats produced insignificant antinociception in the contralateral hindpaw (FIG. 15B).

Example 12

L-163,579 Relieves Tactile Allodynia in CCI Rats

Figure 16:
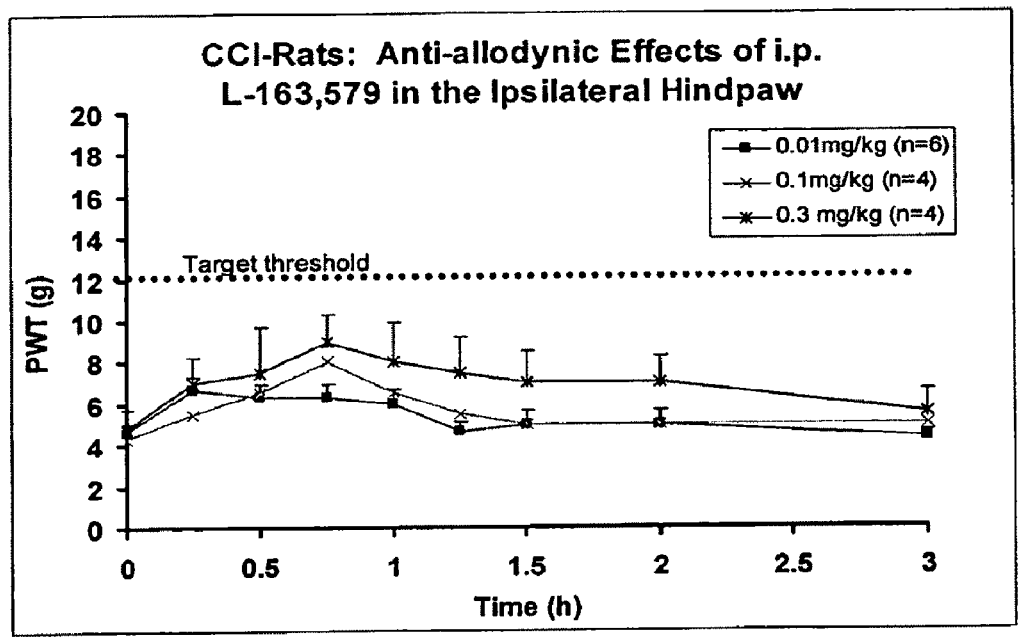
FIG. 16 is a graphical representation showing that administration of bolus i.p. doses of L-163,579 (0.01-0.3 mg/kg) to CCI-rats produced dose-dependent relief of tactile allodynia in the ipsilateral hindpaw.

Bolus i.p. doses of L-163,579 (0.01 to 0.3 mg/kg), or vehicle were administered to CCI-rats once tactile allodynia was fully developed in the ipsilateral (injured) hindpaw. Following administration of L-163,579 in doses of 0.01-0.3 mg/kg, there was a rapid onset of anti-allodynia in the ipsilateral hindpaw (FIG. 16) with peak responses observed at 0.25-0.75 h post-dosing. The corresponding durations of action were in the range 1.5-3 h.

Example 13

L-159,686 Relieves Tactile Allodynia in CCI Rats

Figure 17:
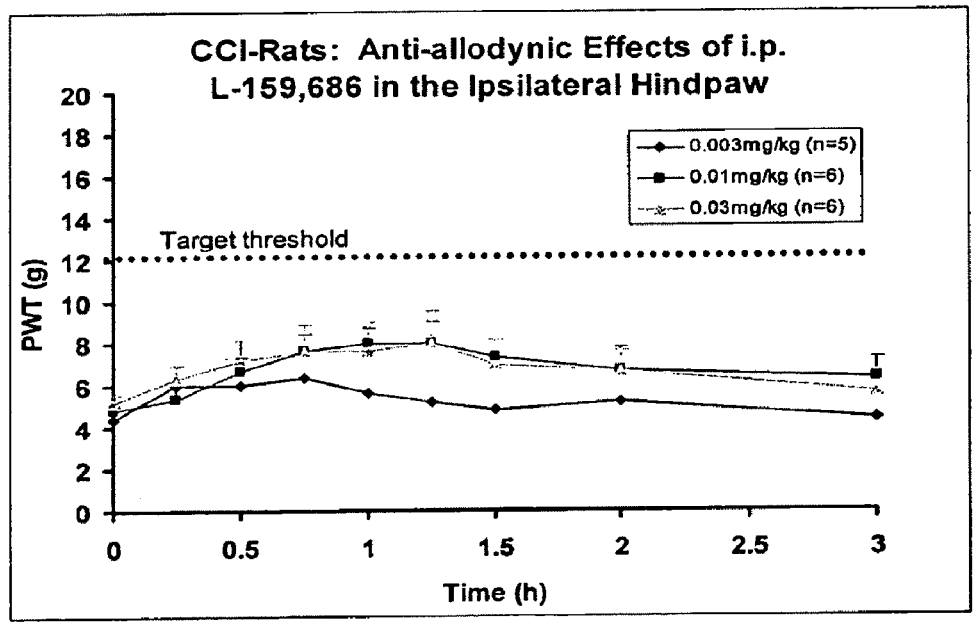
FIG. 17 is a graphical representation showing that administration of bolus i.p. doses of L-159,686 (0.003-0.03 mg/kg) to CCI-rats produced dose-dependent relief of tactile allodynia in the ipsilateral hindpaw.

Bolus i.p. doses of L-159,686 (0.003 to 0.03 mg/kg) produced dose-dependent relief of tactile allodynia in the ipsilateral (injured) hindpaw of CCI-rats (FIG. 17).

Peak anti-allodynic effects were observed at ~0.75-1 h post-dosing and for doses in the range 0.01-0.03 mg/kg, the duration of action was >3 h.

Discussion of Examples 4-13

Single i.p. bolus doses of each of the $AT_2$ receptor antagonists, PD-121,981, PD126,055, L-161,638 (sodium salt), L-163,579 and L-159,686, produced potent relief of tactile allodynia in the STZ-diabetic rat model of PDN. For test articles PD-121,981, PD126,055, L-161,638 (sodium salt) and L-163,579, there was a relatively rapid onset of anti-allodynia with peak responses observed at 0.25-1.0 h post-dosing. For the higher doses of 121,981, PD126,055, L-161, 638 (sodium salt) and L-163,579 tested, tactile allodynia in the hindpaws of STZ-diabetic rats was fully reversed and the corresponding durations of action were ≧3 h. Single i.p. bolus doses of L-159,686 at 10 µg/kg in STZ-diabetic rats produced sub-maximal anti-allodynic responses which were not further increased when the dose was escalated 10-fold to 100 µg/kg.

Interestingly, considerably larger doses of each of PD-121,981, PD126,055, L-161,638 (sodium salt) and L-163,579 were required to produce significant relief of tactile allodynia in CCI-rats compared with STZ-diabetic rats. Thus, despite the fact that CCI- and STZ-diabetic rat models of neuropathic pain show similar behavioural signs, i.e. both groups have fully developed tactile allodynia (the defining symptom of neuropathic pain), the present findings indicate that the underlying pathophysiology of these two types of neuropathic pain is quite different. For the majority of the compounds tested, there was insignificant antinociception produced in the contralateral hindpaw indicating that the anti-allodynic responses were produced through blockade of a target involved in producing the pain response rather than through amplification of the endogenous descending pain inhibitory system.

Encouragingly, the mean extent and duration of anti-allodynia produced by oral bolus doses of PD-121,981 (0.1 μg/kg) in STZ-diabetic rats was similar to that produced by the same dose administered by the i.p. route. Additionally, the anti-allodynic responses produced by oral bolus doses of PD-121,981 (1 mg/kg) and PD-126,055 (30 μg/kg) in CCI-rats were similar to the responses evoked by the respective doses given by the i.p. route. These observations suggest that PD-121,981 and PD-126,055 are not metabolised significantly in the gut wall and they are not substrates for P-glycoprotein in the gut wall, but experimental confirmation is required.

Experimental for Examples 4-11

Reagents and Materials

Isoflurane (Forthane®) and sodium benzylpenicillin vials were purchased from Abbott Australasia Pty Ltd (Sydney, Australia) and CSL Limited (Melbourne, Australia), respectively. Bupivacaine injection vials were purchased from Provet Qld Pty Ltd (Brisbane, Australia). Normal saline ampoules were obtained from Delta West Pty Ltd (Perth, Australia) and Abbott Australasia (Sydney, Australia). Sterile siliconized silk sutures (Dysilk™) were obtained from Dynek Pty Ltd (Adelaide, South Australia). Single lumen polyethylene tubing (Inner diameter (I.D.) 0.4 mm, Outer diameter (O.D.) 0.8 mm) was purchased from Auburn Plastics and Engineering Pty Ltd (Sydney, Australia). Medisense® 'Precision Plus' blood glucose meters were purchased from Abbott Laboratories, (MA, USA).

Test Articles $AT_2$ Receptor Antagonist Compounds

PD-121,981, as described in U.S. Pat. No. 4,812,462, was synthesized in the laboratory of Dr Craig Williams, Dept of Chemistry, The University of Queensland (Brisbane, Australia). PD-126,055, as described in International Publication No. WO 93/23378, was synthesized and supplied by Industrial Research Limited (IRL) (New Zealand). EMA500, which is the sodium salt of L-161,638 (L-161,638 is described by Glinka et al. 1994, Bioorg. Med. Chem. Lett. 4:1479 and in U.S. Pat. No. 5,204,354), and L-163,579, as described by Glinka et al. (1994, Bioorg. Med. Chem. Lett. 4:2337) and in U.S. Pat. No. 5,441,959, were synthesized and supplied by Industrial Research Limited (IRL) (New Zealand).

Preparation of thiophene-2-carboxylic acid benzyl-{2-ethyl-4-oxo-3-[2'-(2H-tetrazol-5yl)-biphenyl-4-ylmethyl]-3,4-dihydro-quinazolin-6-yl}-amide Sodium Salt

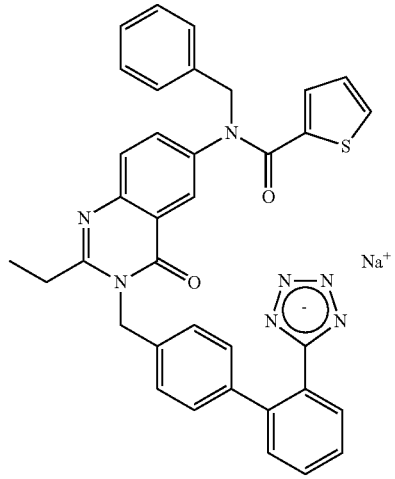

To a solution of L-161,638 [581 mg (95% pure, 5% cyclohexane), 0.884 mmol] in methanol (10 mL) and tetrahydrofuran (10 mL) was added sodium hydroxide (0.882 mL, 0.9976 M, 0.880 mmol). After 30 min at ambient temperature the volatiles were removed under reduced pressure. The resultant film was redissolved in water and concentrated under reduced pressure (water bath T=40° C.). The product was freeze dried to give EMA500 as an off-white powder (571 mg, 0.884 mol, quantitative). m.p. 207-211° C.;

$C_{36}H_{28}N_7NaO_2S \cdot 2.5H_2O$: requires C, 63.42%; H, 4.73%; N, 14.38%, S, 4.70%. found C, 63.27%; H, 4.80%; N, 14.40%; S, 4.58%; HRMS (ES) $C_{36}H_{28}N_7O_2S$ (M-) requires 622.2025. found 622.2033.

Animals

Adult male Sprague-Dawley (SD) rats were purchased from the Herston Medical Research Centre, The University of Queensland. Rats were housed in a temperature controlled environment (21±2° C.) with a 12 h/12 h light/dark cycle. Food and water were available ad libitum. Rats were given an acclimatization period of at least 3 days prior to initiation of experimentation. Ethical approval for these studies was obtained from the Animal Experimentation Ethics Committee of The University of Queensland.

Induction of STZ-Diabetes in Rats and Development of Tactile Allodynia

Diabetes Induction

Whilst adult male SD rats were anaesthetized with 3% isoflurane: 97% oxygen, a short polyethylene cannula (0.4 mm ID, 0.8 mm OD) was inserted into the jugular vein to facilitate the intravenous (i.v.) administration of a single dose of STZ (75 mg/kg). After removal of the i.v. cannula, the jugular vein was tied off, the wound was closed and topical bupivacaine was applied. Rats received benzylpenicillin (60 mg s.c.) to prevent infection and were kept warm during surgical recovery. Rats were housed singly prior to further experimentation and were monitored daily from the time of STZ administration with regard to general health and well-being. The diabetes diagnosis was confirmed on day 10 post-STZ administration if blood glucose concentrations were $\geq 15$ mM when measured using a Medisense® device and daily water intake was greater than 100 mL.

Tactile Allodynia Development

Calibrated von Frey filaments were used to determine the lowest mechanical threshold required to produce a brisk paw withdrawal reflex in the hindpaws of the rat. Briefly, rats were transferred individually to wire mesh testing cages (20 cm×20 cm×20 cm) and allowed to acclimatise for approximately 10-20 min prior to von Frey testing. Commencing with the von Frey filament that produced the lowest force, the filament was applied to the plantar surface of the hindpaw until the filament buckled slightly. Absence of a response after 5 prompted use of the next filament of increasing force. Filaments used produced a buckling weight of 2, 4, 6, 8, 10, 12, 14, 16, 18 and 20 g. A score of 20 g was given to animals that did not respond to any of the von Frey filaments. Before the administration of STZ, baseline von Frey measurements were assessed. Following STZ administration, baseline von Frey PWTs were assessed in the hindpaws at periodic intervals to monitor the development of diabetes-induced tactile allodynia. Tactile allodynia was fully developed by ~6-8 wks post-STZ administration when von Frey paw withdrawal thresholds were $\leq 6$ g; the corresponding pre-diabetic paw withdrawal thresholds were ~12 g.

Induction of a Chronic Constriction Injury of the Sciatic Nerve and the Development of Tactile Allodynia Induction of a Chronic Constriction Injury (CCI) of the Sciatic Nerve Whilst adult male SD rats were anaesthetized with 3% isoflurane: 97% oxygen, four loose ligatures were tied around one sciatic nerve to produce a unilateral chronic constriction injury (CCI) according to the method of Bennett and Xie (1988, Pain 33: 87-107). Briefly, the left common sciatic nerve was exposed at mid-thigh level by blunt dissection through the biceps femoris. Proximal to the trifurcation, ≈10 mm of nerve was freed of adhering tissue and four loose ligatures (3.0 silk) were tied around the sciatic nerve (≈1 mm apart). The incision was closed in layers. After surgery, rats received benzylpenicillin (60 mg s.c.) to prevent infection and were kept warm during surgical recovery. Rats were housed singly prior to further experimentation and were monitored daily from the time of CCI-surgery with regard to general health and well-being.

Tactile Allodynia Development

The time course for the development of tactile allodynia was documented using calibrated von Frey filaments. Tactile allodynia was considered to be fully developed in the ipsilateral (injured) hindpaw when von Frey paw withdrawal thresholds (PWTs) were $\leq 6$ g; the corresponding PWTs for the contralateral (non-injured) hindpaw remained unaltered by the CCI-surgery and were ~12 g. Tactile allodynia was fully developed in the ipsilateral hindpaw by ~10-14 days after CCI-surgery.

Test Article Administration in STZ- and CCI-Rats

Single bolus doses of each of PD-121,981, L-161,638 (sodium salt), L-163,579 and L-159,686 were administered by the intraperitoneal (i.p.) route to groups of STZ-diabetic rats and to groups of CCI-rats in accordance with a 'washout' protocol such that there was at least a 3 day washout period between successive bolus doses of the test articles of interest. Additionally, in a preliminary study, PD-121,981 was administered by the oral route to groups of each of STZ-diabetic rats and CCI-rats.

Assessment of Anti-Allodynic Efficacy

The ability of the test articles of interest to produce dose-dependent relief of tactile allodynia in groups of STZ- and CCI-rats was assessed using von Frey filaments pre-dose and at the following post-dosing times: 0.25, 0.5, 0.45, 1, 1.25, 1.5, 2, 3 h. The treatment goal was to achieve von Frey PWTs that matched those determined in the same rats prior to STZ-diabetes induction or prior to CCI-surgery (~12 g).

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method of treating neuropathic pain in a neuropathy caused by a chemotherapy drug, comprising administering to the subject an effective amount of an $AT_2$ receptor antagonist selected from compounds represented by formula (X) or pharmaceutically compatible salts thereof:

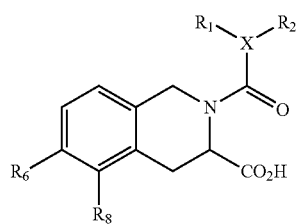

(X)

wherein X is selected from CH or nitrogen;

$R^1$ and $R^2$ are independently selected from phenyl, substituted phenyl, benzyl, substituted benzyl, $C_1$-$C_6$alkyl, substituted $C_1$-$C_6$alkyl, $C_3$-$C_6$cycloalkyl, substituted $C_3$-$C_6$cycloalkyl and heteroaryl; and $R^6$ and $R^8$ are independently selected from H, $C_{1-6}$alkyl, substituted $C_1$-$C_6$alkyl, $C_1$-$C_6$alkoxy, substituted $C_1$-$C_6$alkoxy, phenyl, phenyloxy, benzyl, benzyloxy, benzylamino, biphenyl, substituted biphenyl, biphenyloxy, substituted biphenyloxy, naphthyl, substituted naphthyl, provided that one of $R^6$ and $R^8$ is not hydrogen.

2. A method according to claim 1, wherein the $AT_2$ receptor antagonist, or pharmaceutically compatible salt thereof, is selected from compounds represented by formula (X) wherein $R^1$ and $R^2$ are independently selected from phenyl or substituted phenyl, X is CH, $R^6$ is selected from $C_1$-$C_6$alkyl, substituted $C_1$-$C_6$alkyl, $C_1$-$C_6$alkoxy, substituted $C_1$-$C_6$alkoxy, phenyl and phenyloxy and $R^8$ is selected from hydrogen, phenyl, phenyloxy, benzyl, benzyloxy, benzylamino, biphenyl, substituted biphenyl, biphenyloxy, substituted biphenyloxy, naphthyl and substituted naphthyl.

3. A method according to claim 1 wherein at least one of $R^1$ and $R^2$ is selected from phenyl or substituted phenyl.

4. A method according to claim 3 wherein at least one of $R^1$ and $R^2$ is phenyl.

5. A method according to claim 1 wherein both $R^1$ and $R^2$ are selected from phenyl and substituted phenyl.

6. A method according to claim 5 wherein both $R^1$ and $R^2$ are phenyl.

7. A method according to claim 1 wherein $R^6$ is selected from $C_1$-$C_6$alkyl and $C_1$-$C_6$alkoxy.

8. A method according to claim 7 wherein $R^6$ is $C_1$-$C_3$alkoxy.

9. A method according to claim 8 wherein $R^6$ is methoxy.

10. A method according to claim 1 wherein $R^8$ is selected from benzyl, benzyloxy and benzylamino.

11. A method according to claim 10 wherein $R^8$ is benzyloxy.

12. A method according to claim 1 wherein the $AT_2$ receptor antagonist is 2-(diphenylacetyl)-5-benzyloxy-6-methoxy-1,2,3,4-tetrahydroisoquinoline-3-carboxylic acid (PD-126055) or an enantiomer thereof or a pharmaceutically compatible salt thereof.

13. A method according to claim 1 wherein the chemotherapy drug is vincristine.

* * * * *

SEQUENCE LISTING

```
<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 1
```

```
Asn Arg Val Tyr Val His Pro Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 2

Asn Arg Val Tyr Val His Pro Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MISC_FEATURE
<222> LOCATION: (1)..(1)
<223> OTHER INFORMATION: Arg may be modified with a succinyl moiety

<400> SEQUENCE: 3

Arg Val Tyr Val His Pro Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 4

Asp Arg Val Tyr Val His Pro Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic AT2 receptor antagonist peptide

<400> SEQUENCE: 5

Arg Val Tyr Val His Pro Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MISC_FEATURE
<222> LOCATION: (1)..(1)
<223> OTHER INFORMATION: Xaa = Sarcosine

<400> SEQUENCE: 6

Xaa Arg Val Tyr His Pro Ala
1               5

<210> SEQ ID NO 7
<211> LENGTH: 7
<212> TYPE: PRT
```

```
<213> ORGANISM: Artificial Sequence
<220> FEATURE:
<223> OTHER INFORMATION: Synthetic AT2 receptor antagonist peptide

<400> SEQUENCE: 7

Ser Arg Val Tyr His Pro Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MOD_RES
<222> LOCATION: (1)..(1)
<223> OTHER INFORMATION: Arg may be modified with a succinamyl moiety

<400> SEQUENCE: 8

Arg Val Tyr Val His Pro Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 9

Asn Arg Val Tyr Val His Pro Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 10

Asn Arg Val Tyr Val His Pro Ile
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MISC_FEATURE
<222> LOCATION: (1)..(1)
<223> OTHER INFORMATION: Xaa = sarcosine

<400> SEQUENCE: 11

Xaa Arg Val Tyr Val His Pro Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 12

Pro Arg Val Tyr Val His Pro Gly
```

```
<210> SEQ ID NO 13
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 13

Asn Arg Val Tyr Val His Pro Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MISC_FEATURE
<222> LOCATION: (1)..(1)
<223> OTHER INFORMATION: Xaa = sarcosine
<220> FEATURE:
<221> NAME/KEY: MISC_FEATURE
<222> LOCATION: (8)..(8)
<223> OTHER INFORMATION: Xaa = beta-alanine

<400> SEQUENCE: 14

Xaa Arg Val Tyr Val His Pro Xaa
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MISC_FEATURE
<222> LOCATION: (8)..(8)
<223> OTHER INFORMATION: Xaa = beta-alanine

<400> SEQUENCE: 15

Asn Arg Val Tyr Val His Pro Xaa
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 16

Gly Arg Val Tyr Val His Pro Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MISC_FEATURE
<222> LOCATION: (1)..(1)
<223> OTHER INFORMATION: Xaa = sarcosine

<400> SEQUENCE: 17
```

```
Xaa Arg Val Tyr Ile His Pro Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 18

Asn Arg Val Tyr Val His Pro Leu
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MISC_FEATURE
<222> LOCATION: (1)..(1)
<223> OTHER INFORMATION: Xaa = sarcosine

<400> SEQUENCE: 19

Xaa Arg Val Tyr Ile His Pro Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 20

Asn Arg Val Tyr Ile His Pro Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 21

Asn Arg Val Tyr Ala His Pro Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic AT2 receptor antagonist peptide

<400> SEQUENCE: 22

Asp Arg Val Phe Ile His Pro Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic AT2 receptor antagonist peptide
<220> FEATURE:
```

```
<221> NAME/KEY: MISC_FEATURE
<222> LOCATION: (6)..(6)
<223> OTHER INFORMATION: Xaa = para-amino-phenylalanine

<400> SEQUENCE: 23

Asp Arg Val Tyr Ile Xaa Pro Phe
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic AT2 receptor antagonist peptide
<220> FEATURE:
<221> NAME/KEY: MOD_RES
<222> LOCATION: (1)..(1)
<223> OTHER INFORMATION: Tyr may be modified with nicotinic acid
<220> FEATURE:
<221> NAME/KEY: MISC_FEATURE
<222> LOCATION: (2)..(2)
<223> OTHER INFORMATION: Xaa = N-benzoylcarbonyl-arginine

<400> SEQUENCE: 24

Tyr Xaa Lys His Pro Ile
1               5

<210> SEQ ID NO 25
<211> LENGTH: 363
<212> TYPE: PRT
<213> ORGANISM: Homo sapiens

<400> SEQUENCE: 25

Met Lys Gly Asn Ser Thr Leu Ala Thr Thr Ser Lys Asn Ile Thr Ser
1               5                   10                  15

Gly Leu His Phe Gly Leu Val Asn Ile Ser Gly Asn Asn Glu Ser Thr
                20                  25                  30

Leu Asn Cys Ser Gln Lys Pro Ser Asp Lys His Leu Asp Ala Ile Pro
            35                  40                  45

Ile Leu Tyr Tyr Ile Ile Phe Val Ile Gly Phe Leu Val Asn Ile Val
        50                  55                  60

Val Val Thr Leu Phe Cys Cys Gln Lys Gly Pro Lys Lys Val Ser Ser
65                  70                  75                  80

Ile Tyr Ile Phe Asn Leu Ala Val Ala Asp Leu Leu Leu Leu Ala Thr
                85                  90                  95

Leu Pro Leu Trp Ala Thr Tyr Tyr Ser Tyr Arg Tyr Asp Trp Leu Phe
            100                 105                 110

Gly Pro Val Met Cys Lys Val Phe Gly Ser Phe Leu Thr Leu Asn Met
        115                 120                 125

Phe Ala Ser Ile Phe Phe Ile Thr Cys Met Ser Val Asp Arg Tyr Gln
    130                 135                 140

Ser Val Ile Tyr Pro Phe Leu Ser Gln Arg Arg Asn Pro Trp Gln Ala
145                 150                 155                 160

Ser Tyr Ile Val Pro Leu Val Trp Cys Met Ala Cys Leu Ser Ser Leu
                165                 170                 175

Pro Thr Phe Tyr Phe Arg Asp Val Arg Thr Ile Glu Tyr Leu Gly Val
            180                 185                 190

Asn Ala Cys Ile Met Ala Phe Pro Pro Glu Lys Tyr Ala Gln Trp Ser
        195                 200                 205

Ala Gly Ile Ala Leu Met Lys Asn Ile Leu Gly Phe Ile Ile Pro Leu
    210                 215                 220
```

Ile Phe Ile Ala Thr Cys Tyr Phe Gly Ile Arg Lys His Leu Leu Lys
225                 230                 235                 240

Thr Asn Ser Tyr Gly Lys Asn Arg Ile Thr Arg Asp Gln Val Leu Lys
            245                 250                 255

Met Ala Ala Val Val Leu Ala Phe Ile Ile Cys Trp Leu Pro Phe
        260                 265                 270

His Val Leu Thr Phe Leu Asp Ala Leu Ala Trp Met Gly Val Ile Asn
        275                 280                 285

Ser Cys Glu Val Ile Ala Val Ile Asp Leu Ala Leu Pro Phe Ala Ile
    290                 295                 300

Leu Leu Gly Phe Thr Asn Ser Cys Val Asn Pro Phe Leu Tyr Cys Phe
305                 310                 315                 320

Val Gly Asn Arg Phe Gln Gln Lys Leu Arg Ser Val Phe Arg Val Pro
            325                 330                 335

Ile Thr Trp Leu Gln Gly Lys Arg Glu Ser Met Ser Cys Arg Lys Ser
            340                 345                 350

Ser Ser Leu Arg Glu Met Glu Thr Phe Val Ser
        355                 360

<210> SEQ ID NO 26
<211> LENGTH: 363
<212> TYPE: PRT
<213> ORGANISM: Mus sp.

<400> SEQUENCE: 26

Met Lys Asp Asn Phe Ser Phe Ala Ala Thr Ser Arg Asn Ile Thr Ser
1               5                   10                  15

Ser Arg Pro Phe Asp Asn Leu Asn Ala Thr Gly Thr Asn Glu Ser Ala
            20                  25                  30

Phe Asn Cys Ser His Lys Pro Ser Asp Lys His Leu Glu Ala Ile Pro
        35                  40                  45

Val Leu Tyr Tyr Met Ile Phe Val Ile Gly Phe Ala Val Asn Ile Val
    50                  55                  60

Val Val Ser Leu Phe Cys Cys Gln Lys Gly Pro Lys Lys Val Ser Ser
65                  70                  75                  80

Ile Tyr Ile Phe Asn Leu Ala Leu Ala Asp Leu Leu Leu Leu Ala Thr
                85                  90                  95

Leu Pro Leu Trp Ala Thr Tyr Tyr Ser Tyr Arg Tyr Asp Trp Leu Phe
            100                 105                 110

Gly Pro Val Met Cys Lys Val Phe Gly Ser Phe Leu Thr Leu Asn Met
        115                 120                 125

Phe Ala Ser Ile Phe Phe Ile Thr Cys Met Ser Val Asp Arg Tyr Gln
130                 135                 140

Ser Val Ile Tyr Pro Phe Leu Ser Gln Arg Arg Asn Pro Trp Gln Ala
145                 150                 155                 160

Ser Tyr Val Val Pro Leu Val Trp Cys Met Ala Cys Leu Ser Ser Leu
                165                 170                 175

Pro Thr Phe Tyr Phe Arg Asp Val Arg Thr Ile Glu Tyr Leu Gly Val
            180                 185                 190

Asn Ala Cys Ile Met Ala Phe Pro Pro Glu Lys Tyr Ala Gln Trp Ser
        195                 200                 205

Ala Gly Ile Ala Leu Met Lys Asn Ile Leu Gly Phe Ile Ile Pro Leu
    210                 215                 220

Ile Phe Ile Ala Thr Cys Tyr Phe Gly Ile Arg Lys His Leu Leu Lys
225                 230                 235                 240

-continued

```
Thr Asn Ser Tyr Gly Lys Asn Arg Ile Thr Arg Asp Gln Val Leu Lys
            245                 250                 255

Met Ala Ala Ala Val Val Leu Ala Phe Ile Ile Cys Trp Leu Pro Phe
        260                 265                 270

His Val Leu Thr Phe Leu Asp Ala Leu Thr Trp Met Gly Ile Ile Asn
        275                 280                 285

Ser Cys Glu Val Ile Ala Val Ile Asp Leu Ala Leu Pro Phe Ala Ile
        290                 295                 300

Leu Leu Gly Phe Thr Asn Ser Cys Val Asn Pro Phe Leu Tyr Cys Phe
305                 310                 315                 320

Val Gly Asn Arg Phe Gln Gln Lys Leu Arg Ser Val Phe Arg Val Pro
                325                 330                 335

Ile Thr Trp Leu Gln Gly Lys Arg Glu Thr Met Ser Cys Arg Lys Gly
                340                 345                 350

Ser Ser Leu Arg Glu Met Asp Thr Phe Val Ser
                355                 360
```

<210> SEQ ID NO 27
<211> LENGTH: 363
<212> TYPE: PRT
<213> ORGANISM: Rattus sp.

<400> SEQUENCE: 27

```
Met Lys Asp Asn Phe Ser Phe Ala Ala Thr Ser Arg Asn Ile Thr Ser
1               5                   10                  15

Ser Leu Pro Phe Asp Asn Leu Asn Ala Thr Gly Thr Asn Glu Ser Ala
            20                  25                  30

Phe Asn Cys Ser His Lys Pro Ala Asp Lys His Leu Glu Ala Ile Pro
        35                  40                  45

Val Leu Tyr Tyr Met Ile Phe Val Ile Gly Phe Ala Val Asn Ile Val
    50                  55                  60

Val Val Ser Leu Phe Cys Cys Gln Lys Gly Pro Lys Lys Val Ser Ser
65              70                  75                  80

Ile Tyr Ile Phe Asn Leu Ala Val Ala Asp Leu Leu Leu Leu Ala Thr
                85                  90                  95

Leu Pro Leu Trp Ala Thr Tyr Tyr Ser Tyr Arg Tyr Asp Trp Leu Phe
            100                 105                 110

Gly Pro Val Met Cys Lys Val Phe Gly Ser Phe Leu Thr Leu Asn Met
        115                 120                 125

Phe Ala Ser Ile Phe Phe Ile Thr Cys Met Ser Val Asp Arg Tyr Gln
    130                 135                 140

Ser Val Ile Tyr Pro Phe Leu Ser Gln Arg Arg Asn Pro Trp Gln Ala
145                 150                 155                 160

Ser Tyr Val Val Pro Leu Val Trp Cys Met Ala Cys Leu Ser Ser Leu
                165                 170                 175

Pro Thr Phe Tyr Phe Arg Asp Val Arg Thr Ile Glu Tyr Leu Gly Val
            180                 185                 190

Asn Ala Cys Ile Met Ala Phe Pro Pro Glu Lys Tyr Ala Gln Trp Ser
        195                 200                 205

Ala Gly Ile Ala Leu Met Lys Asn Ile Leu Gly Phe Ile Ile Pro Leu
    210                 215                 220

Ile Phe Ile Ala Thr Cys Tyr Phe Gly Ile Arg Lys His Leu Leu Lys
225                 230                 235                 240

Thr Asn Ser Tyr Gly Lys Asn Arg Ile Thr Arg Asp Gln Val Leu Lys
                245                 250                 255
```

| | | | | | | | | | | | | | | |
|---|---|---|---|---|---|---|---|---|---|---|---|---|---|---|
| Met | Ala | Ala | Ala | Val | Val | Leu | Ala | Phe | Ile | Ile | Cys | Trp | Leu | Pro | Phe |
| | | | 260 | | | | | 265 | | | | | 270 | | |
| His | Val | Leu | Thr | Phe | Leu | Asp | Ala | Leu | Thr | Trp | Met | Gly | Ile | Ile | Asn |
| | | 275 | | | | | 280 | | | | | 285 | | | |
| Ser | Cys | Glu | Val | Ile | Ala | Val | Ile | Asp | Leu | Ala | Leu | Pro | Phe | Ala | Ile |
| | 290 | | | | | 295 | | | | | 300 | | | | |
| Leu | Leu | Gly | Phe | Thr | Asn | Ser | Cys | Val | Asn | Pro | Phe | Leu | Tyr | Cys | Phe |
| 305 | | | | | 310 | | | | | 315 | | | | | 320 |
| Val | Gly | Asn | Arg | Phe | Gln | Gln | Lys | Leu | Arg | Ser | Val | Phe | Arg | Val | Pro |
| | | | | 325 | | | | | 330 | | | | | 335 | |
| Ile | Thr | Trp | Leu | Gln | Gly | Lys | Arg | Glu | Thr | Met | Ser | Cys | Arg | Lys | Ser |
| | | | | 340 | | | | | 345 | | | | | 350 | |
| Ser | Ser | Leu | Arg | Glu | Met | Asp | Thr | Phe | Val | Ser | | | | | |
| | | 355 | | | | | | 360 | | | | | | | |